(12) United States Patent
Gottlieb et al.

(10) Patent No.: US 10,723,784 B2
(45) Date of Patent: *Jul. 28, 2020

(54) COMPOSITIONS AND METHODS FOR PREPARING A SUBJECT FOR ORGAN OR NON-ORGAN IMPLANTATION

(71) Applicant: THE REGENTS OF THE UNIVERSITY OF COLORADO, A BODY CORPORATE, Denver, CO (US)

(72) Inventors: Peter Gottlieb, Englewood, CO (US); Charles Dinarello, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/279,258

(22) Filed: Sep. 28, 2016

(65) Prior Publication Data
US 2017/0015731 A1 Jan. 19, 2017

Related U.S. Application Data

(63) Continuation of application No. 14/227,414, filed on Mar. 27, 2014, now Pat. No. 9,486,509, which is a continuation of application No. PCT/US2014/031848, filed on Mar. 26, 2014.

(60) Provisional application No. 61/806,646, filed on Mar. 29, 2013.

(51) Int. Cl.
| C07K 14/81 | (2006.01) |
| A61K 38/57 | (2006.01) |
| A61K 45/06 | (2006.01) |
| A61K 39/00 | (2006.01) |
| A61K 39/395 | (2006.01) |
| C07K 16/00 | (2006.01) |
| C07K 19/00 | (2006.01) |

(52) U.S. Cl.
CPC .......... *C07K 14/8125* (2013.01); *A61K 38/57* (2013.01); *A61K 39/001* (2013.01); *A61K 39/395* (2013.01); *A61K 45/06* (2013.01); *C07K 16/00* (2013.01); *C07K 19/00* (2013.01); *A61K 2039/505* (2013.01); *A61K 2039/545* (2013.01); *A61K 2039/55* (2013.01); *A61K 2039/577* (2013.01); *C07K 2319/00* (2013.01)

(58) Field of Classification Search
CPC combination set(s) only.
See application file for complete search history.

(56) References Cited

U.S. PATENT DOCUMENTS

| 8,715,649 | B2 | 5/2014 | Dinarello et al. |
| 2002/0019344 | A1 | 2/2002 | Pershadsingh |
| 2003/0171263 | A1 | 9/2003 | Lucas et al. |
| 2008/0261869 | A1* | 10/2008 | Shapiro .............. C07K 14/8125 514/1.1 |
| 2009/0203580 | A1* | 8/2009 | Dinarello ............... A61K 38/57 514/1.1 |
| 2009/0220518 | A1 | 9/2009 | Dinarello et al. |
| 2010/0286066 | A1* | 11/2010 | Durrani ................ A61K 9/0078 514/20.9 |
| 2011/0002909 | A1* | 1/2011 | Arora ................. C07K 14/8125 424/94.62 |
| 2011/0237496 | A1* | 9/2011 | Nathan .................. A61K 31/70 514/1.4 |
| 2011/0288005 | A1* | 11/2011 | Silverman ............ C07K 16/244 514/1.8 |
| 2012/0045449 | A1* | 2/2012 | Dinarello ............... A61K 38/57 424/158.1 |
| 2012/0046450 | A1* | 2/2012 | Dall'Acqua ........... C07K 16/00 530/387.3 |
| 2012/0100166 | A1 | 4/2012 | Roschke et al. |
| 2013/0203650 | A1* | 8/2013 | Wormser ........... C07K 14/8125 514/1.4 |

FOREIGN PATENT DOCUMENTS

| EP | 0155188 A2 | 9/1985 | |
| WO | WO 2012/029061 * | 3/2012 | ............. A61K 38/57 |
| WO | 2012178102 A2 | 12/2012 | |
| WO | 2014160768 A1 | 10/2014 | |

OTHER PUBLICATIONS

Dinarello, C. A., et. al. Treating Inflammation by Blocking Interleukin-1 in a Broad Spectrum of Diseases. Nature Reviews: Drug Discovery, 11: 633-652, Aug. 2012.
International Preliminary Report on Patentability issued in PCT/US2014/031848, dated Oct. 8, 2015, 8 pages.
International Search Report and Written Opinion issued in PCT/US2014/031848, dated Jul. 14 2014, 10 pages.
Marcondes, M. A., et. al. Inhibition of IL-32 Activation by Alpha-1 Antitrypsin Suppresses Alloreactivity and Increases Survival in an Allogeneic Murine Marrow Transplantation Model. Blood, 118(18): 5031-5039, Nov. 3, 2011.
Tawara, I., et. al. Alpha-1-Antitrypsin Monotherapy Reduces Graft-Versus-Host Disease After Experimental Allogeneic Bone Marrow Transplantation. PNAS, 109(2): 564-569, Jan. 10, 2012.

* cited by examiner

*Primary Examiner* — Amber D Steele
(74) *Attorney, Agent, or Firm* — Polsinelli PC

(57) ABSTRACT

Embodiments of the present invention illustrate methods of preventing transplantation rejection. In certain embodiments, a subject in need of an organ or non-organ transplantation can be pretreated with an AAT composition to reduce the incidence of transplantation rejection in the subject. Other embodiments include treating a subject with a composition including AAT before, during or after plastic surgery.

31 Claims, 38 Drawing Sheets
Specification includes a Sequence Listing.

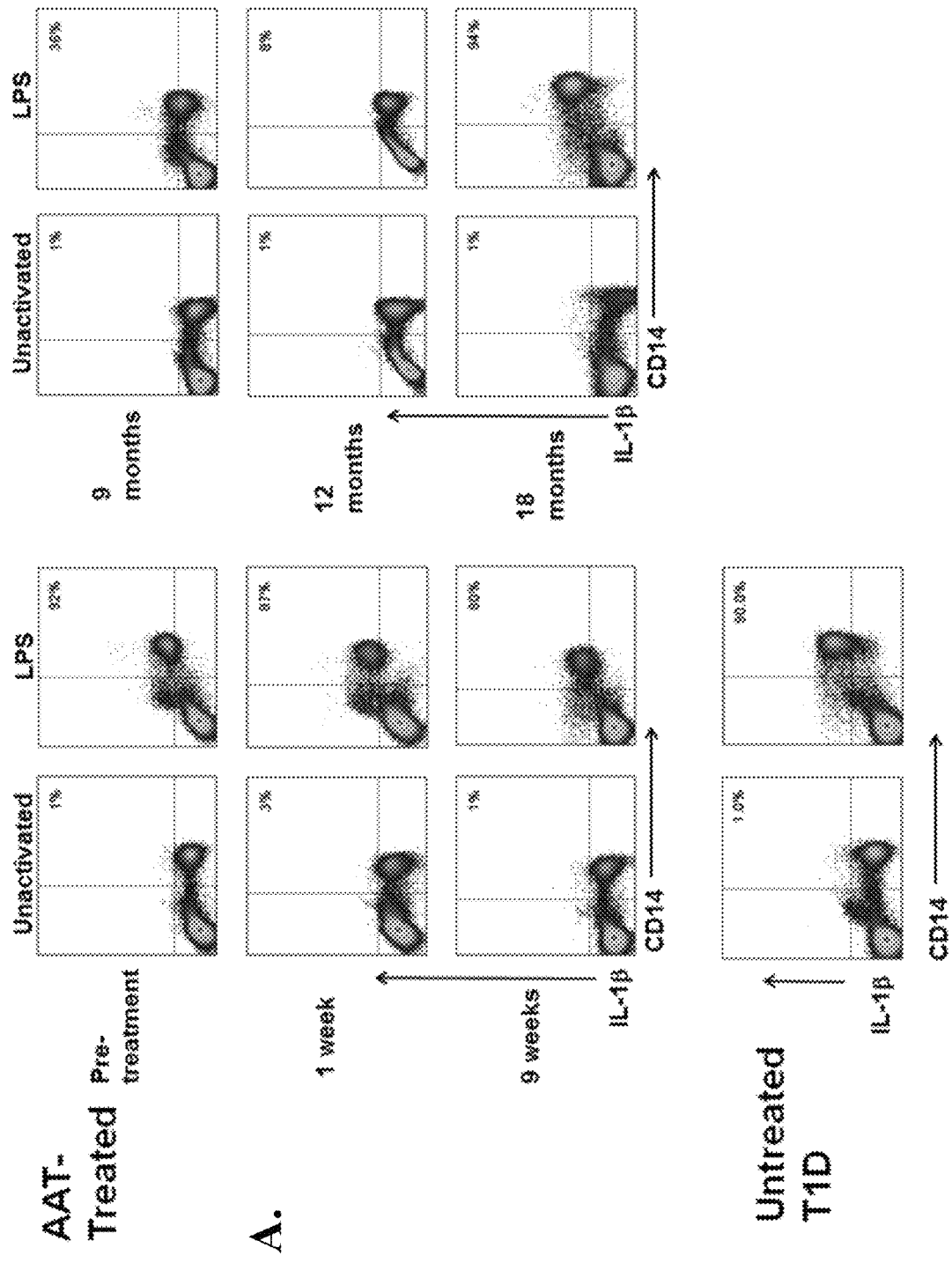

Clinical Characteristics at Baseline

For Subjects with T1D Duration > 1 Year at Initiation of AAT Therapy

| Subject ID | Age (years) | T1D Duration (months) |
|---|---|---|
| 003 | 39 | 44 |
| 005 | 20 | 40 |
| 007 | 22 | 21 |
| 009 | 30 | 30 |

AAT Therapy = 80 mg/kg i.v. weekly for 8 weeks

Fig. 10

Clinical Characteristics at Baseline

For Subjects with T1D Duration < 1 Year at Initiation of AAT Therapy

| Subject ID | Age (years) | T1D Duration (months) |
|---|---|---|
| 002 | 39 | 7 |
| 004 | 33 | 4 |
| 010 | 38 | 9 |
| 013 | 15 | 3 |
| 014 | 14 | 5 |
| 015 | 15 | 5 |
| 018 | 12 | 3 |

AAT Therapy = 80 mg/kg i.v. weekly for 8 weeks

Fig. 11 Fall in C-peptide in Control T1D subjects over 1st 2 yrs from Dx

Type 1 Diabetes: Predicted 6 month fall in C-peptide: 25% pediatric, 15% adult

Figs. 32A-32D Monocytes Expressing IL-1β

SEQUENCE LISTING

```
<160> NUMBER OF SEQ ID NOS: 115

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Phe Val Phe Leu Met
1               5

<210> SEQ ID NO 2
```

```
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Ala Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Phe Val Ala Leu Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Phe Leu Ala
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Leu Val Phe Ile
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Met Ile Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Phe Leu Phe Val Leu
1               5

<210> SEQ ID NO 8
<211> LENGTH: 5
```

```
<212> TYPE: PRT
<213> ORGANISM: Artificial
<220> FEATURE:
<223> OTHER INFORMATION: synthetic peptide

<400> SEQUENCE: 8

Phe Leu Phe Val Val
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Leu Ile
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Phe Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Met Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Met Leu Leu Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Ile Ile Met Ile
1               5

<210> SEQ ID NO 14
<211> LENGTH: 5
<212> TYPE: PRT
```

```
<213> ORGANISM: Artificial
<220> FEATURE:
<223> OTHER INFORMATION: synthetic peptide

<400> SEQUENCE: 14

Phe Leu Phe Cys Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Ala Val
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Val Tyr Leu Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Ala Phe Leu Met
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Ala Val Phe Leu Met
1               5

<210> SEQ ID NO 19
<211> LENGTH: 10
<212> TYPE: PRT
<213> ORGANISM: Homo sapiens

<400> SEQUENCE: 19

Met Pro Ser Ser Val Ser Trp Gly Ile Leu
1               5                   10

<210> SEQ ID NO 20
<211> LENGTH: 10
<212> TYPE: PRT
<213> ORGANISM: Homo sapiens

<400> SEQUENCE: 20
```

Leu Ala Gly Leu Cys Cys Leu Val Pro Val
1               5                   10

<210> SEQ ID NO 21
<211> LENGTH: 10
<212> TYPE: PRT
<213> ORGANISM: Homo sapiens

<400> SEQUENCE: 21

Ser Leu Ala Glu Asp Pro Gln Gly Asp Ala
1               5                   10

<210> SEQ ID NO 22
<211> LENGTH: 10
<212> TYPE: PRT
<213> ORGANISM: Homo sapiens

<400> SEQUENCE: 22

Ala Gln Lys Thr Asp Thr Ser His His Asp
1               5                   10

<210> SEQ ID NO 23
<211> LENGTH: 10
<212> TYPE: PRT
<213> ORGANISM: Homo sapiens

<400> SEQUENCE: 23

Gln Asp His Pro Thr Phe Asn Lys Ile Thr
1               5                   10

<210> SEQ ID NO 24
<211> LENGTH: 10
<212> TYPE: PRT
<213> ORGANISM: Homo sapiens

<400> SEQUENCE: 24

Pro Asn Leu Ala Glu Phe Ala Phe Ser Leu
1               5                   10

<210> SEQ ID NO 25
<211> LENGTH: 10
<212> TYPE: PRT
<213> ORGANISM: Homo sapiens

<400> SEQUENCE: 25

Tyr Arg Gln Leu Ala His Gln Ser Asn Ser
1               5                   10

<210> SEQ ID NO 26
<211> LENGTH: 10
<212> TYPE: PRT
<213> ORGANISM: Homo sapiens

<400> SEQUENCE: 26

Thr Asn Ile Phe Phe Ser Pro Val Ser Ile
1               5                   10

<210> SEQ ID NO 27
<211> LENGTH: 10
<212> TYPE: PRT
<213> ORGANISM: Homo sapiens

<400> SEQUENCE: 27

Ala Thr Ala Phe Ala Met Leu Ser Leu Gly

<210> SEQ ID NO 28
<211> LENGTH: 10
<212> TYPE: PRT
<213> ORGANISM: Homo sapiens

<400> SEQUENCE: 28

Thr Lys Ala Asp Thr His Asp Glu Ile Leu
1               5                   10

<210> SEQ ID NO 29
<211> LENGTH: 10
<212> TYPE: PRT
<213> ORGANISM: Homo sapiens

<400> SEQUENCE: 29

Glu Gly Leu Asn Phe Asn Leu Thr Glu Ile
1               5                   10

<210> SEQ ID NO 30
<211> LENGTH: 10
<212> TYPE: PRT
<213> ORGANISM: Homo sapiens

<400> SEQUENCE: 30

Pro Glu Ala Gln Ile His Glu Gly Phe Gln
1               5                   10

<210> SEQ ID NO 31
<211> LENGTH: 10
<212> TYPE: PRT
<213> ORGANISM: Homo sapiens

<400> SEQUENCE: 31

Glu Leu Leu Arg Thr Leu Asn Gln Pro Asp
1               5                   10

<210> SEQ ID NO 32
<211> LENGTH: 10
<212> TYPE: PRT
<213> ORGANISM: Homo sapiens

<400> SEQUENCE: 32

Ser Gln Leu Gln Leu Thr Thr Gly Asn Gly
1               5                   10

<210> SEQ ID NO 33
<211> LENGTH: 10
<212> TYPE: PRT
<213> ORGANISM: Homo sapiens

<400> SEQUENCE: 33

Leu Phe Leu Ser Glu Gly Leu Lys Leu Val
1               5                   10

<210> SEQ ID NO 34
<211> LENGTH: 10
<212> TYPE: PRT
<213> ORGANISM: Homo sapiens

<400> SEQUENCE: 34

Asp Lys Phe Leu Glu Asp Val Lys Lys Leu
1               5                   10

<210> SEQ ID NO 35
<211> LENGTH: 10
<212> TYPE: PRT
<213> ORGANISM: Homo sapiens

<400> SEQUENCE: 35

Tyr His Ser Glu Ala Phe Thr Val Asn Phe
1               5                   10

<210> SEQ ID NO 36
<211> LENGTH: 10
<212> TYPE: PRT
<213> ORGANISM: Homo sapiens

<400> SEQUENCE: 36

Gly Asp His Glu Ala Lys Lys Gln Ile
1               5                   10

<210> SEQ ID NO 37
<211> LENGTH: 10
<212> TYPE: PRT
<213> ORGANISM: Homo sapiens

<400> SEQUENCE: 37

Asn Asp Tyr Val Glu Lys Gly Thr Gln Gly
1               5                   10

<210> SEQ ID NO 38
<211> LENGTH: 10
<212> TYPE: PRT
<213> ORGANISM: Homo sapiens

<400> SEQUENCE: 38

Lys Ile Val Asp Leu Val Lys Glu Leu Asp
1               5                   10

<210> SEQ ID NO 39
<211> LENGTH: 10
<212> TYPE: PRT
<213> ORGANISM: Homo sapiens

<400> SEQUENCE: 39

Arg Asp Thr Val Phe Ala Leu Val Asn Tyr
1               5                   10

<210> SEQ ID NO 40
<211> LENGTH: 10
<212> TYPE: PRT
<213> ORGANISM: Homo sapiens

<400> SEQUENCE: 40

Ile Phe Phe Lys Gly Lys Trp Glu Arg Pro
1               5                   10

<210> SEQ ID NO 41
<211> LENGTH: 10
<212> TYPE: PRT
<213> ORGANISM: Homo sapiens

<400> SEQUENCE: 41

Phe Glu Val Lys Asp Thr Glu Asp Glu Asp
1               5                   10

<210> SEQ ID NO 42

```
<211> LENGTH: 10
<212> TYPE: PRT
<213> ORGANISM: Homo sapiens

<400> SEQUENCE: 42

Phe His Val Asp Gln Val Thr Thr Val Lys
1               5                   10

<210> SEQ ID NO 43
<211> LENGTH: 10
<212> TYPE: PRT
<213> ORGANISM: Homo sapiens

<400> SEQUENCE: 43

Val Pro Met Met Lys Arg Leu Gly Met Phe
1               5                   10

<210> SEQ ID NO 44
<211> LENGTH: 10
<212> TYPE: PRT
<213> ORGANISM: Homo sapiens

<400> SEQUENCE: 44

Asn Ile Gln His Cys Lys Lys Leu Ser Ser
1               5                   10

<210> SEQ ID NO 45
<211> LENGTH: 10
<212> TYPE: PRT
<213> ORGANISM: Homo sapiens

<400> SEQUENCE: 45

Trp Val Leu Leu Met Lys Tyr Leu Gly Asn
1               5                   10

<210> SEQ ID NO 46
<211> LENGTH: 10
<212> TYPE: PRT
<213> ORGANISM: Homo sapiens

<400> SEQUENCE: 46

Ala Thr Ala Ile Phe Phe Leu Pro Asp Glu
1               5                   10

<210> SEQ ID NO 47
<211> LENGTH: 10
<212> TYPE: PRT
<213> ORGANISM: Homo sapiens

<400> SEQUENCE: 47

Gly Lys Leu Gln His Leu Glu Asn Glu Leu
1               5                   10

<210> SEQ ID NO 48
<211> LENGTH: 10
<212> TYPE: PRT
<213> ORGANISM: Homo sapiens

<400> SEQUENCE: 48

Thr His Asp Ile Ile Thr Lys Phe Leu Glu
1               5                   10

<210> SEQ ID NO 49
<211> LENGTH: 10
<212> TYPE: PRT
```

<213> ORGANISM: Homo sapiens

<400> SEQUENCE: 49

Asn Glu Asp Arg Arg Ser Ala Ser Leu His
1               5                   10

<210> SEQ ID NO 50
<211> LENGTH: 10
<212> TYPE: PRT
<213> ORGANISM: Homo sapiens

<400> SEQUENCE: 50

Leu Pro Lys Leu Ser Ile Thr Gly Thr Tyr
1               5                   10

<210> SEQ ID NO 51
<211> LENGTH: 10
<212> TYPE: PRT
<213> ORGANISM: Homo sapiens

<400> SEQUENCE: 51

Asp Leu Lys Ser Val Leu Gly Gln Leu Gly
1               5                   10

<210> SEQ ID NO 52
<211> LENGTH: 10
<212> TYPE: PRT
<213> ORGANISM: Homo sapiens

<400> SEQUENCE: 52

Ile Thr Lys Val Phe Ser Asn Gly Ala Asp
1               5                   10

<210> SEQ ID NO 53
<211> LENGTH: 10
<212> TYPE: PRT
<213> ORGANISM: Homo sapiens

<400> SEQUENCE: 53

Leu Ser Gly Val Thr Glu Glu Ala Pro Leu
1               5                   10

<210> SEQ ID NO 54
<211> LENGTH: 10
<212> TYPE: PRT
<213> ORGANISM: Homo sapiens

<400> SEQUENCE: 54

Lys Leu Ser Lys Ala Val His Lys Ala Val
1               5                   10

<210> SEQ ID NO 55
<211> LENGTH: 10
<212> TYPE: PRT
<213> ORGANISM: Homo sapiens

<400> SEQUENCE: 55

Leu Thr Ile Asp Glu Lys Gly Thr Glu Ala
1               5                   10

<210> SEQ ID NO 56
<211> LENGTH: 10
<212> TYPE: PRT
<213> ORGANISM: Homo sapiens

```
<400> SEQUENCE: 56

Ala Gly Ala Met Phe Leu Glu Ala Ile Pro
1               5                   10

<210> SEQ ID NO 57
<211> LENGTH: 10
<212> TYPE: PRT
<213> ORGANISM: Homo sapiens

<400> SEQUENCE: 57

Met Ser Ile Pro Pro Glu Val Lys Phe Asn
1               5                   10

<210> SEQ ID NO 58
<211> LENGTH: 10
<212> TYPE: PRT
<213> ORGANISM: Homo sapiens

<400> SEQUENCE: 58

Lys Pro Phe Val Phe Leu Met Ile Glu Gln
1               5                   10

<210> SEQ ID NO 59
<211> LENGTH: 10
<212> TYPE: PRT
<213> ORGANISM: Homo sapiens

<400> SEQUENCE: 59

Asn Thr Lys Ser Pro Leu Phe Met Gly Lys
1               5                   10

<210> SEQ ID NO 60
<211> LENGTH: 7
<212> TYPE: PRT
<213> ORGANISM: Homo sapiens

<400> SEQUENCE: 60

Val Val Asn Pro Thr Gln Lys
1               5

<210> SEQ ID NO 61
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: native sequence

<400> SEQUENCE: 61

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95
```

-continued

```
Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 62
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: novel sequence
<220> FEATURE:
<221> NAME/KEY: MISC_FEATURE
<222> LOCATION: (356)..(357)
<223> OTHER INFORMATION: Xaa = any amino acid

<400> SEQUENCE: 62

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30
```

```
Phe Ala Phe Ser Leu Tyr Arg Gln Leu Ala His Gln Ser Asn Ser Thr
         35                  40                  45

Asn Ile Phe Phe Ser Pro Val Ser Ile Ala Thr Ala Phe Ala Met Leu
     50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Glu Ala Gln Ile His Glu Gly Phe
                 85                  90                  95

Gln Glu Leu Leu Arg Thr Leu Asn Gln Pro Asp Ser Gln Leu Gln Leu
             100                 105                 110

Thr Thr Gly Asn Gly Leu Phe Leu Ser Glu Gly Leu Lys Leu Val Asp
         115                 120                 125

Lys Phe Leu Glu Asp Val Lys Lys Leu Tyr His Ser Glu Ala Phe Thr
130                 135                 140

Val Asn Phe Gly Asp His Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
             180                 185                 190

Lys Trp Glu Arg Pro Phe Glu Val Lys Asp Thr Glu Asp Glu Asp Phe
         195                 200                 205

His Val Asp Gln Val Thr Thr Val Lys Val Pro Met Met Lys Arg Leu
     210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
             260                 265                 270

Thr Lys Phe Leu Glu Asn Glu Asp Arg Arg Ser Ala Ser Leu His Leu
         275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
             340                 345                 350

Leu Glu Arg Xaa Xaa Arg Ser Ile Pro Pro Glu Val Lys Phe Asn Lys
         355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 63
<211> LENGTH: 417
<212> TYPE: PRT
<213> ORGANISM: Homo sapiens

<400> SEQUENCE: 63

Met Pro Ser Ser Val Ser Trp Gly Ile Leu Leu Ala Gly Leu Cys Cys
 1               5                  10                  15
```

```
Leu Val Pro Val Ser Leu Ala Glu Asp Pro Gln Gly Asp Ala Ala Gln
         20                  25                  30

Lys Thr Asp Thr Ser His His Asp Gln Asp His Pro Thr Phe Asn Lys
         35                  40                  45

Ile Thr Pro Asn Leu Ala Glu Phe Ala Phe Ser Leu Tyr Arg Gln Leu
 50                  55                  60

Ala His Gln Ser Asn Ser Thr Asn Ile Phe Phe Ser Pro Val Ser Ile
 65                  70                  75                  80

Ala Thr Ala Phe Ala Asn Leu Ser Leu Gly Thr Lys Ala Asp Thr His
                 85                  90                  95

Asp Glu Ile Leu Glu Gly Leu Asn Phe Asn Leu Thr Glu Ile Pro Glu
            100                 105                 110

Ala Gln Ile His Glu Gly Phe Gln Glu Leu Leu Arg Thr Leu Asn Gln
            115                 120                 125

Pro Asp Ser Gln Leu Gln Leu Thr Thr Gly Asn Gly Leu Phe Leu Ser
130                 135                 140

Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Glu Lys Gly Thr Gln Gly Lys Ile
            180                 185                 190

Val Asp Leu Val Lys Glu Leu Asp Arg Asp Thr Val Phe Ala Leu Val
            195                 200                 205

Asn Tyr Ile Phe Phe Lys Gly Lys Trp Glu Arg Pro Phe Glu Val Lys
210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
            275                 280                 285

Glu Leu Thr His Asp Ile Ile Thr Lys Phe Leu Glu Asn Glu Asp Arg
290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
            355                 360                 365

Glu Ala Ala Gly Ala Met Phe Leu Glu Ala Ile Pro Met Ser Ile Pro
370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
                405                 410                 415

Lys
```

<210> SEQ ID NO 64
<211> LENGTH: 699
<212> TYPE: DNA
<213> ORGANISM: Artificial Sequence
<220> FEATURE:
<223> OTHER INFORMATION: derived from IgG1, FC

<400> SEQUENCE: 64

```
gagcccaaat cttgtgacaa aactcacaca tgcccaccgt gcccagcacc tgaactcctg      60
gggggaccgt cagtcttcct cttccccccca aaacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga caactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga gagcctctc cctgtctccg ggtaaatga                            699
```

<210> SEQ ID NO 65
<211> LENGTH: 232
<212> TYPE: PRT
<213> ORGANISM: Artificial Sequence
<220> FEATURE:
<223> OTHER INFORMATION: derived from IgG1, Fc

<400> SEQUENCE: 65

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 66
<211> LENGTH: 1257
<212> TYPE: DNA
<213> ORGANISM: Human AAT

<400> SEQUENCE: 66
atgccgtctt ctgtctcgtg gggcatcctc ctgctggcag gcctgtgctg cctggtccct     60
gtctccctgg ctgaggatcc ccagggagat gctgcccaga agacagatac atcccaccac    120
gatcaggatc acccaacctt caacaagatc acccccaacc tggctgagtt cgccttcagc    180
ctataccgcc agctggcaca ccagtccaac agcaccaata tcttcttctc cccagtgagc    240
atcgctacag ccttttgcaat gctctccctg ggaccaagg ctgacactca cgatgaaatc    300
ctggagggcc tgaatttcaa cctcacggag attccgagg ctcagatcca tgaaggcttc    360
caggaactcc tccgtaccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagttttgc tctggtgaat acatcttct ttaaaggcaa atgggagaga    660
ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gagcgtcct gggtcaactg gcatcacta aggtcttcag caatggggct   1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccga ggtcaagttc aacaaaccct tgtcttctt aatgattgaa   1200 caaaatacca gtctcccct cttcatggga aagtggtga atcccaccca aaaatga       1257

<210> SEQ ID NO 67
<211> LENGTH: 418
<212> TYPE: PRT
<213> ORGANISM: Human AAT

<400> SEQUENCE: 67

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

```
Leu Ala His Gln Ser Asn Ser Thr Asn Ile Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```

<210> SEQ ID NO 68
<211> LENGTH: 1185
<212> TYPE: DNA
<213> ORGANISM: Human AAT

<400> SEQUENCE: 68

```
gaggatcccc agggagatgc tgcccagaag acagatacat cccaccacga tcaggatcac      60
ccaaccttca acaagatcac ccccaacctg gctgagttcg ccttcagcct ataccgccag     120
```

```
ctggcacacc agtccaacag caccaatatc ttcttctccc cagtgagcat cgctacagcc      180
tttgcaatgc tctccctggg gaccaaggct gacactcacg atgaaatcct ggagggcctg      240
aatttcaacc tcacggagat tccggaggct cagatccatg aaggcttcca ggaactcctc      300
cgtaccctca accagccaga cagccagctc cagctgacca ccggcaatgg cctgttcctc      360
agcgagggcc tgaagctagt ggataagttt ttggaggatg ttaaaaagtt gtaccactca      420
gaagccttca ctgtcaactt cggggacacc gaagaggcca gaaacagat caacgattac      480 gtggagaagg gtactcaagg gaaaattgtg gatttggtca aggagcttga cagagacaca      540
gttttgtctc tggtgaatta catcttcttt aaaggcaaat gggagagacc ctttgaagtc      600
aaggacaccg aggaagagga cttccacgtg gaccaggtga ccaccgtgaa ggtgcctatg      660
atgaagcgtt taggcatgtt taacatccag cactgtaaga gctgtccag ctgggtgctg      720 ctgatgaaat acctgggcaa tgccaccgcc atcttcttcc tgcctgatga ggggaaacta      780
cagcacctgg aaaatgaact cacccacgat atcatcacca agttcctgga aaatgaagac      840
agaaggtctg ccagcttaca tttacccaaa ctgtccatta ctggaaccta tgatctgaag      900
agcgtcctgg gtcaactggg catcactaag gtcttcagca tggggctga cctctccggg      960 gtcacagagg aggcacccct gaagctctcc aaggccgtgc ataaggctgt gctgaccatc     1020
gacgagaaag ggactgaagc tgctgggggcc atgttttag aggccatacc catgtctatc     1080 cccccgagg tcaagttcaa caaccccttt gtcttcttaa tgattgaaca aaataccaag     1140
tctcccctct tcatgggaaa agtggtgaat cccacccaaa aatga                     1185
```

<210> SEQ ID NO 69
<211> LENGTH: 394
<212> TYPE: PRT
<213> ORGANISM: Human AAT

<400> SEQUENCE: 69

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
```

```
            180                 185                 190
Lys Trp Glu Arg Pro Phe Glu Val Lys Asp Thr Glu Glu Asp Phe
            195                 200                 205
His Val Asp Gln Val Thr Thr Val Lys Val Pro Met Met Lys Arg Leu
            210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
            275                 280                 285
Pro Lys Leu Ser Ile Thr Gly Thr Tyr Asp Leu Lys Ser Val Leu Gly
            290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
            355                 360                 365
Pro Phe Val Phe Leu Met Ile Glu Gln Asn Thr Lys Ser Pro Leu Phe
            370                 375                 380
Met Gly Lys Val Val Asn Pro Thr Gln Lys
385                 390

<210> SEQ ID NO 70
<211> LENGTH: 1959
<212> TYPE: DNA
<213> ORGANISM: Artificial Sequence
<220> FEATURE:
<223> OTHER INFORMATION: AAT-FC

<400> SEQUENCE: 70
atgccgtctt ctgtctcgtg gggcatcctc ctgctggcag gcctgtgctg cctggtccct      60
gtctccctgg ctgaggatcc ccagggagat gctgcccaga gacagatac atcccaccac     120
gatcaggatc acccaacctt caacaagatc accccaacct ggctgagtt cgccttcagc     180
ctataccgcc agctggcaca ccagtccaac agcaccaata tcttcttctc cccagtgagc    240
atcgctacag cctttgcaat gctctccctg ggaccaagg ctgacactca cgatgaaatc     300
ctggagggcc tgaatttcaa cctcacggag attccggagg ctcagatcca tgaaggcttc    360
caggaactcc tccgtaccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagtttttgc tctggtgaat tacatcttct ttaaaggcaa atggagaga     660
ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
```

```
gagggggaaac tacagcacct ggaaaatgaa ctcacccacg atatcatcac caagttcctg    900
gaaaatgaag acagaaggtc tgccagctta catttaccca aactgtccat tactggaacc    960
tatgatctga agagcgtcct gggtcaactg ggcatcacta aggtcttcag caatggggct   1020
gacctctccg gggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccccga ggtcaagttc aacaaaccct ttgtcttctt aatgattgaa   1200
caaaatacca gtctccccct cttcatggga aaagtggtga atcccaccca aaaaacgcgt   1260
gagcccaaat cttgtgacaa aactcacaca tgcccaccgt gcccagcacc tgaactcctg   1320
gggggaccgt cagtcttcct cttccccccca aaacccaagg acaccctcat gatctcccgg   1380 accctgagg tcacatgcgt ggtggtggac gtgagccacg aagaccctga ggtcaagttc   1440
aactggtacg tggacggcgt ggaggtgcat aatgccaaga caaagccgcg ggaggagcag   1500
tacaacagca cgtaccgtgt ggtcagcgtc ctcaccgtcc tgcaccagga ctggctgaat   1560
ggcaaggagt acaagtgcaa ggtctccaac aaagccctcc cagcccccat cgagaaaacc   1620
atctccaaag ccaaagggca gccccgagaa ccacaggtgt acaccctgcc cccatcccgg   1680
gatgagctga ccaagaacca ggtcagcctg acctgcctgg tcaaaggctt ctatcccagc   1740
gacatcgccg tggagtggga gagcaatggg cagccggaga acaactacaa gaccacgcct   1800
cccgtgctgg actccgacgg ctccttcttc ctctacagca agctcaccgt ggacaagagc   1860
aggtggcagc aggggaacgt cttctcatgc tccgtgatgc atgaggctct gcacaaccac   1920
tacacgcaga agagcctctc cctgtctccg ggtaaatga                          1959
```

<210> SEQ ID NO 71
<211> LENGTH: 652
<212> TYPE: PRT
<213> ORGANISM: Artificial Sequence
<220> FEATURE:
<223> OTHER INFORMATION: AAT-Fc

<400> SEQUENCE: 71

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
```

```
            165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
    210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
                260                 265                 270
Thr Ala Ile Phe Phe Leu Pro Asp Glu Gly Lys Leu Gln His Leu Glu
                275                 280                 285
Asn Glu Leu Thr His Asp Ile Ile Thr Lys Phe Leu Glu Asn Glu Asp
            290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Thr Arg Glu Pro Lys Ser Cys Asp Lys Thr His Thr Cys Pro
                420                 425                 430
Pro Cys Pro Ala Pro Glu Leu Leu Gly Gly Pro Ser Val Phe Leu Phe
            435                 440                 445
Pro Pro Lys Pro Lys Asp Thr Leu Met Ile Ser Arg Thr Pro Glu Val
            450                 455                 460
Thr Cys Val Val Val Asp Val Ser His Glu Asp Pro Glu Val Lys Phe
465                 470                 475                 480
Asn Trp Tyr Val Asp Gly Val Glu Val His Asn Ala Lys Thr Lys Pro
                485                 490                 495
Arg Glu Glu Gln Tyr Asn Ser Thr Tyr Arg Val Val Ser Val Leu Thr
                500                 505                 510
Val Leu His Gln Asp Trp Leu Asn Gly Lys Glu Tyr Lys Cys Lys Val
            515                 520                 525
Ser Asn Lys Ala Leu Pro Ala Pro Ile Glu Lys Thr Ile Ser Lys Ala
            530                 535                 540
Lys Gly Gln Pro Arg Glu Pro Gln Val Tyr Thr Leu Pro Pro Ser Arg
545                 550                 555                 560
Asp Glu Leu Thr Lys Asn Gln Val Ser Leu Thr Cys Leu Val Lys Gly
                565                 570                 575
Phe Tyr Pro Ser Asp Ile Ala Val Glu Trp Glu Ser Asn Gly Gln Pro
            580                 585                 590
```

Glu Asn Asn Tyr Lys Thr Thr Pro Pro Val Leu Asp Ser Asp Gly Ser
            595                 600                 605

Phe Phe Leu Tyr Ser Lys Leu Thr Val Asp Lys Ser Arg Trp Gln Gln
        610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
            645                 650

<210> SEQ ID NO 72
<211> LENGTH: 1953
<212> TYPE: DNA
<213> ORGANISM: Artificial Sequence
<220> FEATURE:
<223> OTHER INFORMATION: AAT-Fc

<400> SEQUENCE: 72

| | | | |
|---|---|---|---|
| atgccgtctt ctgtctcgtg gggcatcctc ctgctggcag gcctgtgctg cctggtccct | | | 60 |
| gtctccctgg ctgaggatcc ccagggagat gctgcccaga agacagatac atcccaccac | | | 120 |
| gatcaggatc acccaacctt caacaagatc accccccaacc tggctgagtt cgccttcagc | | | 180 |
| ctataccgcc agctggcaca ccagtccaac agcaccaata tcttcttctc cccagtgagc | | | 240 |
| atcgctacag cctttgcaat gctctccctg gggaccaagg ctgacactca cgatgaaatc | | | 300 |
| ctggagggcc tgaatttcaa cctcacggag attccggagg ctcagatcca tgaaggcttc | | | 360 |
| caggaactcc tccgtaccct caaccagcca gacagccagc tccagctgac caccggcaat | | | 420 |
| ggcctgttcc tcagcgaggg cctgaagcta gtggataagt ttttggagga tgttaaaaag | | | 480 |
| ttgtaccact cagaagcctt cactgtcaac ttcggggaca ccgaagaggc caagaaacag | | | 540 |
| atcaacgatt acgtggagaa gggtactcaa gggaaaattg tggatttggt caaggagctt | | | 600 |
| gacagagaca cagttttgc tctggtgaat tacatcttct ttaaaggcaa atggagaga | | | 660 |
| ccctttgaag tcaaggacac cgaggaagag gacttccacg tggaccaggt gaccaccgtg | | | 720 |
| aaggtgccta tgatgaagcg tttaggcatg tttaacatcc agcactgtaa gaagctgtcc | | | 780 |
| agctgggtgc tgctgatgaa atacctgggc aatgccaccg ccatcttctt cctgcctgat | | | 840 |
| gaggggaaac tacagcacct ggaaaatgaa ctcacccacg atatcatcac caagttcctg | | | 900 |
| gaaaatgaag acagaaggtc tgccagctta catttaccca actgtccat tactggaacc | | | 960 |
| tatgatctga gagcgtcct gggtcaactg gcatcacta aggtcttcag caatggggct | | | 1020 |
| gacctctccg gggtcacaga ggaggcaccc ctgaagctct ccaaggccgt gcataaggct | | | 1080 |
| gtgctgacca tcgacgagaa agggactgaa gctgctgggg ccatgttttt agaggccata | | | 1140 |
| cccatgtcta tccccccga ggtcaagttc aacaaaccct tgtcttctt aatgattgaa | | | 1200 |
| caaaatacca gtctccctt cttcatggga aagtggtga atcccaccca aaaagagccc | | | 1260 |
| aaatcttgtg acaaaactca cacatgccca ccgtgcccag cacctgaact cctgggggga | | | 1320 |
| ccgtcagtct tcctcttccc cccaaaaccc aaggacaccc tcatgatctc ccggacccct | | | 1380 |
| gaggtcacat gcgtggtggt ggacgtgagc cacgaagacc ctgaggtcaa gttcaactgg | | | 1440 |
| tacgtggacg gcgtggaggt gcataatgcc aagacaaagc cgcggggga gcagtacaac | | | 1500 |
| agcacgtacc gtgtggtcag cgtcctcacc gtcctgcacc aggactggct gaatggcaag | | | 1560 |
| gagtacaagt gcaaggtctc caacaaagcc ctcccagccc ccatcgagaa aaccatctcc | | | 1620 |
| aaagccaaag ggcagccccg agaaccacag gtgtacaccc tgcccccatc ccgggatgag | | | 1680 |

-continued

```
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacacg    1920
cagaagagcc tctccctgtc tccgggtaaa tga                                 1953
```

<210> SEQ ID NO 73
<211> LENGTH: 650
<212> TYPE: PRT
<213> ORGANISM: Artificial Sequence
<220> FEATURE:
<223> OTHER INFORMATION: AAT-Fc

<400> SEQUENCE: 73

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320
```

```
Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Glu Pro Lys Ser Cys Asp Lys Thr His Thr Cys Pro Pro Cys
            420                 425                 430

Pro Ala Pro Glu Leu Leu Gly Gly Pro Ser Val Phe Leu Phe Pro Pro
    435                 440                 445

Lys Pro Lys Asp Thr Leu Met Ile Ser Arg Thr Pro Glu Val Thr Cys
450                 455                 460

Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
                485                 490                 495

Glu Gln Tyr Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
        515                 520                 525

Lys Ala Leu Pro Ala Pro Ile Glu Lys Thr Ile Ser Lys Ala Lys Gly
    530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Lys Leu Thr Val Asp Lys Ser Arg Trp Gln Gln Gly Asn
    610                 615                 620

Val Phe Ser Cys Ser Val Met His Glu Ala Leu His Asn His Tyr Thr
625                 630                 635                 640

Gln Lys Ser Leu Ser Leu Ser Pro Gly Lys
                645                 650

<210> SEQ ID NO 74
<211> LENGTH: 1881
<212> TYPE: DNA
<213> ORGANISM: Artificial Sequence
<220> FEATURE:
<223> OTHER INFORMATION: AAT-Fc

<400> SEQUENCE: 74
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
```

```
tttgcaatgc tctccctggg gaccaaggct gacactcacg atgaaatcct ggagggcctg      240
aatttcaacc tcacggagat tccggaggct cagatccatg aaggcttcca ggaactcctc      300
cgtaccctca accagccaga cagccagctc cagctgacca ccggcaatgg cctgttcctc      360
agcgagggcc tgaagctagt ggataagttt ttggaggatg ttaaaaagtt gtaccactca      420
gaagccttca ctgtcaactt cggggacacc gaagaggcca agaaacagat caacgattac      480
gtggagaagg gtactcaagg gaaaattgtg gatttggtca aggagcttga cagagacaca      540 gttttttgctc tggtgaatta catcttcttt aaaggcaaat gggagagacc ctttgaagtc      600
aaggacaccg aggaagagga cttccacgtg accaggtga ccaccgtgaa ggtgcctatg      660
atgaagcgtt taggcatgtt taacatccag cactgtaaga agctgtccag ctgggtgctg      720
ctgatgaaat acctgggcaa tgccaccgcc atcttcttcc tgcctgatga ggggaaacta      780
cagcacctgg aaaatgaact cacccacgat atcatcacca agttcctgga aaatgaagac      840
agaaggtctg ccagcttaca tttacccaaa ctgtccatta ctggaaccta tgatctgaag      900
agcgtcctgg gtcaactggg catcactaag gtcttcagca atggggctga cctctccggg      960
gtcacagagg aggcaccccct gaagctctcc aaggccgtgc ataaggctgt gctgaccatc     1020
gacgagaaag ggactgaagc tgctggggcc atgtttttag aggccatacc catgtctatc     1080
ccccccgagg tcaagttcaa caaaccctt gtcttcttaa tgattgaaca aaataccaag     1140
tctcccctct tcatgggaaa agtggtgaat cccacccaaa aagagcccaa atcttgtgac     1200
aaaactcaca catgcccacc gtgcccagca cctgaactcc tggggggacc gtcagtcttc     1260
ctcttccccc caaaacccaa ggacaccctc atgatctccc ggacccctga ggtcacatgc     1320
gtggtggtgg acgtgagcca cgaagaccct gaggtcaagt tcaactggta cgtggacggc     1380
gtggaggtgc ataatgccaa gacaaagccg cgggaggagc agtacaacag cacgtaccgt     1440
gtggtcagcg tcctcaccgt cctgcaccag gactggctga atggcaagga gtacaagtgc     1500
aaggtctcca acaaagccct cccagccccc atcgagaaaa ccatctccaa agccaaaggg     1560
cagccccgag aaccacaggt gtacaccctg cccccatccc gggatgagct gaccaagaac     1620
caggtcagcc tgacctgcct ggtcaaaggc ttctatccca gcgacatcgc cgtggagtgg     1680
gagagcaatg ggcagccgga gaacaactac aagaccacgc ctcccgtgct ggactccgac     1740
ggctccttct tcctctacag caagctcacc gtggacaaga gcaggtggca gcaggggaac     1800
gtcttctcat gctccgtgat gcatgaggct ctgcacaacc actacacgca gaagagcctc     1860
tccctgtctc cgggtaaatg a                                                1881
```

<210> SEQ ID NO 75
<211> LENGTH: 626
<212> TYPE: PRT
<213> ORGANISM: Artificial Sequence
<220> FEATURE:
<223> OTHER INFORMATION: AAT-Fc

<400> SEQUENCE: 75

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu

```
                50             55              60
Ser Leu Gly Thr Lys Ala Asp Thr His Asp Glu Ile Leu Glu Gly Leu
 65              70              75              80

Asn Phe Asn Leu Thr Glu Ile Pro Glu Ala Gln Ile His Glu Gly Phe
                 85              90              95

Gln Glu Leu Leu Arg Thr Leu Asn Gln Pro Asp Ser Gln Leu Gln Leu
                100             105             110

Thr Thr Gly Asn Gly Leu Phe Leu Ser Glu Gly Leu Lys Leu Val Asp
                115             120             125

Lys Phe Leu Glu Asp Val Lys Lys Leu Tyr His Ser Glu Ala Phe Thr
    130             135             140

Val Asn Phe Gly Asp Thr Glu Glu Ala Lys Lys Gln Ile Asn Asp Tyr
145             150             155             160

Val Glu Lys Gly Thr Gln Gly Lys Ile Val Asp Leu Val Lys Glu Leu
                165             170             175

Asp Arg Asp Thr Val Phe Ala Leu Val Asn Tyr Ile Phe Phe Lys Gly
                180             185             190

Lys Trp Glu Arg Pro Phe Glu Val Lys Asp Thr Glu Glu Glu Asp Phe
    195             200             205

His Val Asp Gln Val Thr Thr Val Lys Val Pro Met Met Lys Arg Leu
    210             215             220

Gly Met Phe Asn Ile Gln His Cys Lys Lys Leu Ser Ser Trp Val Leu
225             230             235             240

Leu Met Lys Tyr Leu Gly Asn Ala Thr Ala Ile Phe Phe Leu Pro Asp
                245             250             255

Glu Gly Lys Leu Gln His Leu Glu Asn Glu Leu Thr His Asp Ile Ile
                260             265             270

Thr Lys Phe Leu Glu Asn Glu Asp Arg Arg Ser Ala Ser Leu His Leu
    275             280             285

Pro Lys Leu Ser Ile Thr Gly Thr Tyr Asp Leu Lys Ser Val Leu Gly
    290             295             300

Gln Leu Gly Ile Thr Lys Val Phe Ser Asn Gly Ala Asp Leu Ser Gly
305             310             315             320

Val Thr Glu Glu Ala Pro Leu Lys Leu Ser Lys Ala Val His Lys Ala
                325             330             335

Val Leu Thr Ile Asp Glu Lys Gly Thr Glu Ala Ala Gly Ala Met Phe
                340             345             350

Leu Glu Ala Ile Pro Met Ser Ile Pro Pro Glu Val Lys Phe Asn Lys
    355             360             365

Pro Phe Val Phe Leu Met Ile Glu Gln Asn Thr Lys Ser Pro Leu Phe
    370             375             380

Met Gly Lys Val Val Asn Pro Thr Gln Lys Glu Pro Lys Ser Cys Asp
385             390             395             400

Lys Thr His Thr Cys Pro Pro Cys Pro Ala Pro Glu Leu Leu Gly Gly
                405             410             415

Pro Ser Val Phe Leu Phe Pro Pro Lys Pro Lys Asp Thr Leu Met Ile
                420             425             430

Ser Arg Thr Pro Glu Val Thr Cys Val Val Val Asp Val Ser His Glu
    435             440             445

Asp Pro Glu Val Lys Phe Asn Trp Tyr Val Asp Gly Val Glu Val His
    450             455             460

Asn Ala Lys Thr Lys Pro Arg Glu Glu Gln Tyr Asn Ser Thr Tyr Arg
465             470             475             480
```

```
Val Val Ser Val Leu Thr Val Leu His Gln Asp Trp Leu Asn Gly Lys
            485                 490                 495

Glu Tyr Lys Cys Lys Val Ser Asn Lys Ala Leu Pro Ala Pro Ile Glu
        500                 505                 510

Lys Thr Ile Ser Lys Ala Lys Gly Gln Pro Arg Glu Pro Gln Val Tyr
            515                 520                 525

Thr Leu Pro Pro Ser Arg Asp Glu Leu Thr Lys Asn Gln Val Ser Leu
        530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
                565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
        595                 600                 605

Glu Ala Leu His Asn His Tyr Thr Gln Lys Ser Leu Ser Leu Ser Pro
    610                 615                 620

Gly Lys
625

<210> SEQ ID NO 76
<211> LENGTH: 1257
<212> TYPE: DNA
<213> ORGANISM: Human AAT

<400> SEQUENCE: 76
atgccgtctt ctgtctcgtg gggcatcctc ctgctggcag gcctgtgctg cctggtccct    60
gtctccctgg ctgaggatcc ccagggagat gctgcccaga gacagatac atcccaccac   120 gatcaggatc acccaacctt caacaagatc acccccaacc tggctgagtt cgccttcagc   180
ctataccgcc agctggcaca ccagtccaac agcaccaata tcttcttctc cccagtgagc   240
atcgctacag cctttgcaat gctctccctg ggaccaagg ctgacactca cgatgaaatc    300
ctggagggcc tgaatttcaa cctcacggag attccggagg ctcagatcca tgaaggcttc   360
caggaactcc tccgtaccct caaccagcca gacagccagc tccagctgac accggcaat    420 ggcctgttcc tcagcgaggg cctgaagcta gtggataagt ttttggagga tgttaaaaag   480
ttgtaccact cagaagcctt cactgtcaac ttcggggaca ccgaagaggc caagaaacag   540
atcaacgatt acgtggagaa gggtactcaa gggaaaattg tggatttggt caaggagctt   600
gacagagaca cagttttgc tctggtgaat tacatcttct ttaaaggcaa atgggagaga   660 cccttgaag tcaaggacac cgaggaagag acttccacg tggaccaggc gaccaccgtg     720
aaggtgccta tgatgaagcg tttaggcatg tttaacatcc agcactgtaa gaagctgtcc   780
agctgggtgc tgctgatgaa ataccctggg aatgccaccg ccatcttctt cctgcctgat   840
gaggggaaac tacagcacct ggaaaatgaa ctcacccacg atatcatcac caagttcctg   900
gaaaatgaag acagaaggtc tgccagctta catttaccca aactgtccat tactggaacc   960
tatgatctga gagcgtcct gggtcaactg gcatcacta ggtcttcag caatggggct    1020 gacctctccg ggtcacaga ggaggcaccc ctgaagctct ccaaggccgt gcataaggct   1080
gtgctgacca tcgacgagaa agggactgaa gctgctgggg ccatgttttt agaggccata   1140
cccatgtcta tccccccccga ggtcaagttc aacaaaccct tgtcttctt aatgattgaa   1200
```
caaaatacca agtctcccct cttcatggga aaagtggtga atcccaccca aaaatga          1257

<210> SEQ ID NO 77
<211> LENGTH: 418
<212> TYPE: PRT
<213> ORGANISM: Human AAT

<400> SEQUENCE: 77

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365
```

```
Thr Glu Ala Ala Gly Ala Met Phe Leu Glu Ala Ile Pro Met Ser Ile
370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
        405                 410                 415
Gln Lys
```

<210> SEQ ID NO 78
<211> LENGTH: 1185
<212> TYPE: DNA
<213> ORGANISM: Human AAT

<400> SEQUENCE: 78

| | | | | | |
|---|---|---|---|---|---|
| gaggatcccc | agggagatgc | tgcccagaag | acagatacat | cccaccacga | tcaggatcac | 60 |
| ccaaccttca | acaagatcac | ccccaacctg | gctgagttcg | ccttcagcct | ataccgccag | 120 |
| ctggcacacc | agtccaacag | caccaatatc | ttcttctccc | cagtgagcat | cgctacagcc | 180 |
| tttgcaatgc | tctccctggg | gaccaaggct | gacactcacg | atgaaatcct | ggagggcctg | 240 |
| aatttcaacc | tcacggagat | tccggaggct | cagatccatg | aaggcttcca | ggaactcctc | 300 |
| cgtaccctca | accagccaga | cagccagctc | cagctgacca | ccggcaatgg | cctgttcctc | 360 |
| agcgagggcc | tgaagctagt | ggataagttt | ttggaggatg | ttaaaaagtt | gtaccactca | 420 |
| gaagccttca | ctgtcaactt | cggggacacc | gaagaggcca | agaaacagat | caacgattac | 480 |
| gtggagaagg | gtactcaagg | gaaaattgtg | gatttggtca | aggagcttga | cagagacaca | 540 |
| gttttgctc | tggtgaatta | catcttcttt | aaaggcaaat | gggagagacc | ctttgaagtc | 600 |
| aaggacaccg | aggaagagga | cttccacgtg | gaccaggcga | ccaccgtgaa | ggtgcctatg | 660 |
| atgaagcgtt | taggcatgtt | taacatccag | cactgtaaga | agctgtccag | ctgggtgctg | 720 |
| ctgatgaaat | acctgggcaa | tgccaccgcc | atcttcttcc | tgcctgatga | ggggaaacta | 780 |
| cagcacctgg | aaaatgaact | cacccacgat | atcatcacca | gttcctgga | aaatgaagac | 840 |
| agaaggtctg | ccagcttaca | tttacccaaa | ctgtccatta | ctggaaccta | tgatctgaag | 900 |
| agcgtcctgg | gtcaactggg | catcactaag | gtcttcagca | atgggctga | cctctccggg | 960 |
| gtcacagagg | aggcaccct | gaagctctcc | aaggccgtgc | ataaggctgt | gctgaccatc | 1020 |
| gacgagaaag | ggactgaagc | tgctggggcc | atgttttag | aggccatacc | catgtctatc | 1080 |
| cccccgagg | tcaagttcaa | caaaccctt | gtcttcttaa | tgattgaaca | aaataccaag | 1140 |
| tctcccctct | tcatgggaaa | agtggtgaat | cccacccaaa | aatga | | 1185 |

<210> SEQ ID NO 79
<211> LENGTH: 394
<212> TYPE: PRT
<213> ORGANISM: Human AAT

<400> SEQUENCE: 79

```
Glu Asp Pro Gln Gly Asp Ala Ala Gln Lys Thr Asp Thr Ser His His
1               5                   10                  15
Asp Gln Asp His Pro Thr Phe Asn Lys Ile Thr Pro Asn Leu Ala Glu
            20                  25                  30
Phe Ala Phe Ser Leu Tyr Arg Gln Leu Ala His Gln Ser Asn Ser Thr
        35                  40                  45
Asn Ile Phe Phe Ser Pro Val Ser Ile Ala Thr Ala Phe Ala Met Leu
    50                  55                  60
```

| | | | | | | | | | | | | | | |
|---|---|---|---|---|---|---|---|---|---|---|---|---|---|---|
|Ser|Leu|Gly|Thr|Lys|Ala|Asp|Thr|His|Asp|Glu|Ile|Leu|Glu|Gly|Leu|
|65| | | | |70| | | |75| | | | |80|

Asn Phe Asn Leu Thr Glu Ile Pro Glu Ala Gln Ile His Glu Gly Phe
              85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Ala Thr Thr Val Lys Val Pro Met Met Lys Arg Leu
            210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 80
<211> LENGTH: 1959
<212> TYPE: DNA
<213> ORGANISM: Artificial Sequence
<220> FEATURE:
<223> OTHER INFORMATION: AAT-Fc

<400> SEQUENCE: 80
atgccgtctt ctgtctcgtg gggcatcctc ctgctggcag gcctgtgctg cctggtccct    60
gtctccctgg ctgaggatcc ccagggagat gctgcccaga agacagatac atcccaccac   120
gatcaggatc acccaacctt caacaagatc acccccaacc tggctgagtt cgccttcagc   180

```
ctataccgcc agctggcaca ccagtccaac agcaccaata tcttcttctc cccagtgagc        240
atcgctacag cctttgcaat gctctccctg gggaccaagg ctgacactca cgatgaaatc        300
ctggagggcc tgaatttcaa cctcacggag attccggagg ctcagatcca tgaaggcttc        360
caggaactcc tccgtaccct caaccagcca gacagccagc tccagctgac caccggcaat        420
ggcctgttcc tcagcgaggg cctgaagcta gtggataagt ttttggagga tgttaaaaag        480
ttgtaccact cagaagcctt cactgtcaac ttcggggaca ccgaagaggc caagaaacag        540
atcaacgatt acgtggagaa gggtactcaa gggaaaattg tggatttggt caaggagctt        600
gacagagaca cagttttttgc tctggtgaat tacatcttct ttaaaggcaa atggagaga        660 cccctttgaag tcaaggacac cgaggaagag gacttccacg tggaccaggc gaccaccgtg        720
aaggtgccta tgatgaagcg tttaggcatg tttaacatcc agcactgtaa gaagctgtcc        780
agctgggtgc tgctgatgaa atacctgggc aatgccaccg ccatcttctt cctgcctgat        840
gaggggaaac tacagcacct ggaaaatgaa ctcacccacg atatcatcac caagttcctg        900
gaaaatgaag acagaaggtc tgccagctta catttaccca aactgtccat tactggaacc        960
tatgatctga gagcgtcct gggtcaactg gcatcacta aggtcttcag caatggggct       1020
gacctctccg gggtcacaga ggaggcaccc ctgaagctct ccaaggccgt gcataaggct       1080
gtgctgacca tcgacgagaa agggactgaa gctgctgggg ccatgttttt agaggccata       1140
cccatgtcta tccccccccga ggtcaagttc aacaaaccct tgtcttctt aatgattgaa       1200 caaaatacca agtctcccct cttcatggga aagtggtga atcccaccca aaaacgcgt       1260 gagcccaaat cttgtgacaa aactcacaca tgcccaccgt gcccagcacc tgaactcctg       1320
gggggaccgt cagtcttcct cttccccccca aacccaagg acaccctcat gatctcccgg       1380
acccctgagg tcacatgcgt ggtggtggac gtgagccacg aagaccctga ggtcaagttc       1440
aactggtacg tggacggcgt ggaggtgcat aatgccaaga caaagccgcg ggaggagcag       1500
tacaacagca cgtaccgtgt ggtcagcgtc ctcaccgtcc tgcaccagga ctggctgaat       1560
ggcaaggagt acaagtgcaa ggtctccaac aaagccctcc cagcccccat cgagaaaacc       1620
atctccaaag ccaaagggca gccccgagaa ccacaggtgt acaccctgcc cccatcccgg       1680
gatgagctga ccaagaacca ggtcagcctg acctgcctgg tcaaaggctt ctatcccagc       1740
gacatcgccg tggagtggga gagcaatggg cagccggaga caactacaa gaccacgcct       1800 cccgtgctgg actccgacgg ctccttcttc ctctacagca agctcaccgt ggacaagagc       1860
aggtggcagc aggggaacgt cttctcatgc tccgtgatgc atgaggctct gcacaaccac       1920
tacacgcaga agagcctctc cctgtctccg ggtaaatga                              1959
```

<210> SEQ ID NO 81
<211> LENGTH: 652
<212> TYPE: PRT
<213> ORGANISM: Artificial Sequence
<220> FEATURE:
<223> OTHER INFORMATION: AAT-Fc

<400> SEQUENCE: 81

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

```
Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Glu Pro Lys Ser Cys Asp Lys Thr His Thr Cys Pro
            420                 425                 430

Pro Cys Pro Ala Pro Glu Leu Leu Gly Gly Pro Ser Val Phe Leu Phe
            435                 440                 445

Pro Pro Lys Pro Lys Asp Thr Leu Met Ile Ser Arg Thr Pro Glu Val
450                 455                 460

Thr Cys Val Val Val Asp Val Ser His Glu Asp Pro Glu Val Lys Phe
```

```
               465                 470                 475                 480
Asn Trp Tyr Val Asp Gly Val Glu Val His Asn Ala Lys Thr Lys Pro
                485                 490                 495
Arg Glu Glu Gln Tyr Asn Ser Thr Tyr Arg Val Val Ser Val Leu Thr
                500                 505                 510
Val Leu His Gln Asp Trp Leu Asn Gly Lys Glu Tyr Lys Cys Lys Val
                515                 520                 525
Ser Asn Lys Ala Leu Pro Ala Pro Ile Glu Lys Thr Ile Ser Lys Ala
                530                 535                 540
Lys Gly Gln Pro Arg Glu Pro Gln Val Tyr Thr Leu Pro Pro Ser Arg
545                 550                 555                 560
Asp Glu Leu Thr Lys Asn Gln Val Ser Leu Thr Cys Leu Val Lys Gly
                565                 570                 575
Phe Tyr Pro Ser Asp Ile Ala Val Glu Trp Glu Ser Asn Gly Gln Pro
                580                 585                 590
Glu Asn Asn Tyr Lys Thr Thr Pro Pro Val Leu Asp Ser Asp Gly Ser
                595                 600                 605
Phe Phe Leu Tyr Ser Lys Leu Thr Val Asp Lys Ser Arg Trp Gln Gln
                610                 615                 620
Gly Asn Val Phe Ser Cys Ser Val Met His Glu Ala Leu His Asn His
625                 630                 635                 640
Tyr Thr Gln Lys Ser Leu Ser Leu Ser Pro Gly Lys
                645                 650

<210> SEQ ID NO 82
<211> LENGTH: 1953
<212> TYPE: DNA
<213> ORGANISM: Artificial Sequence
<220> FEATURE:
<223> OTHER INFORMATION: AAT-Fc

<400> SEQUENCE: 82
atgccgtctt ctgtctcgtg gggcatcctc ctgctggcag gcctgtgctg cctggtccct      60
gtctccctgg ctgaggatcc ccagggagat gctgcccaga agacagatac atcccaccac     120
gatcaggatc acccaacctt caacaagatc accccaaccc tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttttgc tctggtgaat tacatcttct ttaaaggcaa atggagagag     660
ccctttgaag tcaaggacac cgaggaagag gacttccacg tggaccaggc gaccaccgtg     720
aaggtgccta tgatgaagcg tttaggcatg tttaacatcc agcactgtaa gaagctgtcc     780
agctgggtgc tgctgatgaa ataccttggc aatgccaccg ccatcttctt cctgcctgat     840
gaggggaaac tacagcacct ggaaaatgaa ctcacccacg atatcatcac caagttcctg     900
gaaaatgaag acagaaggtc tgccagctta catttaccca aactgtccat tactggaacc     960
tatgatctga gagcgtcctg ggtcaactgg gcatcactaa ggtcttcagc aatggggct    1020
```

-continued

```
gacctctccg gggtcacaga ggaggcaccc ctgaagctct ccaaggccgt gcataaggct      1080
gtgctgacca tcgacgagaa agggactgaa gctgctgggg ccatgttttt agaggccata      1140
cccatgtcta tccccccga ggtcaagttc aacaaaccct ttgtcttctt aatgattgaa       1200
caaaatacca agtctcccct cttcatggga aagtggtga atcccaccca aaagagccc        1260 aaatcttgtg acaaaactca cacatgccca ccgtgcccag cacctgaact cctgggggga      1320
ccgtcagtct tcctcttccc cccaaaaccc aaggacaccc tcatgatctc ccggacccct      1380
gaggtcacat gcgtggtggt ggacgtgagc cacgaagacc ctgaggtcaa gttcaactgg      1440
tacgtggacg gcgtggaggt gcataatgcc aagacaaagc cgcgggagga gcagtacaac      1500
agcacgtacc gtgtggtcag cgtcctcacc gtcctgcacc aggactggct gaatggcaag      1560
gagtacaagt gcaaggtctc caacaaagcc ctcccagccc ccatcgagaa aaccatctcc      1620
aaagccaaag ggcagccccg agaaccacag gtgtacaccc tgcccccatc ccgggatgag      1680
ctgaccaaga accaggtcag cctgacctgc ctggtcaaag gcttctatcc cagcgacatc      1740
gccgtggagt gggagagcaa tgggcagccg gagaacaact acaagaccac gcctcccgtg      1800
ctggactccg acggctcctt cttcctctac agcaagctca ccgtggacaa gagcaggtgg      1860
cagcagggga acgtcttctc atgctccgtg atgcatgagg ctctgcacaa ccactacacg      1920
cagaagagcc tctccctgtc tccgggtaaa tga                                   1953
```

<210> SEQ ID NO 83
<211> LENGTH: 650
<212> TYPE: PRT
<213> ORGANISM: Artificial Sequence
<220> FEATURE:
<223> OTHER INFORMATION: AAT-Fc

<400> SEQUENCE: 83

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
```

```
            195                 200                 205
Val Asn Tyr Ile Phe Lys Gly Lys Trp Glu Arg Pro Phe Glu Val
210                 215                 220

Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Glu Pro Lys Ser Cys Asp Lys Thr His Thr Cys Pro Pro Cys
            420                 425                 430

Pro Ala Pro Glu Leu Leu Gly Gly Pro Ser Val Phe Leu Phe Pro Pro
        435                 440                 445

Lys Pro Lys Asp Thr Leu Met Ile Ser Arg Thr Pro Glu Val Thr Cys
450                 455                 460

Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
                485                 490                 495

Glu Gln Tyr Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
        515                 520                 525

Lys Ala Leu Pro Ala Pro Ile Glu Lys Thr Ile Ser Lys Ala Lys Gly
530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Lys Leu Thr Val Asp Lys Ser Arg Trp Gln Gln Gly Asn
610                 615                 620
```

```
Val Phe Ser Cys Ser Val Met His Glu Ala Leu His Asn His Tyr Thr
625                 630                 635                 640

Gln Lys Ser Leu Ser Leu Ser Pro Gly Lys
                645                 650
```

<210> SEQ ID NO 84
<211> LENGTH: 1881
<212> TYPE: DNA
<213> ORGANISM: Artificial Sequence
<220> FEATURE:
<223> OTHER INFORMATION: AAT-Fc

<400> SEQUENCE: 84

```
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
tttgcaatgc tctccctggg gaccaaggct gacactcacg atgaaatcct ggagggcctg     240
aatttcaacc tcacggagat tccggaggct cagatccatg aaggcttcca ggaactcctc     300
cgtaccctca accagccaga cagccagctc cagctgacca ccggcaatgg cctgttcctc     360
agcgagggcc tgaagctagt ggataagttt ttggaggatg ttaaaaagtt gtaccactca     420
gaagccttca ctgtcaactt cggggacacc gaagaggcca gaaacagat caacgattac     480
gtggagaagg gtactcaagg gaaaattgtg gatttggtca aggagcttga cagagacaca     540
gttttttgctc tggtgaatta catcttcttt aaaggcaaat gggagagacc ctttgaagtc     600
aaggacaccg aggaagagga cttccacgtg gaccaggcga ccaccgtgaa ggtgcctatg     660
atgaagcgtt taggcatgtt taacatccag cactgtaaga gctgtccag ctgggtgctg     720
ctgatgaaat acctgggcaa tgccaccgcc atcttcttcc tgcctgatga ggggaaacta     780
cagcacctgg aaaatgaact cacccacgat atcatcacca gttcctgga aaatgaagac     840
agaaggtctg ccagcttaca tttacccaaa ctgtccatta ctggaaccta tgatctgaag     900
agcgtcctgg gtcaactggg catcactaag gtcttcagca atgggctga cctctccggg     960
gtcacagagg aggcacccct gaagctctcc aaggccgtgc ataaggctgt gctgaccatc    1020
gacgagaaag ggactgaagc tgctggggcc atgtttttag aggccatacc catgtctatc    1080
cccccccgagg tcaagttcaa caaacccttt gtcttcttaa tgattgaaca aataccaag    1140
tctccctct tcatgggaaa agtggtgaat cccacccaaa aagagcccaa atcttgtgac    1200
aaaactcaca catgcccacc gtgcccagca cctgaactcc tggggggacc gtcagtcttc    1260
ctcttccccc caaaacccaa ggacaccctc atgatctccc ggaccctga ggtcacatgc    1320
gtggtggtgg acgtgagcca cgaagaccct gaggtcaagt tcaactggta cgtggacggc    1380
gtggaggtgc ataatgccaa gacaaagccg cgggaggagc agtacaacag cacgtaccgt    1440
gtggtcagcg tcctcaccgt cctgcaccag gactggctga atggcaagga gtacaagtgc    1500
aaggtctcca acaaagccct cccagccccc atcgagaaaa ccatctccaa agccaaaggg    1560
cagccccgag aaccacaggt gtacaccctg cccccatccc gggatgagct gaccaagaac    1620
caggtcagcc tgacctgcct ggtcaaaggc ttctatccca gcgacatcgc cgtggagtgg    1680
gagagcaatg ggcagccgga gaacaactac aagaccacgc ctcccgtgct ggactccgac    1740
ggctccttct tcctctacag caagctcacc gtggacaaga gcaggtggca gcaggggaac    1800
gtcttctcat gctccgtgat gcatgaggct ctgcacaacc actacacgca gaagagcctc    1860
```
tccctgtctc cgggtaaatg a                                               1881

<210> SEQ ID NO 85
<211> LENGTH: 626
<212> TYPE: PRT
<213> ORGANISM: Artificial Sequence
<220> FEATURE:
<223> OTHER INFORMATION: AAT-Fc

<400> SEQUENCE: 85

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
```

-continued

```
                355                 360                 365
Pro Phe Val Phe Leu Met Ile Glu Gln Asn Thr Lys Ser Pro Leu Phe
    370                 375                 380
Met Gly Lys Val Val Asn Pro Thr Gln Lys Glu Pro Lys Ser Cys Asp
385                 390                 395                 400
Lys Thr His Thr Cys Pro Pro Cys Pro Ala Pro Glu Leu Leu Gly Gly
                405                 410                 415
Pro Ser Val Phe Leu Phe Pro Pro Lys Pro Lys Asp Thr Leu Met Ile
            420                 425                 430
Ser Arg Thr Pro Glu Val Thr Cys Val Val Val Asp Val Ser His Glu
        435                 440                 445
Asp Pro Glu Val Lys Phe Asn Trp Tyr Val Asp Gly Val Glu Val His
    450                 455                 460
Asn Ala Lys Thr Lys Pro Arg Glu Glu Gln Tyr Asn Ser Thr Tyr Arg
465                 470                 475                 480
Val Val Ser Val Leu Thr Val Leu His Gln Asp Trp Leu Asn Gly Lys
                485                 490                 495
Glu Tyr Lys Cys Lys Val Ser Asn Lys Ala Leu Pro Ala Pro Ile Glu
            500                 505                 510
Lys Thr Ile Ser Lys Ala Lys Gly Gln Pro Arg Glu Pro Gln Val Tyr
        515                 520                 525
Thr Leu Pro Pro Ser Arg Asp Glu Leu Thr Lys Asn Gln Val Ser Leu
    530                 535                 540
Thr Cys Leu Val Lys Gly Phe Tyr Pro Ser Asp Ile Ala Val Glu Trp
545                 550                 555                 560
Glu Ser Asn Gly Gln Pro Glu Asn Asn Tyr Lys Thr Thr Pro Pro Val
                565                 570                 575
Leu Asp Ser Asp Gly Ser Phe Phe Leu Tyr Ser Lys Leu Thr Val Asp
            580                 585                 590
Lys Ser Arg Trp Gln Gln Gly Asn Val Phe Ser Cys Ser Val Met His
        595                 600                 605
Glu Ala Leu His Asn His Tyr Thr Gln Lys Ser Leu Ser Leu Ser Pro
    610                 615                 620
Gly Lys
625
```

<210> SEQ ID NO 86
<211> LENGTH: 1886
<212> TYPE: DNA
<213> ORGANISM: Artificial Sequence
<220> FEATURE:
<223> OTHER INFORMATION: AAT-Fc

<400> SEQUENCE: 86

```
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
tttgcaatgc tctccctggg gaccaaggct gacactcacg atgaaatcct ggagggcctg     240
aatttcaacc tcacggagat tccggaggct cagatccatg aaggcttcca ggaactcctc     300
cgtaccctca accagccaga cagccagctc cagctgacca ccggcaatgg cctgttcctc     360
agcgagggcc tgaagctagt ggataagttt ttggaggatg ttaaaaagtt gtaccactca     420
gaagccttca ctgtcaactt cggggacacc gaagaggcca agaaacagat caacgattac     480
```

-continued

```
gtggagaagg gtactcaagg gaaaattgtg gatttggtca aggagcttga cagagacaca    540
gttttttgctc tggtgaatta catcttcttt aaaggcaaat gggagagacc ctttgaagtc   600
aaggacaccg aggaagagga cttccacgtg gaccaggtga ccaccgtgaa ggtgcctatg    660
atgaagcgtt taggcatgtt taacatccag cactgtaaga agctgtccag ctgggtgctg    720
ctgatgaaat acctgggcaa tgccaccgcc atcttcttcc tgcctgatga ggggaaacta    780
cagcacctgg aaaatgaact cacccacgat atcatcacca agttcctgga aaatgaagac    840
agaaggtctg ccagcttaca tttacccaaa ctgtccatta ctggaaccta tgatctgaag    900
agcgtcctgg gtcaactggg catcactaag gtcttcagca atgggggctga cctctccggg    960
gtcacagagg aggcacccct gaagctctcc aaggccgtgc ataaggctgt gctgaccatc   1020
gacgagaaag ggactgaagc tgctggggcc atgttttag aggccatacc catgtctatc    1080
cccccgagg tcaagttcaa caaacccttt gtcttcttaa tgattgaaca aaataccaag    1140
tctccctct tcatgggaaa agtggtgaat cccacccaaa aaacgcgtga gcccaaatct    1200
tgtgacaaaa ctcacacatg cccaccgtgc ccagcacctg aactcctggg gggaccgtca   1260
gtcttcctct tccccccaaa acccaaggac accctcatga tctcccggac ccctgaggtc   1320
acatgcgtgg tggtggacgt gagccacgaa gaccctgagg tcaagttcaa ctggtacgtg   1380
gacggcgtgg aggtgcataa tgccaagaca aagccgcggg aggagcagac aacagcacgt   1440
accgtgtggt cagcgtcctc accgtcctgc accaggactg gctgaatggc aaggagtaca   1500
agtgcaaggt ctccaacaaa gccctcccag cccccatcga gaaaaccatc tccaaagcca   1560
aagggcagcc ccgagaacca caggtgtaca ccctgccccc atcccgggat gagctgacca   1620
agaaccaggt cagcctgacc tgcctggtca aaggcttcta tcccagcgac atcgccgtgg   1680
agtgggagag caatgggcag ccggagaaca actacaagac cacgcctccc gtgctggact   1740
ccgacggctc cttcttcctc tacagcaagc tcaccgtgga caagagcagg tggcagcagg   1800
ggaacgtctt ctcatgctcc gtgatgcatg aggctctgca caaccactac acgcagaaga   1860
gcctctccct gtctccgggt aaatga                                        1886
```

<210> SEQ ID NO 87
<211> LENGTH: 628
<212> TYPE: PRT
<213> ORGANISM: Artificial Sequence
<220> FEATURE:
<223> OTHER INFORMATION: AAT-Fc

<400> SEQUENCE: 87

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110
```

-continued

```
Thr Thr Gly Asn Gly Leu Phe Leu Ser Glu Gly Leu Lys Leu Val Asp
        115                 120                 125
Lys Phe Leu Glu Asp Val Lys Lys Leu Tyr His Ser Glu Ala Phe Thr
130                 135                 140
Val Asn Phe Gly Asp Thr Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
            180                 185                 190
Lys Trp Glu Arg Pro Phe Glu Val Lys Asp Thr Glu Glu Glu Asp Phe
        195                 200                 205
His Val Asp Gln Val Thr Thr Val Lys Val Pro Met Met Lys Arg Leu
    210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
    290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
        355                 360                 365
Pro Phe Val Phe Leu Met Ile Glu Gln Asn Thr Lys Ser Pro Leu Phe
    370                 375                 380
Met Gly Lys Val Val Asn Pro Thr Gln Lys Thr Arg Glu Pro Lys Ser
385                 390                 395                 400
Cys Asp Lys Thr His Thr Cys Pro Pro Cys Pro Ala Pro Glu Leu Leu
                405                 410                 415
Gly Gly Pro Ser Val Phe Leu Phe Pro Pro Lys Pro Lys Asp Thr Leu
            420                 425                 430
Met Ile Ser Arg Thr Pro Glu Val Thr Cys Val Val Val Asp Val Ser
        435                 440                 445
His Glu Asp Pro Glu Val Lys Phe Asn Trp Tyr Val Asp Gly Val Glu
    450                 455                 460
Val His Asn Ala Lys Thr Lys Pro Arg Glu Glu Gln Tyr Asn Ser Thr
465                 470                 475                 480
Tyr Arg Val Val Ser Val Leu Thr Val Leu His Gln Asp Trp Leu Asn
                485                 490                 495
Gly Lys Glu Tyr Lys Cys Lys Val Ser Asn Lys Ala Leu Pro Ala Pro
            500                 505                 510
Ile Glu Lys Thr Ile Ser Lys Ala Lys Gly Gln Pro Arg Glu Pro Gln
        515                 520                 525
Val Tyr Thr Leu Pro Pro Ser Arg Asp Glu Leu Thr Lys Asn Gln Val
```

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
                565                 570                 575

Pro Val Leu Asp Ser Asp Gly Ser Phe Phe Leu Tyr Ser Lys Leu Thr
                580                 585                 590

Val Asp Lys Ser Arg Trp Gln Gln Gly Asn Val Phe Ser Cys Ser Val
                595                 600                 605

Met His Glu Ala Leu His Asn His Tyr Thr Gln Lys Ser Leu Ser Leu
                610                 615                 620

Ser Pro Gly Lys
625

<210> SEQ ID NO 88
<211> LENGTH: 1886
<212> TYPE: DNA
<213> ORGANISM: Artificial Sequence
<220> FEATURE:
<223> OTHER INFORMATION: AAT-Fc

<400> SEQUENCE: 88

```
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
tttgcaatgc tctccctggg gaccaaggct gacactcacg atgaaatcct ggagggcctg     240
aatttcaacc tcacggagat tccggaggct cagatccatg aaggcttcca ggaactcctc     300
cgtaccctca accagccaga cagccagctc cagctgacca ccggcaatgg cctgttcctc     360
agcgagggcc tgaagctagt ggataagttt ttggaggatg ttaaaaagtt gtaccactca     420
gaagccttca ctgtcaactt cggggacacc gaagaggcca gaaacagat caacgattac     480
gtggagaagg gtactcaagg gaaaattgtg gatttggtca aggagcttga cagagacaca     540
gttttttgctc tggtgaatta catcttcttt aaaggcaaat gggagagacc ctttgaagtc     600
aaggacaccg aggaagagga cttccacgtg gaccaggcga ccaccgtgaa ggtgcctatg     660
atgaagcgtt taggcatgtt taacatccag cactgtaaga agctgtccag ctgggtgctg     720
ctgatgaaat acctgggcaa tgccaccgcc atcttcttcc tgcctgatga ggggaaacta     780
cagcacctgg aaaatgaact cacccacgat atcatcacca agttcctgga aaatgaagac     840
agaaggtctg ccagcttaca tttacccaaa ctgtccatta ctggaaccta tgatctgaag     900
agcgtcctgg gtcaactggg catcactaag gtcttcagca atgggctga cctctccggg     960
gtcacagagg aggcaccct gaagctctcc aaggccgtgc ataagctgt gctgaccatc    1020
gacgagaaag ggactgaagc tgctggggcc atgttttag aggccatacc catgtctatc    1080
cccccccgagg tcaagttcaa caaacccttt gtcttcttaa tgattgaaca aaataccaag    1140
tctcccctct tcatgggaaa agtggtgaat cccacccaaa aaacgcgtga gcccaaatct    1200
tgtgacaaaa ctcacacatg cccaccgtgc ccagcacctg aactcctggg gggaccgtca    1260
gtcttcctct tccccccaaa acccaaggac accctcatga tctcccggac ccctgaggtc    1320
acatgcgtgg tggtggacgt gagccacgaa gaccctgagg tcaagttcaa ctggtacgtg    1380
gacggcgtgg aggtgcataa tgccaagaca aagccgcggg aggagcagta acagcacgt    1440
accgtgtggt cagcgtcctc accgtcctgc accaggactg gctgaatggc aaggagtaca    1500
```

```
agtgcaaggt ctccaacaaa gccctcccag cccccatcga aaaaccatc tccaaagcca   1560 aagggcagcc ccgagaacca caggtgtaca ccctgccccc atcccgggat gagctgacca   1620
agaaccaggt cagcctgacc tgcctggtca aaggcttcta tcccagcgac atcgccgtgg   1680
agtgggagag caatgggcag ccggagaaca actacaagac cacgcctccc gtgctggact   1740
ccgacggctc cttcttcctc tacagcaagc tcaccgtgga caagagcagg tggcagcagg   1800
ggaacgtctt ctcatgctcc gtgatgcatg aggctctgca caaccactac acgcagaaga   1860
gcctctccct gtctccgggt aaatga                                        1886
```

<210> SEQ ID NO 89
<211> LENGTH: 628
<212> TYPE: PRT
<213> ORGANISM: Artificial Sequence
<220> FEATURE:
<223> OTHER INFORMATION: AAT-Fc

<400> SEQUENCE: 89

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285
```

```
Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Thr Arg Glu Pro Lys Ser
385                 390                 395                 400

Cys Asp Lys Thr His Thr Cys Pro Pro Cys Pro Ala Pro Glu Leu Leu
                405                 410                 415

Gly Gly Pro Ser Val Phe Leu Phe Pro Pro Lys Pro Lys Asp Thr Leu
            420                 425                 430

Met Ile Ser Arg Thr Pro Glu Val Thr Cys Val Val Val Asp Val Ser
        435                 440                 445

His Glu Asp Pro Glu Val Lys Phe Asn Trp Tyr Val Asp Gly Val Glu
    450                 455                 460

Val His Asn Ala Lys Thr Lys Pro Arg Glu Glu Gln Tyr Asn Ser Thr
465                 470                 475                 480

Tyr Arg Val Val Ser Val Leu Thr Val Leu His Gln Asp Trp Leu Asn
                485                 490                 495

Gly Lys Glu Tyr Lys Cys Lys Val Ser Asn Lys Ala Leu Pro Ala Pro
            500                 505                 510

Ile Glu Lys Thr Ile Ser Lys Ala Lys Gly Gln Pro Arg Glu Pro Gln
        515                 520                 525

Val Tyr Thr Leu Pro Pro Ser Arg Asp Glu Leu Thr Lys Asn Gln Val
    530                 535                 540

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
                565                 570                 575

Pro Val Leu Asp Ser Asp Gly Ser Phe Phe Leu Tyr Ser Lys Leu Thr
            580                 585                 590

Val Asp Lys Ser Arg Trp Gln Gln Gly Asn Val Phe Ser Cys Ser Val
        595                 600                 605

Met His Glu Ala Leu His Asn His Tyr Thr Gln Lys Ser Leu Ser Leu
    610                 615                 620

Ser Pro Gly Lys
625

<210> SEQ ID NO 90
<211> LENGTH: 80
<212> TYPE: PRT
<213> ORGANISM: Artificial Sequence
<220> FEATURE:
<223> OTHER INFORMATION: synthetic peptide

<400> SEQUENCE: 90

Gly Ala Asp Leu Ser Gly Val Thr Glu Glu Ala Pro Leu Lys Leu Ser
1               5                   10                  15
```

-continued

Lys Ala Val His Lys Ala Val Leu Thr Ile Asp Glu Lys Gly Thr Glu
            20                  25                  30

Ala Ala Gly Ala Met Phe Leu Glu Ala Ile Pro Met Ser Ile Pro Pro
        35                  40                  45

Glu Val Lys Phe Asn Lys Pro Phe Val Phe Leu Met Ile Glu Gln Asn
    50                  55                  60

Thr Lys Ser Pro Leu Phe Met Gly Lys Val Val Asn Pro Thr Gln Lys
65                  70                  75                  80

<210> SEQ ID NO 91
<211> LENGTH: 36
<212> TYPE: PRT
<213> ORGANISM: Artificial Sequence
<220> FEATURE:
<223> OTHER INFORMATION: synthetic peptide

<400> SEQUENCE: 91

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro Thr Gln Lys
        35

<210> SEQ ID NO 92
<211> LENGTH: 62
<212> TYPE: DNA
<213> ORGANISM: Homo sapiens

<400> SEQUENCE: 92
tttagaggcc atacccatgt ctatcccccc cgaggtcaag ttcaacaaac ccctttgtct    60
tt                                                                  62

<210> SEQ ID NO 93
<211> LENGTH: 62
<212> TYPE: DNA
<213> ORGANISM: Artificial Sequence
<220> FEATURE:
<223> OTHER INFORMATION: mutant

<400> SEQUENCE: 93
tttagaggcc atatgcatgt ctatcccccc cgaggtcaag ttcaacaaac ccctttgtct    60
tt                                                                  62

<210> SEQ ID NO 94
<211> LENGTH: 1950
<212> TYPE: DNA
<213> ORGANISM: Artificial Sequence
<220> FEATURE:
<223> OTHER INFORMATION: Artificial: derived from human alpha-1
      antitrypsin and human Fc fragment of IgG1 with hinge deletion

<400> SEQUENCE: 94
gaattcgcca ccatgccgtc ttctgtctcg tgggcatcc tcctgctggc aggcctgtgc    60
tgcctggtcc ctgtctccct ggctgaggat ccccagggag atgctgccca gaagacagat   120 acatccacc acgatcagga tcacccaacc ttcaacaaga tcaccccaa cctggctgag    180 ttcgccttca gcctataccg ccagctggca caccagtcca acagcaccaa tatcttcttc   240
tccccagtga gcatcgctac agcctttgca atgctctccc tggggaccaa ggctgacact   300
cacgatgaaa tcctggaggg cctgaatttc aacctcacgg agattccgga ggctcagatc   360

```
catgaaggct tccaggaact cctccgtacc ctcaaccagc cagacagcca gctccagctg      420
accaccggca atggcctgtt cctcagcgag ggcctgaagc tagtggataa gtttttggag      480
gatgttaaaa agttgtacca ctcagaagcc ttcactgtca acttcgggga caccgaagag      540
gccaagaaac agatcaacga ttacgtggag aagggtactc aagggaaaat tgtggatttg      600
gtcaaggagc ttgacagaga cacagttttt gctctggtga attacatctt ctttaaaggc      660
aaatgggaga gacccttga agtcaaggac accgaggaag aggacttcca cgtggaccag      720
gcgaccaccg tgaaggtgcc tatgatgaag cgtttaggca tgtttaacat ccagcactgt      780
aagaagctgt ccagctgggt gctgctgatg aaatacctgg gcaatgccac cgccatcttc      840
ttcctgcctg atgaggggaa actacagcac ctggaaaatg aactcaccca cgatatcatc      900
accaagttcc tggaaaatga agacagaagg tctgccagct acatttacc caaactgtcc       960 attactggaa cctatgatct gaagagcgtc ctgggtcaac tgggcatcac taaggtcttc     1020
agcaatgggg ctgacctctc cggggtcaca gaggaggcac ccctgaagct ctccaaggcc     1080
gtgcataagg ctgtgctgac catcgacgag aaagggactg aagctgctgg ggccatgttt     1140
ttagaggcca tacccatgtc tatcccccc gaggtcaagt tcaacaaacc ctttgtcttc      1200
ttaatgattg aacaaaatac caagtctccc ctcttcatgg gaaaagtggt gaatcccacc     1260 caaaaacgc gtacatgccc accgtgccca gcacctgaac tcctgggggg accgtcagtc      1320
ttcctcttcc cccaaaacc caaggacacc ctcatgatct cccggacccc tgaggtcaca      1380
tgcgtggtgg tggacgtgag ccacgaagac cctgaggtca agttcaactg gtacgtggac     1440
ggcgtggagg tgcataatgc caagacaaag ccgcgggagg agcagtacaa cagcacgtac     1500
cgtgtggtca gcgtcctcac cgtcctgcac caggactggc tgaatggcaa ggagtacaag     1560
tgcaaggtct ccaacaaagc cctcccagcc cccatcgaga aaaccatctc caaagccaaa     1620
gggcagcccc gagaaccaca ggtgtacacc ctgcccccat cccgggatga gctgaccaag     1680
aaccaggtca gcctgacctg cctggtcaaa ggcttctatc ccagcgacat cgccgtggag     1740
tgggagagca atgggcagcc ggagaacaac tacaagacca cgcctcccgt gctggactcc     1800
gacggctcct tcttcctcta cagcaagctc accgtggaca gagcaggtg gcagcagggg     1860 aacgtcttct catgctccgt gatgcatgag gctctgcaca accactacac gcagaagagc     1920
ctctccctgt ctccgggtaa atgaggatct                                      1950
```

<210> SEQ ID NO 95
<211> LENGTH: 643
<212> TYPE: PRT
<213> ORGANISM: Artificial Sequence
<220> FEATURE:
<223> OTHER INFORMATION: derived from human alpha-1 antitrypsin and human Fc fragment of IgG1

<400> SEQUENCE: 95

```
Met Pro Ser Ser Val Ser Trp Gly Ile Leu Leu Leu Ala Gly Leu Cys
  1               5                  10                  15

Cys Leu Val Pro Val Ser Leu Ala Glu Asp Pro Gln Gly Asp Ala Ala
                 20                  25                  30

Gln Lys Thr Asp Thr Ser His His Asp Gln Asp His Pro Thr Phe Asn
             35                  40                  45

Lys Ile Thr Pro Asn Leu Ala Glu Phe Ala Phe Ser Leu Tyr Arg Gln
         50                  55                  60

Leu Ala His Gln Ser Asn Ser Thr Asn Ile Phe Phe Ser Pro Val Ser
```

-continued

```
                65                  70                  75                  80
Ile Ala Thr Ala Phe Ala Met Leu Ser Leu Gly Thr Lys Ala Asp Thr
                    85                  90                  95

His Asp Glu Ile Leu Glu Gly Leu Asn Phe Asn Leu Thr Glu Ile Pro
                    100                 105                 110

Glu Ala Gln Ile His Glu Gly Phe Gln Glu Leu Leu Arg Thr Leu Asn
                    115                 120                 125

Gln Pro Asp Ser Gln Leu Gln Leu Thr Thr Gly Asn Gly Leu Phe Leu
                    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                    165                 170                 175

Ala Lys Lys Gln Ile Asn Asp Tyr Val Glu Lys Gly Thr Gln Gly Lys
                    180                 185                 190

Ile Val Asp Leu Val Lys Glu Leu Asp Arg Asp Thr Val Phe Ala Leu
                    195                 200                 205

Val Asn Tyr Ile Phe Phe Lys Gly Lys Trp Glu Arg Pro Phe Glu Val
                    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                    245                 250                 255

Lys Lys Leu Ser Ser Trp Val Leu Leu Met Lys Tyr Leu Gly Asn Ala
                    260                 265                 270

Thr Ala Ile Phe Phe Leu Pro Asp Glu Gly Lys Leu Gln His Leu Glu
                    275                 280                 285

Asn Glu Leu Thr His Asp Ile Ile Thr Lys Phe Leu Glu Asn Glu Asp
                    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                    325                 330                 335

Ser Asn Gly Ala Asp Leu Ser Gly Val Thr Glu Glu Ala Pro Leu Lys
                    340                 345                 350

Leu Ser Lys Ala Val His Lys Ala Val Leu Thr Ile Asp Glu Lys Gly
                    355                 360                 365

Thr Glu Ala Ala Gly Ala Met Phe Leu Glu Ala Ile Pro Met Ser Ile
                    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                    405                 410                 415

Gln Lys Thr Arg Thr Cys Pro Cys Pro Ala Pro Glu Leu Leu Gly
                    420                 425                 430

Gly Pro Ser Val Phe Leu Phe Pro Pro Lys Pro Lys Asp Thr Leu Met
                    435                 440                 445

Ile Ser Arg Thr Pro Glu Val Thr Cys Val Val Asp Val Ser His
                    450                 455                 460

Glu Asp Pro Glu Val Lys Phe Asn Trp Tyr Val Asp Gly Val Glu Val
465                 470                 475                 480

His Asn Ala Lys Thr Lys Pro Arg Glu Glu Gln Tyr Asn Ser Thr Tyr
                    485                 490                 495
```

```
Arg Val Val Ser Val Leu Thr Val Leu His Gln Asp Trp Leu Asn Gly
            500                 505                 510
Lys Glu Tyr Lys Cys Lys Val Ser Asn Lys Ala Leu Pro Ala Pro Ile
        515                 520                 525
Glu Lys Thr Ile Ser Lys Ala Lys Gly Gln Pro Arg Glu Pro Gln Val
    530                 535                 540
Tyr Thr Leu Pro Pro Ser Arg Asp Glu Leu Thr Lys Asn Gln Val Ser
545                 550                 555                 560
Leu Thr Cys Leu Val Lys Gly Phe Tyr Pro Ser Asp Ile Ala Val Glu
                565                 570                 575
Trp Glu Ser Asn Gly Gln Pro Glu Asn Asn Tyr Lys Thr Thr Pro Pro
            580                 585                 590
Val Leu Asp Ser Asp Gly Ser Phe Phe Leu Tyr Ser Lys Leu Thr Val
        595                 600                 605
Asp Lys Ser Arg Trp Gln Gln Gly Asn Val Phe Ser Cys Ser Val Met
    610                 615                 620
His Glu Ala Leu His Asn His Tyr Thr Gln Lys Ser Leu Ser Leu Ser
625                 630                 635                 640
Pro Gly Lys

<210> SEQ ID NO 96
<211> LENGTH: 1962
<212> TYPE: DNA
<213> ORGANISM: Artificial Sequence
<220> FEATURE:
<223> OTHER INFORMATION: derived from human alpha-1 antitrypsin and
      human Fc fragment of IgG2

<400> SEQUENCE: 96
gaattcgcca ccatgccgtc ttctgtctcg tggggcatcc tcctgctggc aggcctgtgc      60
tgcctggtcc ctgtctccct ggctgaggat ccccagggag atgctgccca agaagacaga    120
acatcccacc acgatcagga tcacccaacc ttcaacaaga tcaccccaa cctggctgag    180
ttcgccttca gcctatacccg ccagctggca caccagtcca acagcaccaa tatcttcttc    240
tccccagtga gcatcgctac agcctttgca atgctctccc tggggaccaa ggctgacact    300
cacgatgaaa tcctggaggg cctgaatttc aacctcacgg agattccgga ggctcagatc    360
catgaaggct tccaggaact cctccgtacc ctcaaccagc cagacagcca gctccagctg    420
accaccggca atggcctgtt cctcagcgag ggcctgaagc tagtggataa gttttttggag    480
gatgttaaaa agttgtacca ctcagaagcc ttcactgtca acttcgggga caccgaagag    540
gccaagaaac agatcaacga ttacgtggag aagggtactc aagggaaaat tgtggatttg    600
gtcaaggagc ttgacagaga cacagttttt gctctggtga attacatctt ctttaaaggc    660
aaatgggaga gacccttcga agtcaaggac accgaggaag aggacttcca cgtggaccag    720
gcgaccaccg tgaaggtgcc tatgatgaag cgtttaggca tgtttaacat ccagcactgt    780
aagaagctgt ccagctgggt gctgctgatg aaatacctgg gcaatgccac cgccatcttc    840
ttcctgcctg atgaggggaa actacagcac ctggaaaatg aactcaccca cgatatcatc    900
accaagttcc tggaaaatga agacagaagg tctgccagct acatttacc caaactgtcc    960
attactggaa cctatgatct gaagagcgtc ctgggtcaac tgggcatcac taaggtcttc   1020
agcaatgggg ctgacctctc cggggtcaca gaggaggcac ccctgaagct ctccaaggcc   1080
gtgcataagg ctgtgctgac catcgacgag aaagggactg aagctgctgg ggccatgttt   1140
```

```
ttagaggcca tacccatgtc tatcccccccc gaggtcaagt tcaacaaacc ctttgtcttc    1200
ttaatgattg aacaaaatac caagtctccc ctcttcatgg gaaaagtggt gaatcccacc    1260
caaaaaacgc gtcgcaaatg ttgtgtcgag tgcccaccgt gcccagcacc acctgtggca    1320
ggaccgtcag tcttcctctt ccccccaaaa cccaaggaca ccctcatgat ctcccggacc    1380
cctgaggtca catgcgtggt ggtggacgtg agccacgaag accctgaggt caagttcaac    1440
tggtacgtgg acggcgtgga ggtgcataat gccaagacaa agccgcggga ggagcagtac    1500
aacagcacgt accgtgtggt cagcgtcctc accgtcctgc accaggactg gctgaatggc    1560
aaggagtaca agtgcaaggt ctccaacaaa gccctcccag cccccatcga gaaaaccatc    1620
tccaaagcca aggggcagcc ccgagaacca caggtgtaca ccctgccccc atcccgggat    1680
gagctgacca agaaccaggt cagcctgacc tgcctggtca aaggcttcta tcccagcgac    1740
atcgccgtgg agtgggagag caatgggcag ccggagaaca actacaagac cacgcctccc    1800
gtgctggact ccgacggctc cttcttcctc tacagcaagc tcaccgtgga caagagcagg    1860
tggcagcagg ggaacgtctt ctcatgctcc gtgatgcatg aggctctgca caaccactac    1920
acgcagaaga gcctctccct gtctccgggt aaatgaggat ct                       1962
```

<210> SEQ ID NO 97  
<211> LENGTH: 647  
<212> TYPE: PRT  
<213> ORGANISM: Artificial Sequence  
<220> FEATURE:  
<223> OTHER INFORMATION: derived from human alpha-1 antitrypsin and human Fc fragment of IgG2

<400> SEQUENCE: 97

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
```

```
                210                 215                 220
Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
            245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
            325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys Thr Arg Arg Lys Cys Cys Val Glu Cys Pro Pro Cys Pro Ala
            420                 425                 430

Pro Pro Val Ala Gly Pro Ser Val Phe Leu Phe Pro Pro Lys Pro Lys
            435                 440                 445

Asp Thr Leu Met Ile Ser Arg Thr Pro Glu Val Thr Cys Val Val Val
450                 455                 460

Asp Val Ser His Glu Asp Pro Glu Val Lys Phe Asn Trp Tyr Val Asp
465                 470                 475                 480

Gly Val Glu Val His Asn Ala Lys Thr Lys Pro Arg Glu Glu Gln Tyr
            485                 490                 495

Asn Ser Thr Tyr Arg Val Val Ser Val Leu Thr Val Leu His Gln Asp
            500                 505                 510

Trp Leu Asn Gly Lys Glu Tyr Lys Cys Lys Val Ser Asn Lys Ala Leu
            515                 520                 525

Pro Ala Pro Ile Glu Lys Thr Ile Ser Lys Ala Lys Gly Gln Pro Arg
            530                 535                 540

Glu Pro Gln Val Tyr Thr Leu Pro Pro Ser Arg Asp Glu Leu Thr Lys
545                 550                 555                 560

Asn Gln Val Ser Leu Thr Cys Leu Val Lys Gly Phe Tyr Pro Ser Asp
            565                 570                 575

Ile Ala Val Glu Trp Glu Ser Asn Gly Gln Pro Glu Asn Asn Tyr Lys
            580                 585                 590

Thr Thr Pro Pro Val Leu Asp Ser Asp Gly Ser Phe Phe Leu Tyr Ser
            595                 600                 605

Lys Leu Thr Val Asp Lys Ser Arg Trp Gln Gln Gly Asn Val Phe Ser
            610                 615                 620

Cys Ser Val Met His Glu Ala Leu His Asn His Tyr Thr Gln Lys Ser
625                 630                 635                 640
```

Leu Ser Leu Ser Pro Gly Lys
                645

<210> SEQ ID NO 98
<211> LENGTH: 1995
<212> TYPE: DNA
<213> ORGANISM: Artificial Sequence
<220> FEATURE:
<223> OTHER INFORMATION: derived from human alpha-1 antitrypsin and
      human FC fragment IgG3

<400> SEQUENCE: 98

| | | | | |
|---|---|---|---|---|
| gaattcgcca ccatgccgtc | ttctgtctcg | tgcctggtcc | ctgtctccct | ggctgaggat | 60 |
| acatcccacc acgatcagga | tcacccaacc | ttcgccttca | gcctataccg | ccagctggca | 120 |
| tccccagtga gcatcgctac | agcctttgca | cacgatgaaa | tcctggaggg | cctgaatttc | 180 |
| catgaaggct tccaggaact | cctccgtacc | accaccggca | atggcctgtt | cctcagcgag | 240 |
| tggggcatcc tcctgctggc | aggcctgtgc | ccccagggag | atgctgccca | aagacagat | 300 |
| ttcaacaaga tcaccccaa | cctggctgag | caccagtcca | cagcaccaa | tatcttcttc | 360 |
| atgctctccc tggggaccaa | ggctgacact | aacctcacgg | agattccgga | ggctcagatc | 420 |
| ctcaaccagc cagacagcca | gctccagctg | ggcctgaagc | tagtggataa | gttttttggag | 480 |
| gatgttaaaa agttgtacca | ctcagaagcc | ttcactgtca | acttcgggga | caccgaagag | 540 |
| gccaagaaac agatcaacga | ttacgtggag | aagggtactc | aagggaaaat | tgtggatttg | 600 |
| gtcaaggagc ttgacagaga | cacagttttt | gctctggtga | attacatctt | ctttaaaggc | 660 |
| aaatgggaga gacccttttga | agtcaaggac | accgaggaag | aggacttcca | cgtggaccag | 720 |
| gcgaccaccg tgaaggtgcc | tatgatgaag | cgtttaggca | tgtttaacat | ccagcactgt | 780 |
| aagaagctgt ccagctgggt | gctgctgatg | aaatacctgg | gcaatgccac | cgccatcttc | 840 |
| ttcctgcctg atgaggggaa | actacagcac | ctggaaaatg | aactcaccca | cgatatcatc | 900 |
| accaagttcc tggaaaatga | agacagaagg | tctgccagct | acatttacc | caaactgtcc | 960 |
| attactggaa cctatgatct | gaagagcgtc | ctgggtcaac | tggcatcac | taaggtcttc | 1020 |
| agcaatgggg ctgacctctc | cggggtcaca | gaggaggcac | ccctgaagct | ctccaaggcc | 1080 |
| gtgcataagg ctgtgctgac | catcgacgag | aaagggactg | aagctgctgg | ggccatgttt | 1140 |
| ttagaggcca tacccatgtc | tatccccccc | gaggtcaagt | tcaacaaacc | ctttgtcttc | 1200 |
| ttaatgattg aacaaaatac | caagtctccc | ctcttcatgg | gaaaagtggt | gaatcccacc | 1260 |
| caaaaaacgc gtccatgccc | acggtgccca | gagcccaaat | cttgtgacac | acctcccccg | 1320 |
| tgcccaaggt gccagcacc | tgaactcctg | ggggaccgt | cagtcttcct | cttccccca | 1380 |
| aaacccaagg acaccctcat | gatctcccgg | acccctgagg | tcacatgcgt | ggtggtggac | 1440 |
| gtgagccacg aagaccctga | ggtcaagttc | aactggtacg | tggacggcgt | ggaggtgcat | 1500 |
| aatgccaaga caaagccgcg | ggaggagcag | tacaacagca | cgtaccgtgt | ggtcagcgtc | 1560 |
| ctcaccgtcc tgcaccagga | ctggctgaat | ggcaaggagt | acaagtgcaa | ggtctccaac | 1620 |
| aaagccctcc cagcccccat | cgagaaaacc | atctccaaag | ccaaagggca | gccccgagaa | 1680 |
| ccacaggtgt acaccctgcc | cccatcccgg | gatgagctga | ccaagaacca | ggtcagcctg | 1740 |
| acctgcctgg tcaaaggctt | ctatcccagc | gacatcgccg | tggagtggga | gagcaatggg | 1800 |
| cagccggaga acaactacaa | gaccacgcct | cccgtgctgg | actccgacgg | ctccttcttc | 1860 |
| ctctacagca agctcaccgt | ggacaagagc | aggtggcagc | aggggaacgt | cttctcatgc | 1920 |

```
tccgtgatgc atgaggctct gcacaaccac tacacgcaga gagcctctc cctgtctccg    1980 ggtaaatgag gatct                                                    1995
```

<210> SEQ ID NO 99
<211> LENGTH: 658
<212> TYPE: PRT
<213> ORGANISM: Artificial Sequence
<220> FEATURE:
<223> OTHER INFORMATION: derived from human alpha-1 antitrypsin and human Fc fragment of IgG3

<400> SEQUENCE: 99

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
```

-continued

```
                340             345             350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
        370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Thr Arg Pro Cys Pro Arg Cys Pro Glu Pro Lys Ser Cys Asp
            420                 425                 430
Thr Pro Pro Pro Cys Pro Arg Cys Pro Ala Pro Glu Leu Leu Gly Gly
        435                 440                 445
Pro Ser Val Phe Leu Phe Pro Pro Lys Pro Lys Asp Thr Leu Met Ile
    450                 455                 460
Ser Arg Thr Pro Glu Val Thr Cys Val Val Val Asp Val Ser His Glu
465                 470                 475                 480
Asp Pro Glu Val Lys Phe Asn Trp Tyr Val Asp Gly Val Glu Val His
                485                 490                 495
Asn Ala Lys Thr Lys Pro Arg Glu Glu Gln Tyr Asn Ser Thr Tyr Arg
            500                 505                 510
Val Val Ser Val Leu Thr Val Leu His Gln Asp Trp Leu Asn Gly Lys
        515                 520                 525
Glu Tyr Lys Cys Lys Val Ser Asn Lys Ala Leu Pro Ala Pro Ile Glu
    530                 535                 540
Lys Thr Ile Ser Lys Ala Lys Gly Gln Pro Arg Glu Pro Gln Val Tyr
545                 550                 555                 560
Thr Leu Pro Pro Ser Arg Asp Glu Leu Thr Lys Asn Gln Val Ser Leu
                565                 570                 575
Thr Cys Leu Val Lys Gly Phe Tyr Pro Ser Asp Ile Ala Val Glu Trp
            580                 585                 590
Glu Ser Asn Gly Gln Pro Glu Asn Asn Tyr Lys Thr Thr Pro Pro Val
        595                 600                 605
Leu Asp Ser Asp Gly Ser Phe Phe Leu Tyr Ser Lys Leu Thr Val Asp
    610                 615                 620
Lys Ser Arg Trp Gln Gln Gly Asn Val Phe Ser Cys Ser Val Met His
625                 630                 635                 640
Glu Ala Leu His Asn His Tyr Thr Gln Lys Ser Leu Ser Leu Ser Pro
                645                 650                 655
Gly Lys

<210> SEQ ID NO 100
<211> LENGTH: 1965
<212> TYPE: DNA
<213> ORGANISM: Artificial Sequence
<220> FEATURE:
<223> OTHER INFORMATION: derived from human alpha-1 antitrypsin and
      human Fc fragment of IgG4

<400> SEQUENCE: 100
gaattcgcca ccatgccgtc ttctgtctcg tggggcatcc tcctgctggc aggcctgtgc     60
tgcctggtcc ctgtctccct ggctgaggat ccccagggag atgctgccca gaagacagat    120
acatcccacc acgatcagga tcacccaacc ttcaacaaga tcaccccaa  cctggctgag    180 ttcgccttca gcctataccg ccagctggca caccagtcca acagcaccaa tatcttcttc    240
```

```
tccccagtga gcatcgctac agcctttgca atgctctccc tgggaccaa ggctgacact    300 cacgatgaaa tcctggaggg cctgaatttc aacctcacgg agattccgga ggctcagatc    360
catgaaggct tccaggaact cctccgtacc ctcaaccagc cagacagcca gctccagctg    420
accaccggca atggcctgtt cctcagcgag ggcctgaagc tagtggataa gttttttggag   480 gatgttaaaa agttgtacca ctcagaagcc ttcactgtca acttcgggga caccgaagag    540
gccaagaaac agatcaacga ttacgtggag aagggtactc aagggaaaat tgtggatttg    600
gtcaaggagc ttgacagaga cacagttttt gctctggtga attacatctt ctttaaaggc    660
aaatgggaga gacccttga agtcaaggac accgaggaag aggacttcca cgtggaccag     720
gcgaccaccg tgaaggtgcc tatgatgaag cgtttaggca tgtttaacat ccagcactgt    780
aagaagctgt ccagctgggt gctgctgatg aaatacctgg caatgccac cgccatcttc     840 ttcctgcctg atgaggggaa actacagcac ctggaaaatg aactcaccca cgatatcatc    900
accaagttcc tggaaaatga agacagaagg tctgccagct acatttacc caaactgtcc     960 attactggaa cctatgatct gaagagcgtc ctgggtcaac tgggcatcac taaggtcttc    1020
agcaatgggg ctgacctctc cggggtcaca gaggaggcac ccctgaagct ctccaaggcc    1080
gtgcataagg ctgtgctgac catcgacgag aaagggactg aagctgctgg ggccatgttt    1140
ttagaggcca tacccatgtc tatcccccc gaggtcaagt tcaacaaacc ctttgtcttc    1200
ttaatgattg aacaaaatac caagtctccc ctcttcatgg gaaaagtggt gaatcccacc    1260
caaaaaacgc gttccaaata tggtccccca tgcccatcat gcccagcacc tgagttcctg    1320
gggggaccgt cagtcttcct cttccccca aacccaagg acaccctcat gatctcccgg     1380 accctgagg tcacatgcgt ggtggtggac gtgagccacg aagaccctga ggtcaagttc     1440
aactggtacg tggacggcgt ggaggtgcat aatgccaaga caaagccgcg ggaggagcag    1500
tacaacagca cgtaccgtgt ggtcagcgtc ctcaccgtcc tgcaccagga ctggctgaat    1560
ggcaaggagt acaagtgcaa ggtctccaac aaagccctcc cagcccccat cgagaaaacc    1620
atctccaaag ccaaagggca gccccgagaa ccacaggtgt acaccctgcc cccatcccgg    1680
gatgagctga ccaagaacca ggtcagcctg acctgcctgg tcaaaggctt ctatcccagc    1740
gacatcgccg tggagtggga gagcaatggg cagccggaga acaactacaa gaccacgcct    1800
cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggtaaatgag gatct                    1965
```

<210> SEQ ID NO 101
<211> LENGTH: 648
<212> TYPE: PRT
<213> ORGANISM: Artificial Sequence
<220> FEATURE:
<223> OTHER INFORMATION: derived from human alpha-1 antitrypsin and
      human Fc fragment of IgG4

<400> SEQUENCE: 101

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45
```

```
Lys Ile Thr Pro Asn Leu Ala Glu Phe Ala Phe Ser Leu Tyr Arg Gln
     50                  55                  60

Leu Ala His Gln Ser Asn Ser Thr Asn Ile Phe Phe Ser Pro Val Ser
 65              70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
                100                 105                 110

Glu Ala Gln Ile His Glu Gly Phe Gln Glu Leu Leu Arg Thr Leu Asn
             115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Ser Lys Tyr Gly Pro Pro Cys Pro Ser Cys Pro Ala
            420                 425                 430

Pro Glu Phe Leu Gly Gly Pro Ser Val Phe Leu Phe Pro Pro Lys Pro
            435                 440                 445

Lys Asp Thr Leu Met Ile Ser Arg Thr Pro Glu Val Thr Cys Val Val
450                 455                 460

Val Asp Val Ser His Glu Asp Pro Glu Val Lys Phe Asn Trp Tyr Val
```

```
                465                 470                 475                 480
Asp Gly Val Glu Val His Asn Ala Lys Thr Lys Pro Arg Glu Glu Gln
                    485                 490                 495
Tyr Asn Ser Thr Tyr Arg Val Val Ser Val Leu Thr Val Leu His Gln
                500                 505                 510
Asp Trp Leu Asn Gly Lys Glu Tyr Lys Cys Lys Val Ser Asn Lys Ala
                515                 520                 525
Leu Pro Ala Pro Ile Glu Lys Thr Ile Ser Lys Ala Lys Gly Gln Pro
            530                 535                 540
Arg Glu Pro Gln Val Tyr Thr Leu Pro Pro Ser Arg Asp Glu Leu Thr
545                 550                 555                 560
Lys Asn Gln Val Ser Leu Thr Cys Leu Val Lys Gly Phe Tyr Pro Ser
                565                 570                 575
Asp Ile Ala Val Glu Trp Glu Ser Asn Gly Gln Pro Glu Asn Asn Tyr
                580                 585                 590
Lys Thr Thr Pro Pro Val Leu Asp Ser Asp Gly Ser Phe Phe Leu Tyr
                595                 600                 605
Ser Lys Leu Thr Val Asp Lys Ser Arg Trp Gln Gln Gly Asn Val Phe
            610                 615                 620
Ser Cys Ser Val Met His Glu Ala Leu His Asn His Tyr Thr Gln Lys
625                 630                 635                 640
Ser Leu Ser Leu Ser Pro Gly Lys
                645

<210> SEQ ID NO 102
<211> LENGTH: 634
<212> TYPE: PRT
<213> ORGANISM: Artificial Sequence
<220> FEATURE:
<223> OTHER INFORMATION: derived from human alpha-1 antitrypsin and
      human Fc fragment of IgG2 with hinge deletion

<400> SEQUENCE: 102

Met Pro Ser Ser Val Ser Trp Gly Ile Leu Leu Leu Ala Gly Leu Cys
1               5                   10                  15
Cys Leu Val Pro Val Ser Leu Ala Glu Asp Pro Gln Gly Asp Ala Ala
                20                  25                  30
Gln Lys Thr Asp Thr Ser His His Asp Gln Asp His Pro Thr Phe Asn
            35                  40                  45
Lys Ile Thr Pro Asn Leu Ala Glu Phe Ala Phe Ser Leu Tyr Arg Gln
        50                  55                  60
Leu Ala His Gln Ser Asn Ser Thr Asn Ile Phe Phe Ser Pro Val Ser
65                  70                  75                  80
Ile Ala Thr Ala Phe Ala Met Leu Ser Leu Gly Thr Lys Ala Asp Thr
                85                  90                  95
His Asp Glu Ile Leu Glu Gly Leu Asn Phe Asn Leu Thr Glu Ile Pro
                100                 105                 110
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
        130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
```

```
Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
        210                 215                 220

Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Pro Val Ala Gly Pro Ser Val Phe Leu Phe Pro Pro
            420                 425                 430

Lys Pro Lys Asp Thr Leu Met Ile Ser Arg Thr Pro Glu Val Thr Cys
            435                 440                 445

Val Val Val Asp Val Ser His Glu Asp Pro Glu Val Lys Phe Asn Trp
    450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
            500                 505                 510

Lys Ala Leu Pro Ala Pro Ile Glu Lys Thr Ile Ser Lys Ala Lys Gly
        515                 520                 525

Gln Pro Arg Glu Pro Gln Val Tyr Thr Leu Pro Pro Ser Arg Asp Glu
    530                 535                 540

Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
            580                 585                 590

Leu Tyr Ser Lys Leu Thr Val Asp Lys Ser Arg Trp Gln Gln Gly Asn
```

```
                    595                 600                 605

Val Phe Ser Cys Ser Val Met His Glu Ala Leu His Asn His Tyr Thr
        610                 615                 620

Gln Lys Ser Leu Ser Leu Ser Pro Gly Lys
625                 630

<210> SEQ ID NO 103
<211> LENGTH: 632
<212> TYPE: PRT
<213> ORGANISM: Artificial Sequence
<220> FEATURE:
<223> OTHER INFORMATION: derived from human alpha-1 antitrypsin and
      human Fc fragment of IgG3 with hinge deletion

<400> SEQUENCE: 103

Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320
```

```
Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Thr Arg Gly Gly Pro Ser Val Phe Leu Phe Pro Pro Lys Pro
            420                 425                 430

Lys Asp Thr Leu Met Ile Ser Arg Thr Pro Glu Val Thr Cys Val Val
        435                 440                 445

Val Asp Val Ser His Glu Asp Pro Glu Val Lys Phe Asn Trp Tyr Val
    450                 455                 460

Asp Gly Val Glu Val His Asn Ala Lys Thr Lys Pro Arg Glu Glu Gln
465                 470                 475                 480

Tyr Asn Ser Thr Tyr Arg Val Val Ser Val Leu Thr Val Leu His Gln
                485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
        515                 520                 525

Arg Glu Pro Gln Val Tyr Thr Leu Pro Pro Ser Arg Asp Glu Leu Thr
    530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
                565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
        595                 600                 605

Ser Cys Ser Val Met His Glu Ala Leu His Asn His Tyr Thr Gln Lys
    610                 615                 620

Ser Leu Ser Leu Ser Pro Gly Lys
625                 630

<210> SEQ ID NO 104
<211> LENGTH: 632
<212> TYPE: PRT
<213> ORGANISM: Artificial Sequence
<220> FEATURE:
<223> OTHER INFORMATION: derived from human alpha-1 antitrypsin and
      human Fc fragment of IgG4 with hinge deletion

<400> SEQUENCE: 104

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45
```

```
Lys Ile Thr Pro Asn Leu Ala Glu Phe Ala Phe Ser Leu Tyr Arg Gln
 50                  55                  60
Leu Ala His Gln Ser Asn Ser Thr Asn Ile Phe Ser Pro Val Ser
 65                  70                  75                  80
Ile Ala Thr Ala Phe Ala Met Leu Ser Leu Gly Thr Lys Ala Asp Thr
                 85                  90                  95
His Asp Glu Ile Leu Glu Gly Leu Asn Phe Asn Leu Thr Glu Ile Pro
                100                 105                 110
Glu Ala Gln Ile His Glu Gly Phe Gln Glu Leu Leu Arg Thr Leu Asn
                115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
                180                 185                 190
Ile Val Asp Leu Val Lys Glu Leu Asp Arg Asp Thr Val Phe Ala Leu
                195                 200                 205
Val Asn Tyr Ile Phe Phe Lys Gly Lys Trp Glu Arg Pro Phe Glu Val
210                 215                 220
Lys Asp Thr Glu Glu Glu Asp Phe His Val Asp Gln Ala Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
                260                 265                 270
Thr Ala Ile Phe Phe Leu Pro Asp Glu Gly Lys Leu Gln His Leu Glu
                275                 280                 285
Asn Glu Leu Thr His Asp Ile Ile Thr Lys Phe Leu Glu Asn Glu Asp
290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
                340                 345                 350
Leu Ser Lys Ala Val His Lys Ala Val Leu Thr Ile Asp Glu Lys Gly
                355                 360                 365
Thr Glu Ala Ala Gly Ala Met Phe Leu Glu Ala Ile Pro Met Ser Ile
                370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Thr Arg Gly Gly Pro Ser Val Phe Leu Phe Pro Pro Lys Pro
                420                 425                 430
Lys Asp Thr Leu Met Ile Ser Arg Thr Pro Glu Val Thr Cys Val Val
                435                 440                 445
Val Asp Val Ser His Glu Asp Pro Glu Val Lys Phe Asn Trp Tyr Val
                450                 455                 460
```

-continued

Asp Gly Val Glu Val His Asn Ala Lys Thr Lys Pro Arg Glu Glu Gln
465                 470                 475                 480

Tyr Asn Ser Thr Tyr Arg Val Ser Val Leu Thr Val Leu His Gln
            485                 490                 495

Asp Trp Leu Asn Gly Lys Glu Tyr Lys Cys Lys Val Ser Asn Lys Ala
            500                 505                 510

Leu Pro Ala Pro Ile Glu Lys Thr Ile Ser Lys Ala Lys Gly Gln Pro
            515                 520                 525

Arg Glu Pro Gln Val Tyr Thr Leu Pro Pro Ser Arg Asp Glu Leu Thr
            530                 535                 540

Lys Asn Gln Val Ser Leu Thr Cys Leu Val Lys Gly Phe Tyr Pro Ser
545                 550                 555                 560

Asp Ile Ala Val Glu Trp Glu Ser Asn Gly Gln Pro Glu Asn Asn Tyr
            565                 570                 575

Lys Thr Thr Pro Pro Val Leu Asp Ser Asp Gly Ser Phe Phe Leu Tyr
            580                 585                 590

Ser Lys Leu Thr Val Asp Lys Ser Arg Trp Gln Gln Gly Asn Val Phe
            595                 600                 605

Ser Cys Ser Val Met His Glu Ala Leu His Asn His Tyr Thr Gln Lys
610                 615                 620

Ser Leu Ser Leu Ser Pro Gly Lys
625                 630

<210> SEQ ID NO 105
<211> LENGTH: 10
<212> TYPE: PRT
<213> ORGANISM: Artificial Sequence
<220> FEATURE:
<223> OTHER INFORMATION: synthetic peptides

<400> SEQUENCE: 105

Gly Ile Thr Lys Val Phe Ser Asn Gly Ala
1               5                   10

<210> SEQ ID NO 106
<211> LENGTH: 10
<212> TYPE: PRT
<213> ORGANISM: Artificial Sequence
<220> FEATURE:
<223> OTHER INFORMATION: synthetic peptides

<400> SEQUENCE: 106

Asp Leu Ser Gly Val Thr Glu Glu Ala Pro
1               5                   10

<210> SEQ ID NO 107
<211> LENGTH: 10
<212> TYPE: PRT
<213> ORGANISM: Artificial Sequence
<220> FEATURE:
<223> OTHER INFORMATION: synthetic peptides

<400> SEQUENCE: 107

Leu Lys Leu Ser Lys Ala Val His Lys Ala
1               5                   10

<210> SEQ ID NO 108
<211> LENGTH: 10
<212> TYPE: PRT
<213> ORGANISM: Artificial Sequence
<220> FEATURE:
<223> OTHER INFORMATION: synthetic peptides

```
<400> SEQUENCE: 108

Val Leu Thr Ile Asp Glu Lys Gly Thr Glu
1               5                   10

<210> SEQ ID NO 109
<211> LENGTH: 10
<212> TYPE: PRT
<213> ORGANISM: Artificial Sequence
<220> FEATURE:
<223> OTHER INFORMATION: synthetic peptides

<400> SEQUENCE: 109

Ala Ala Gly Ala Met Phe Leu Glu Ala Ile
1               5                   10

<210> SEQ ID NO 110
<211> LENGTH: 10
<212> TYPE: PRT
<213> ORGANISM: Artificial Sequence
<220> FEATURE:
<223> OTHER INFORMATION: synthetic peptides

<400> SEQUENCE: 110

Pro Met Ser Ile Pro Pro Glu Val Lys Phe
1               5                   10

<210> SEQ ID NO 111
<211> LENGTH: 10
<212> TYPE: PRT
<213> ORGANISM: Artificial Sequence
<220> FEATURE:
<223> OTHER INFORMATION: synthetic peptides

<400> SEQUENCE: 111

Asn Lys Pro Phe Val Phe Leu Met Ile Glu
1               5                   10

<210> SEQ ID NO 112
<211> LENGTH: 10
<212> TYPE: PRT
<213> ORGANISM: Artificial Sequence
<220> FEATURE:
<223> OTHER INFORMATION: synthetic peptides

<400> SEQUENCE: 112

Gln Asn Thr Lys Ser Pro Leu Phe Met Gly
1               5                   10

<210> SEQ ID NO 113
<211> LENGTH: 8
<212> TYPE: PRT
<213> ORGANISM: Artificial Sequence
<220> FEATURE:
<223> OTHER INFORMATION: synthetic peptides

<400> SEQUENCE: 113

Lys Val Val Asn Pro Thr Gln Lys
1               5

<210> SEQ ID NO 114
<211> LENGTH: 22
<212> TYPE: PRT
<213> ORGANISM: Artificial Sequence
<220> FEATURE:
<223> OTHER INFORMATION: synthetic peptides
```

```
<400> SEQUENCE: 114

Leu Glu Ala Ile Pro Met Ser Ile Pro Pro Glu Val Lys Phe Asn Lys
1               5                   10                  15

Pro Phe Val Phe Leu Met
            20

<210> SEQ ID NO 115
<211> LENGTH: 20
<212> TYPE: PRT
<213> ORGANISM: Artificial Sequence
<220> FEATURE:
<223> OTHER INFORMATION: synthetic peptides

<400> SEQUENCE: 115

Leu Glu Ala Ile Pro Met Ser Ile Pro Pro Glu Val Lys Phe Asn Lys
1               5                   10                  15

Pro Phe Val Phe
            20
```

COMPOSITIONS AND METHODS FOR PREPARING A SUBJECT FOR ORGAN OR NON-ORGAN IMPLANTATION

PRIORITY

This U.S. Continuation Application claims priority to U.S. Non-Provisional application Ser. No. 14/227,414 filed Mar. 27, 2014, now issued as U.S. Pat. No. 9,486,509 on Nov. 8, 2016, which claims benefit to and is a continuation of PCT Application No. PCT/US2014/031848 filed Mar. 26, 2014, and U.S. Provisional Application No. 61/806,646 filed Mar. 29, 2013. These prior applications are incorporated herein by reference in their entirety for all purposes.

FIELD

Embodiments of the present invention relate to compositions and methods for pre-treatment of or preparing a subject for, organ or non-organ transplantation to reduce onset of transplantation rejection. Other embodiments related to treatment of a subject suspected of having or developing an inflammatory disorder where the inflammatory disorder includes one or more of macrophage, B cell or dendritic cell activation, Il-1, TNF-alpha (TNF-α) or induction of other proinflammatory cytokines. Some embodiments related to a subject at risk of developing or having an inflammatory lung disorder. Certain embodiments relate to compositions and methods including alpha-1 antitrypsin (AAT) or recombinant or fusion molecule thereof to reduce or prevent transplantation rejection or prepare a subject for organ or non-organ transplantation.

BACKGROUND

Serine Proteases

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine at the active site.

Naturally occurring serine protease inhibitors have been classified into families primarily on the basis of the disulfide bonding pattern and the sequence homology of the reactive site. Serine protease inhibitors, including the group known as serpins, have been found in microbes, in the tissues and fluids of plants, animals, insects and other organisms. At least nine separate, well-characterized proteins are now identified, which share the ability to inhibit the activity of various proteases. Several of the inhibitors have been grouped together, namely α1-antitrypsin-proteinase inhibitor, secretory leukocyte protease inhibitor or SLPI, antithrombin III, antichymotrypsin, C1-inhibitor, and α2-antiplasmin, which are directed against various serine proteases, e.g., leukocyte elastase, thrombin, cathepsin G, chymotrypsin, plasminogen activators, and plasmin. These inhibitors are members of the α1-antitrypsin-proteinase inhibitor class. The protein α2-macroglobulin inhibits members of all four classes of endogenous proteases: serine, cysteine, aspartic, and metalloproteases. However, other types of protease inhibitors are class specific. For example, the α1-antitrypsin-proteinase inhibitor (also known as (α1-antitrypsin or AAT) and inter-alpha-trypsin inhibitor inhibit only serine proteases, α1-cysteine protease inhibitor inhibits cysteine proteases, and α1-anticollagenase inhibits collagenolytic enzymes of the metalloenzyme class.

The normal plasma concentration of ATT ranges from 1.3 to 3.5 mg/ml although it can behave as an acute phase reactant and increase 3-4-fold during host response to inflammation and/or tissue injury such as with pregnancy, acute infection, and tumors. It easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen. ATT appears to represent an important part of the defense mechanism against activity by serine proteases.

AAT is one of few naturally occurring mammalian serine protease inhibitors currently approved for the clinical therapy of protease imbalance. Therapeutic α1-antitrypsin has been commercially available since the mid 1980's and is prepared by various purification methods (see for example Bollen et al., U.S. Pat. No. 4,629,567; Thompson et al., U.S. Pat. Nos. 4,760,130; 5,616,693; WO 98/56821). Prolastin is a trademark for a purified variant of α1-antitrypsin and is currently sold by Talectris Company (U.S. Pat. No. 5,610,285 Lebing et al., Mar. 11, 1997). Recombinant unmodified and mutant variants of AAT produced by genetic engineering methods are also known (U.S. Pat. No. 4,711,848); methods of use are also known, e.g., (AAT gene therapy/delivery (U.S. Pat. No. 5,399,346).

Graft Rejection

There are many diseases that culminate in organ dysfunction or failure. Representative non-limiting examples include renal failure due to diabetes melitus, hypertension, urinary output obstruction, drug-induced toxicity, or hypoperfusion, as well as cardiac dysfunction due to ischemic coronary artery disease, cardiomyopathy/infection, or valvulopathy. Pulmonary diseases include substantial damage due to chronic obstructive pulmonary disease (COPD, including chronic bronchitis and emphysema), AAT deficiency, cystic fibrosis, and interstitial fibrosis. Under certain conditions, the only therapeutic option for treatment of a subject may be organ transplantation. Pancreatic-islet transplantation provides diabetic patients with the an option for a tightly-controlled blood glucose level, as proven to be essential for prevention of diabetic complications. With respect to islets, post-transplant inflammation, which precedes immune rejection, is a critical determinant of graft survival. This early inflammation is mediated by cells other than the impending allospecific immune cells.

One challenge to therapeutic transplantation is the damaging effects of the host immune system on the transplant. MHC molecules exist on the surfaces of cells and the particular structures of MHC molecules are typically unique for each individual (with the exception of identical twins, where the MHC molecule complements are identical). The immune system is programmed to attack foreign or "non-self" MHC-bearing tissues. For these reasons, when an organ or tissue is transplanted into a recipient, an effort is made to optimize the degree of tissue matching between donor and recipient. MHC antigens are characterized for the recipient and donors. Matching a donor to an allograft recipient by MHC structure reduces the magnitude of the rejection response. An archetypal example is blood group matching. Most transplants are allografts that occur between non-identical members of the same species. Since these matches are imperfect, there is an expected graft rejection immune response associated with allografts. Current methods used, in order to enhance graft survival, include medications to suppress the immune response which can result in graft rejection. These medications are referred to immunosuppressant or antirejection drugs, such as prednisone, cyclosporine A, and cyclophosphamide, to name a few. As mentioned above, local inflammation is experienced immediately after grafting, and cells that are particularly sensitive to non-specific inflammation, such as islets, can endure graft dysfunction more severely than other types.

Despite advances in the field of antirejection therapy, graft maintenance remains a challenge since the available antirejection therapies are imperfect. For example, immunosuppression enhances the risk for opportunistic infection or neoplasia. Toxicities abound and include, but are not limited to, diabetes, organ dysfunction, renal failure, hepatic dysfunction, hematological defects, neuromuscular and psychiatric side effects, and many others. Therefore, there is a need for a more effective anti-rejection medical treatment that prolong graft survival and improve the quality of life.

Bone marrow transplantation is a unique kind of transplant where immune cells from a donor are transferred into a recipient, thereby conferring the donor immune system into the recipient. Here, the graft is capable of generating an immune response against the host, and this is termed "graft versus host" disease (GVHD). Immunosuppressive and anti-microbial treatment is required to block adverse consequences of GVHD, and a need exists for safer and more effective inhibitors of the adverse effects by the graft.

SUMMARY

Embodiments of the present invention provide for methods for pretreating or preparing a subject having or in need of an organ or non-organ transplant. In accordance with these embodiments, a subject may be administered a composition for reducing the risk of a transplant rejection or a side-effect of a transplant rejection in a subject prior to receiving the transplant.

In one aspect, the subject can be administered a composition including a compound that is capable of modulating transplant rejection. A composition of certain embodiments herein can be administered well before transplantation in order to prepare the subject for receiving transplantation. For example, compositions disclosed herein can be provided to a subject greater than 9 weeks, 3 month, 4 months, 5 months, up to 9 months, up to a year, up to 18 months or more prior to transplantation of the organ or implantation of the non-organ. In other embodiments, a subject can be treated for 3-10 weeks on a weekly or daily schedule or up to 18 months prior to transplantation and still benefit from the pre-treatment and reduced graph rejection. In certain embodiments, a subject waiting on a transplant list is a candidate for pre-treatment by compositions disclosed herein. Compositions contemplated can include, but are not limited to, AAT or cleavage product thereof or a fusion compound thereof or combination thereof using a predetermined regimen. These compositions can be administered to the subject while waiting for a transplant organ to be located or in preparation for transplantation surgery.

Some embodiments of the present invention relate to compositions and methods for pre-treatment of or preparing a subject for, organ or non-organ transplantation to reduce onset of transplantation rejection. Other embodiments related to treatment of a subject suspected of having or developing an inflammatory disorder where the inflammatory disorder includes one or more of macrophage, B cell or dendritic cell activation, Il-1, TNF-α or induction of other proinflammatory cytokines. Some embodiments related to a subject at risk of developing or having an inflammatory lung disorder. Certain embodiments relate to compositions and methods including alpha-1 antitrypsin (AAT) or recombinant or fusion molecule thereof to reduce or prevent transplantation rejection or onset of an inflammatory lung disorder.

In addition, the composition may further include one or more anti-transplant rejection agent, anti-inflammatory agent, immunosuppressive agent, immunomodulatory agent, anti-microbial agent (e.g. antibiotic or other), anti-viral agent, or a combination thereof.

An AAT molecule of a construct contemplated herein can be a naturally occurring alpha-1 antitrypsin (e.g. human), M-type or the most abundant form of AAT or other naturally-occurring form thereof, or fragments, or derivatives thereof, or mutant forms of AAT having no significant serine protease inhibitor activity, or alleles thereof (for example, there are approximately 100 naturally occurring AAT varients and any of these varients can be used in constructs disclosed herein), or analogs thereof or fusion protein thereof (e.g. a human IgG or fragment of human IgG). In accordance with these embodiments, a final construct may include 2 AAT constructs each associated with an immunological fragment (e.g. an Fc fragment) wherein the AAT-immune fragment constructs are linked together by disulfide bonds to form dual AAT-immune fragment constructs joined by one or more disulfide bonds. In certain methods disclosed herein, rapid purification of AAT- or AAT-peptide linked to an immune molecule significantly reduced inactivation of AAT activities and reduced time to purification. Rapid purification eliminates multiple purification steps while preserving critical activities of the constructs. For example, these rapidly purified fusion molecules are capable of retaining cytokine inhibiting functions, modulate immune and inflammatory molecule production compared to control plasma derived AAT (e.g. typical purification of naturally occurring AAT and purification of commercially available formulas). Significantly reduced concentrations of fusion molecules can be used to achieve the same or improved modulatory functions. Further, fusion molecules disclosed herein where an Fc region of AAT-Fc has a truncated hinge or deleted hinge region has superior activity when compared to plasma-derived AAT or fusion molecules of AAT-Fc with intact Fc.

In certain methods, AAT-Fc can include an intact AAT molecule linked on the carboxyterminus to Fc either through a linker or without a linking molecule. Linkers are well-known in the art and can range from a single amino acid to several amino acids. AAT-Fc molecules contemplated herein can be generated by any means known in the art. In certain embodiments, recombinant molecules can include a signal sequence in order to facilitate production and release of the fusion polypeptides. It is contemplated that any signal sequence can be used for any of the AAT-Fc fusion polypeptides wherein the signal sequence can be cleaved from the molecule once the fusion polypeptide is produced, if desired.

In accordance with these embodiments, a unit including two or more AAT-Fc (hinge deletion/truncation) constructs (or carboxyterminal AAT peptide fragments) can be purified and used in compositions and methods disclosed herein. Some of these embodiments of Fc-huAAT (hinge deletion) can be used in any method or composition contemplated herein. Other embodiments can include using IgG1, IgG2, IgG3 or IgG4 or IgD Fc fragments (hinge truncated or deleted) linked to an AAT molecule purified by rapid purification methods in order to preserve activity of the AAT molecule.

Certain embodiments disclosed herein concern using Protein A for a minimum step (e.g. one-step) purification of Fc-fusion constructs in order to avoid the deleterious effects of other methods and multiple steps as used in plasma AAT purification. Some embodiments herein concern preserving 85%, 90%, 95% or more AAT's anti-inflammatory activity in the fusion molecule compared to standard purifications used for commercially available products (e.g. Aralast™, Prolastin™) and/or compared to naturally-occurring AAT found in blood plasma. In some embodiments, fusion molecules of the instant application have demonstrated to be about 5, to about 10, to about 100, to about 1000 fold more active for reducing inflammation or to treat a condition compared to commercially available plasma-derived AAT formulations.

In other embodiments, AAT can include a carboxyterminal cleavage product of AAT including the carboxyterminal last 80 amino acids or peptide fragment thereof or fusion polypeptide thereof.

A transplant subject of some embodiments herein can include a subject receiving an organ transplant and/or a non-organ transplant or a skin graft or plastic surgery or cosmetic surgery. For example lung, kidney, heart, liver, cornea, skin, stem cells, soft tissue (e.g. facial component transplant, reconstructive surgery or plastic surgery), intestinal transplants, bone marrow, pancreatic islet, pancreas transplant or combination thereof are contemplated. Other transplant patents contemplated herein can include a subject receiving a reimplantation of a digit or a limb or a transplanted or artificial limb. Yet other embodiments contemplated herein, can concern a subject undergoing skin grafting procedures (e.g. a burn victim).

Some embodiments disclosed herein concern preventing onset of graft versus host disease (GVHD), or graft rejection in a subject. In one example, methods disclosed herein may be used to prepare a subject for bone marrow transplantation. Embodiments of the present invention provide methods for reducing graft rejection prior to onset.

Other embodiments concern reducing the need in a subject waiting for a transplant for immunosuppressive agents (e.g. provided to a subject before transplantation surgery) wherein compositions disclosed herein can be used to reduce side effects due to immunosuppressive agents such as compromised immune systems in a subject. Levels of immunosuppressive agents typically provided to a transplant patent can be reduced in light of use of AAT compositions described herein.

Certain embodiments provide for methods for controlling levels of proinflammatory cytokines in a subject prior to a transplantation event. In certain embodiments, TNFα (tumor necrosis factor alpha) expression and/or activity levels are controlled in a subject by administering a composition including one or more of alpha-1-antitrypsin, recombinant molecule thereof, fusion polypeptide thereof or peptide cleavage product thereof an analog thereof to the subject. In other embodiments, IL-6, IL-10, IFN-γ and other pro-inflammatory cytokines can be reduced or inhibited by a composition contemplated herein.

In certain embodiments, combination therapies can be used to prepare a subject for a transplantation event such as AAT or other related molecule in combination with an anti-inflammatory compound or reduced levels of immunomodulatory drug. Anti-inflammatory compounds or immunomodulatory drugs contemplated herein can include but are not limited to one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Embodiments of the present invention provide for methods for reducing graft rejection in a subject prior to receiving an organ or non-organ. In accordance with these embodiments, a subject may be treated with a composition disclosed herein at concentrations as low as 0.01 mg/kg (e.g. recombinant or fusion formulations of AAT) to about 10 mg/kg or from about 10 to about 250 mg/kg (e.g. AAT, commercially available formulation or naturally produced AAT). In other embodiments, a subject can be administered 60-120 mg/kg of plasma-derived AAT on a weekly basis for 1 month up to one year prior to transplantation. Fusion polypeptides can be reduced by about 2, 5, 10, 20, 50, to 100 fold or more depending on the formulation used.

In certain embodiments, AAT used in the methods and compositions herein can include, but is not limited to, naturally occurring AAT (394 AA, makes up about 90% of AAT derived from human platelets), Aralast™ (Baxter), Zemaira™ (Aventis Behring), Prolastin™ and Prolastin C™ (Talecris, N.C.), Aprotonin™ or Trasylol™ (Bayer Pharmaceutical Corporation) and Ulinistatin™ (Ono Pharmaceuticals, Inc.), Glassia™ (Kamada, Inc., Israel) or other commercial formulation or any combination thereof. In other embodiments, AAT or an AAT fragment or an AAT analog used in methods and compositions herein can include naturally occurring AAT or AAT fragment or analog or allele thereof.

In yet another embodiment, the present invention may include combination therapies including compositions exhibiting α1-antitrypsin, an analog thereof, or substance with serine protease inhibitor activity. For example, a composition may include α1-antitrypsin and another serine protease inhibitor administered simultaneously or in separate compositions.

In accordance with embodiments disclosed herein, any of the disclosed compositions may be used to prevent transplant rejection. Early onset signs of transplant rejection can be prevented that can include but are not limited to, infiltration of graft with dendritic, macrophage or B cells; reduced IL-1, TNF-α or other pro-inflammatory cytokines.

In certain embodiments, synthetic and/or naturally occurring peptides may be used in compositions and methods of the present invention for example, peptides having activities of intact AAT, such as carboxyterminal peptides of AAT.

In other embodiments, an agent that reduces the occurrence of graft rejection, promotes prolonged graft function or promotes prolonged allograft survival can also be an inhibitor of serine protease activity, an inhibitor of elastase, or an inhibitor of proteinase-3. An inhibitor of serine protease activity can include, but is not limited to, small organic molecules including naturally-occurring, synthetic, and biosynthetic molecules, small inorganic molecules including naturally-occurring and synthetic molecules, natural products including those produced by plants and fungi, peptides, variants of α1-antitrypsin, chemically modified peptides, and proteins.

In one aspect of the invention, the pharmaceutical compositions of the present invention are administered orally, systemically, via an implant, intravenously, topically, intrathecally, intratracheally, intracranially, subcutaneously, intravaginally, intraventricularly, intranasally such as inhalation, mixed with grafts by flushing of organ or suspension of cells, or any combination thereof.

As such, those skilled in the art will appreciate that the conception, upon which this disclosure is based, can readily be used as a basis for designing other methods for carrying out the several features and advantages of the present invention.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIGS. 2A-2C illustrate exemplary flow cytometry of particular cells including CD14+ and IL-1β-producing cells in AAT treated and AAT untreated subjects (A); and plots of frequencies of IL-1β expressing monocytes (B and C).

FIG. 6 illustrates certain subjects having Type 1 diabetes for less that one year observed in a clinical study.

FIG. 10 illustrates certain subjects having Type 1 diabetes for less that one year observed in a clinical study and how long they had T1D.

DESCRIPTION OF ILLUSTRATIVE EMBODIMENTS

Definitions

Figure 1A:
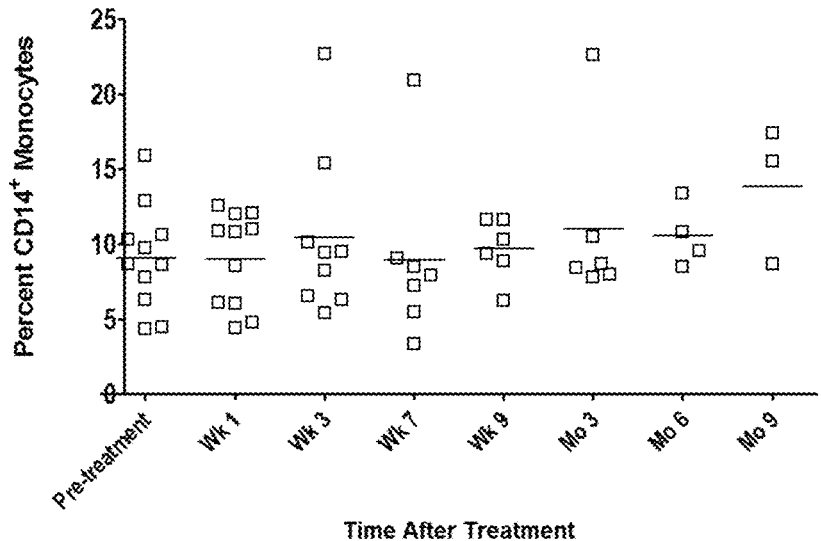
FIG. 1A-1C illustrates an exemplary regimen method of treating a subject with AAT and cellular infiltration of immune cells over time of certain embodiments herein, where (A) represents percent CD14+ cells; (B) represents percent CD1C+ cells and (C) represents percent CD304+ cells in a subject (e.g. using blood samples).

Terms that are not otherwise defined herein are used in accordance with their plain and ordinary meaning.

As used herein, "a" or "an" may mean one or more than one of an item.

It is to be understood that the terminology and phraseology employed herein are for the purpose of description and should not be regarded as limiting.

DETAILED DESCRIPTION OF THE INVENTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In certain embodiments well known methods or components have not been included in the description.

Embodiments of the present invention provide for methods for treating a subject having or in need of a transplant. In accordance with these embodiments, a subject may be treated with a composition capable of significantly reducing serine protease activity or other AAT activity. In addition, one embodiment of the present invention provides for methods including treating a subject with a composition comprising α-1-antitrypsin (AAT). In one embodiment, the composition can include α-1-antitrypsin or peptide cleavage product thereof. Further, the administration of the composition is provided in advance of transplantation in the subject. In addition, the composition may further include one or more additional therapies such as anti-inflammatory therapies. A transplant of the present invention may include transplantation of an organ such as lung, kidney, heart, liver, skin, stem cell, pancreas, or bowel organ or non-organ such bone marrow, pancreatic islet, cornea, and/or soft tissue.

Embodiments of the present invention provide for methods for promoting transplantation, graft survival, reducing graft rejection and/or reducing or preventing side-effects associated with graft rejection. In accordance with these embodiments, side-effects may include conditions associated with graft versus host disease (GVHD), or graft rejection. In one example, methods disclosed herein may be used to treat a subject undergoing bone marrow transplantation.

In accordance with these embodiments, a subject may be administered a composition for reducing the risk of a transplant rejection or a side-effect of a transplant rejection in a subject prior to receiving the transplant. In one aspect, the subject can be administered a composition including a compound that is capable of modulating transplant rejection. A composition of certain embodiments herein can be administered well before transplantation. For example, compositions disclosed herein can be provided to a subject greater than 9 weeks, 3 month, 4 months, 5 months, up to 9 months, up to a year, up to 18 months or more prior to transplantation of the organ or implantation of the non-organ. In other embodiments, a subject can be treated for a consecutive 3-10 weeks on a weekly or daily administration schedule up to 18 months prior to transplantation and still benefit from the pre-treatment and reduced graph rejection. In certain embodiments, a subject waiting on a transplant list is a candidate for pre-treatment by compositions disclosed herein. Compositions contemplated can include, but are not limited to, AAT or cleavage product thereof or a fusion compound thereof or combination thereof using a predetermined regimen. These compositions can be administered to the subject while waiting for a transplant organ to be located or in preparation for transplantation surgery.

Some embodiments of the present invention relate to compositions and methods for pre-treatment of or preparing a subject for, organ or non-organ transplantation to reduce onset of transplantation rejection. Other embodiments related to treatment of a subject suspected of having or developing an inflammatory disorder where the inflammatory disorder includes one or more of macrophage, B cell or dendritic cell activation, Il-1, TNF-alpha or induction of other proinflammatory cytokines. Some embodiments related to a subject at risk of developing or having an inflammatory lung disorder. Certain embodiments relate to compositions and methods including alpha-1 antitrypsin (AAT) or recombinant or fusion molecule thereof to reduce or prevent transplantation rejection or onset of an inflammatory lung disorder.

In certain embodiments, AAT used in the methods and compositions herein can include, but is not limited to, naturally occurring AAT (394 AA, makes up about 90% of AAT derived from human platelets), Aralast™ (Baxter), Zemaira™ (Aventis Behring), Prolastin™ and Prolastin C™ (Talecris, N.C.), Aprotonin™ or Trasylol™ (Bayer Pharmaceutical Corporation) and Ulinistatin™ (Ono Pharmaceuticals, Inc.), Glassia™ (Kamada, Inc., Israel) or other commercial formulation or any combination thereof. In other embodiments, AAT or an AAT fragment or an AAT analog used in methods and compositions herein can include naturally occurring AAT or AAT fragment or analog or allele thereof.

An AAT molecule of a construct contemplated herein can concern naturally occurring alpha-1 antitrypsin (e.g. human) or the most abundant form of AAT or other naturally-occurring form thereof, or fragments, or derivatives thereof, or mutant forms of AAT having no significant serine protease inhibitor activity, or alleles thereof (for example, there are approximately 100 naturally occurring AAT varients and any of these varients can be used in constructs disclosed herein), or analogs thereof or fusion protein thereof (e.g. a human IgG or fragment of human IgG). In accordance with these embodiments, a final construct may include 2 AAT constructs each associated with an immunological fragment (e.g. an Fc fragment) wherein the AAT-immune fragment constructs are linked together by disulfide bonds to form dual AAT-immune fragment constructs joined by one or more disulfide bonds. In certain methods disclosed herein, rapid purification of AAT- or AAT-peptide linked to an immune molecule significantly reduced inactivation of AAT activities and reduced time to purification. Rapid purification eliminates multiple purification steps while preserving critical activities of the constructs. For example, these rapidly purified fusion molecules are capable of retaining cytokine inhibiting functions, modulate immune and inflammatory molecule production compared to control plasma derived AAT (e.g. typical purification of naturally-occurring AAT and purification of commercially available formulas). Significantly reduced concentrations of fusion molecules can be used to achieve the same or improved modulatory functions. Further, fusion molecules disclosed herein where an Fc region of AAT-Fc has a truncated hinge or deleted hinge region has superior activity when compared to plasma-derived AAT or fusion molecules of AAT-Fc with intact Fc.

In accordance with these embodiments, a unit including two or more AAT-Fc (hinge deletion/truncation) constructs (or carboxyterminal AAT peptide fragments) can be purified and used in compositions and methods disclosed herein. Some of these embodiments of Fc-huAAT (hinge deletion) can be used in any method or composition contemplated herein. Other embodiments can include using IgG1, IgG2, IgG3 or IgG4 or IgD Fc fragments (hinge truncated or deleted) linked to an AAT molecule purified by rapid purification methods in order to preserve activity of the AAT molecule.

Certain embodiments disclosed herein concern using Protein A or other binding molecule for a minimum step (e.g. one-step) purification of Fc-fusion constructs in order to avoid the deleterious effects of other methods and multiple steps as used in plasma AAT purification. Some embodiments herein concern preserving 85%, 90%, 95% or more AAT's anti-inflammatory activity in the fusion molecule compared to standard purifications used for commercially available products (e.g. Aralast™, Prolastin™) and/or compared to naturally-occurring AAT found in blood plasma. In some embodiments, AAT fusion molecules of the instant application have demonstrated higher activity than the native to reduce inflammation or treat a condition compared to commercially available formulations. In other embodiments, AAT-Fc having a truncated or deleted hinge region of the Fc portion demonstrated superior activity in vivo to plasma-derived formulations.

In other embodiments, AAT can include a carboxyterminal cleavage product of AAT including the carboxyterminal last 80 amino acids or peptide fragment thereof.

A transplant subject of some embodiments herein can include a subject receiving an organ transplant and/or a non-organ transplant. For example, lung, kidney, heart, liver, cornea, skin, stem cells, soft tissue (e.g. facial component transplant or plastic surgery), intestinal transplants, bone marrow, pancreatic islet, pancreas transplant or combination thereof are contemplated. Other transplant patents contemplated herein can include a subject receiving a reimplantation of a digit or a limb or a transplanted or artificial limb. Yet other embodiments contemplated herein, can concern a subject undergoing skin grafting, repair or elected skin procedures (e.g. a burn victim, plastic surgery). In yet other embodiments, it is contemplated that subjects undergoing plastic surgery for facial or other body image changes (e.g. liposuction, breast implantation, face lifts etc.). In certain embodiments, a composition disclosed herein can be used before, during or after plastic surgery or skin grafting procedure or the like. In certain embodiments, a subject prepping for plastic surgery or other treatment can be administered a composition disclosed herein up to 1 year or even 18 months prior to plastic surgery. In other embodiments, a subject can be treated for about 3 months to about 9 weeks on a weekly or bi-weekly basis prior to the plastic surgery event or other regimen disclosed herein. In addition, a subject can be administered these compositions during and after a procedure.

Some embodiments disclosed herein concern preventing onset of graft versus host disease (GVHD) or graft rejection in a subject. In one example, methods disclosed herein may be used to prepare a subject for bone marrow transplantation. Embodiments of the present invention provide methods for reducing graft rejection prior to onset. For example, compositions administered to a subject about to receive an organ or non-organ transplantation can be administered an AAT composition in order to reduce events that lead to graft rejection.

Other embodiments herein concern reducing the need in a subject waiting for a transplant for immunosuppressive agents (e.g. provided to a subject before transplantation surgery). Compositions disclosed herein can be used to reduce side effects due to immunosuppressive agents such as compromised immune systems in a subject. Levels of immunosuppressive agents typically provided to a transplant patent can be reduced in light of use of AAT compositions described herein.

Certain embodiments provide for methods for controlling levels of proinflammatory cytokines in a subject prior to a transplantation event. In certain embodiments, TNFα (tumor necrosis factor alpha) expression and/or activity levels are controlled in a subject by administering a composition including one or more of alpha-1-antitrypsin, recombinant molecule thereof, fusion polypeptide thereof or peptide cleavage product thereof or an analog thereof to the subject.

In certain embodiments, combination therapies can be used to prepare a subject for a transplantation event such as AAT or other related molecule in combination with an anti-inflammatory compound or reduced levels of immunomodulatory drug. Anti-inflammatory compounds or immunomodulatory drugs contemplated herein can include but are not limited to one or more of interferon, interferon derivatives including betaseron, beta-interferon, prostane derivatives including iloprost, cicaprost; glucocorticoids including cortisol, prednisolone, methyl-prednisolone, dexamethasone; immunsuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Embodiments of the present invention provide for methods for reducing graft rejection in a subject prior to receiving an organ or non-organ transplantation. In accordance with these embodiments, a subject may be treated with a composition disclosed herein at concentrations as low as 0.01 mg/kg (e.g. recombinant or fusion formulations of AAT) or from about 10 to about 250 mg/kg (e.g. AAT, commercially available formulation or naturally produced AAT). In other embodiments, a subject can be administered 60-150 mg/kg of AAT or 80-120 mg/kg or higher on a weekly basis for greater than 9 weeks, to 3 months, to 6 months up to 18 months prior to transplantation.

In yet another embodiment, the present invention may include combination therapies including compositions exhibiting α1-antitrypsin, an analog thereof, or substance with serine protease inhibitor activity. For example, a composition may include α1-antitrypsin and another serine protease inhibitor administered simultaneously or in separate compositions.

In accordance with embodiments disclosed herein, any of the disclosed compositions may be used to prevent transplant rejection. Early onset signs of transplant rejection can be prevented that can include but are not limited to, infiltration of graft with dendritic, macrophage or B cells; reduced IL-1, TNF-α or other pro-inflammatory cytokines.

In certain embodiments, synthetic and/or naturally occurring peptides may be used in compositions and methods of the present invention for example, peptides having activities of intact AAT, such as the carboxyterminal peptides of AAT as presented herein. In addition, fusion polypeptides including for example, AAT or a carboxyterminal derivative thereof; and an immunoglobulin molecule are contemplated. In certain embodiments, AAT-fc can be included in a composition disclosed herein.

In one aspect of the invention, the pharmaceutical compositions of the present invention are administered orally, systemically, via an implant, intravenously, topically, intrathecally, intratracheally, intracranially, subcutaneously, intravaginally, intraventricularly, intranasally such as inhalation, or mixed with grafts by flushing of organ or suspension of cells, or any combination thereof. In certain embodiments, an organ or non-organ graft can be pre-treated with compositions disclosed herein in preparation for transplant or implantation Any of the embodiments detailed herein may further include one or more a therapeutically effective amount of anti-microbial drugs anti-inflammatory agent, immunomodulatory agent, or immunosuppressive agent or combination thereof.

Non-limiting examples of anti-rejection agents/drugs may include for example cyclosporine, azathioprine, corticosteroids, FK506 (tacrolimus), RS61443, mycophenolate mofetil, rapamycin (sirolimus), mizoribine, 15-deoxyspergualin, and/or leflunomide or any combination thereof.

In addition, other combination compositions of methods disclosed in the present invention can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. Antibody-based therapies may be used as induction therapy and/or anti-rejection drugs in combination with the compositions and methods of the present invention.

Embodiments of the present invention provide for methods treating a subject in need of an immunotolerance therapy. In accordance with these embodiments, a subject may be treated with a composition capable of significantly reducing serine protease activity. In one embodiment, the composition can include AAT, analog thereof or a serine protease inhibitor to for example, to reduce or inhibit the production of cytokines. In accordance with these embodiments, combination therapies are contemplated, such as combining AAT composition with an anti-inflammatory agent.

In one embodiment, the reduction, prevention or inhibition of rejection of transplantation or side effects thereof associated with one or more of each of the above-recited conditions may be about 10-20%, 30-40%, 50-60%, or more reduction or inhibition due to administration of the disclosed compositions.

In one embodiment of the present invention, a composition can include compounds that engage molecules for the SEC receptor to pre-treat a subject in need of a transplantation. In each of the recited methods, an α1-antitrypsin (e.g. mammalian derived) or inhibitor of serine protease activity substance contemplated for use within the methods can include a series of peptides including carboxyterminal amino acid peptides corresponding to AAT.

In one embodiment, a composition may include constructs for treating a subject in need of AAT therapy (e.g. mammalian derived AAT) for example, a series of peptides including carboxyterminal amino acid peptides corresponding to AAT and derivatives thereof. These peptides can include, pentapeptides including, FVFLM (SEQ ID NO:1), FVFAM (SEQ ID NO:2), FVALM (SEQ ID NO:3), FVFLA (SEQ ID NO:4), FLVFI (SEQ ID NO:5), FLMII (SEQ ID NO:6), FLFVL (SEQ ID NO:7), FLFVV (SEQ ID NO:8), FLFLI (SEQ ID NO:9), FLFFI (SEQ ID NO:10), FLMFI (SEQ ID NO:11), FMLLI (SEQ ID NO:12), FIIMI (SEQ ID NO:13), FLFCI (SEQ ID NO:14), FLFAV (SEQ ID NO:15), FVYLI (SEQ ID NO:16), FAFLM (SEQ ID: 17), AVFLM (SEQ ID NO:18), or combination thereof.

In other embodiments, AAT cleavage peptides contemplated for use in constructs, pharmaceutical compositions and methods herein are also intended to include any and all of those specific AAT peptides of SEQ ID NO:61, SEQ ID NO: 69 or SEQ ID NO:79 (naturally-occurring AAT of 394 amino acids, the most common form is the M type with subtypes M1, M2, M3 etc. are also contemplated herein) associated with the carboxyterminal amino acids. All AAT polypeptides are contemplated of use in methods disclosed herein, that possess anti-inflammatory activity and/or immune regulatory activity. Any combination of consecutive amino acids simulating AAT or AAT-like activity may be used, such as amino acids ranging from 315-394, amino acids ranging from 325-384, 358-394, 340-380 etc. In addition, combinations of consecutive amino acid sequences such as 5-mers, 10-mers, 15-mers, 20-mers, 25-mers, 30-mers, 35-mers etc. of the carboxyterminus can also be used. For example, any combinations of consecutive amino acids of 5-mers, 10-mers, 15-mers, 20-mers from SEQ ID NO:69 or 79 AAs 314-394 can be used in developing or purifying a construct contemplated herein.

Certain embodiments concern generating a recombinant fusion protein including linking an entire AAT molecule (e.g. SEQ ID NO: 61, 69 or 79) or a peptide molecule derived from the carboxyterminal amino acid region of AAT, to an IgG (e.g. Fc or mutant Fc for example, to reduce the hinge region) or fragment thereof. One common form of AAT is denoted by SEQ ID NO: 69. One construct contemplated herein is a full-length AAT, a leader sequence and an Fc portion/fragment of an immunoglobulin molecule. These constructs can be used in dimer form or as a monomeric fusion polypeptide form in compositions disclosed herein. In accordance with these embodiments, a pharmaceutically acceptable composition can include a dimer of AAT-Fc and/or a monomer of AAT-Fc or AAT cleaved from the Fc or combinations thereof, and a pharmaceutically acceptable excipient. In addition, point mutations or deletions can be made in the Fc region to reduce the flexibility of the hinge region and generate novel AAT-Fc molecules. In other embodiments, the hinge region of Fc derived from IgG1, IgG2, IgG3 or IgG4 can be deleted or truncated prior to linking an Fc to AAT or AAT peptide. Fc can be further manipulated to modify the region to reduce receptor interactions and enhance AAT-Fc construct activity. For example, point mutations can be made in the Fc region to reduce the flexibility of the hinge region or deletions or additions to this region can be made to affect secondary interactions regarding this region or that alter tertiary structure of the fusion molecule to generate novel AAT-Fc molecules.

In other embodiments, AAT protease binding domain can be mutated in order to reduce or eliminate the protease function of the molecule and not inhibit elastase activity; these molecules can be used in any construct contemplated herein such as an AAT-Fc mutant. In certain embodiments, a mutated AAT can be used to generate an AAT construct by methods disclosed herein. In other embodiments, a mutated molecule (e.g. having reduced or essentially no protease activity) retains its anti-inflammatory effects and/or immunomodulatory effects and can be used as an anti-inflammatory or immunomodulatory molecule in a subject having a need for such AAT therapy. One skilled in the art would understand a non-protease binding domain of AAT as well as what are termed the carboxyterminal last 80 amino acids of naturally-occurring AAT.

In each of the above-recited methods, AAT or carboxyterminal peptide derivatives thereof are contemplated for use in a composition herein. These peptide derivatives may include but are not limited to amino acid peptides containing the last 80 carboxyterminal derived amino acids of AAT, GITKVFSNGA (SEQ ID NO:105), DLSGVTEEAP (SEQ ID NO:106), LKLSKAVHKA (SEQ ID NO:107), VLTIDEKGTE (SEQ ID NO:108), AAGAMFLEAI (SEQ ID NO:109), PMSIPPEVKF (SEQ ID NO:110), NKPFVFLMIE (SEQ ID NO:111), QNTKSPLFMG (SEQ ID NO:112), KVVNPTQK (SEQ ID NO:113), LEAIPMSIPPE-VKFNKPFVFLM (SEQ ID NO:114); and LEAIPMSIPPE-VKFNKPFVF (SEQ ID NO:115), GADLSGVTEEAPLKL- SKAVHKA VLTIDEKGTEAAGAMFLEAIPMSIPPEVK-FNKPFVFLMIEQNTKSPLFMGKVVNPTQK (SEQ ID NO:90), SEQ ID NO:91 or any combination thereof. In certain embodiments, the carboxyterminal peptides of AAT are 80%, or 85%, or 90%, or 95%, or 99% identical to the naturally occurring M type amino acid sequence identified by SEQ ID NO. 33. In certain embodiments, about 3, or about 4, or about 5 amino acids can vary (e.g. point mutations) from an 80-mer from the carboxyterminal of the M type AAT sequence.

Certain embodiments include compositions of the fusion molecule SEQ ID NO: 32 or other Fc-AAT fusion molecule with or without an Fc hinge region where an Fc region originates from IgG1, IgG2, IgG3 or IgG4 or even IgD. In accordance with these embodiments, the compositions can be a pharmaceutical composition.

In accordance with embodiments of the present invention, the peptide can be protected or derivatized in by any means known in the art for example, N-terminal acylation, C-terminal amidation, cyclization, etc. In a specific embodiment, the N-terminus of the peptide is acetylated.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (e.g. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

Pharmaceutical compositions containing AAT or peptide fragment thereof, or analog thereof, or mutant thereof, or a functional derivative thereof (e.g. pharmaceutical chemical, protein, peptide of some of the embodiments) may be administered to a subject, for example by subcutaneous, intravenous, intracardiac, intracoronary, intramuscular, by oral administration, by inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the composition may be administered intranasally, such as inhalation. In other embodiments, a composition of the present invention can be administered intravenously once a month, bi-monthly, once a week or bi-weekly or other regimen as determined by a health professional.

A compound (e.g. a peptide, protein or mixture thereof) may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art. Solutions of the active compounds as free-base or pharmacologically acceptable salts can be prepared in water suitably mixed with a surfactant, such as hydroxypropylcellulose.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition such as daily, bi-weekly, weekly, bi-monthly etc. Pharmaceutical compositions are administered in an amount, and with a frequency, that is effective to modulate side effects. The precise dosage and duration of treatment may be determined empirically using known testing protocols or by testing the compositions in model systems known in the art and extrapolating therefrom. Dosages may also vary with the severity of the condition. In certain embodiments, the composition range can be between 0.01 and 250 mg/kg introduced daily or weekly or monthly to a subject. In certain embodiments, a plasma-derived AAT pharmaceutical composition disclosed herein can range from about 10 to about 150 mg/kg, to about 50 to about 120 mg/kg or other concentration as deemed appropriate by a health professional. In other embodiments, a recombinant or fusion polypeptide of AAT in a pharmaceutical composition can range from about 0.01 to about 50 mg/kg, to about 0.1 to about 10 mg/kg or other concentration as deemed appropriate by a health professional.

In another embodiment, nasal solutions or sprays, aerosols or inhalants may be used to deliver the compound of interest. Additional formulations that are suitable for other modes of administration may include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Liposomes or microparticles can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In some embodiments, pharmaceutical construct compositions concerns a construct derived from an AAT molecule having no significant serine protease inhibitor activity but having other AAT activity or analog thereof may be used in a single therapeutic dose, acute manner or a chronic manner to treat a subject. For example, a RCL mutant having no significant serine protease inhibition activity is contemplated.

In certain embodiments, compositions herein can be administered orally, systemically, via an implant, time released or slow-release compositions (e.g. gel, microparticles etc.), intravenously, topically, intrathecally, subcutaneously, by inhalation, nasally, or by other means known in the art or a combination thereof.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent.

Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. In addition, osmotic pumps may be used for administration. The necessary dosage will vary with the particular condition being treated, method of administration and rate of clearance of the molecule from the body.

In each of the aforementioned compositions and methods, a compound having serine protease inhibitor activity and/or having AAT activity or analog thereof may be used in a single therapeutic dose, acute manner or a chronic manner to treat episodes or prolonged bouts, respectively, in promoting graft survival, treating graft rejection and/or associated graft rejection-induced side-effects.

In certain embodiments of the methods of the present invention, the subject may be a mammal such as a human or a veterinary and/or a domesticated animal.

Therapeutic Methods

In one embodiment of the present invention, methods provide for treating a subject in need of a transplant. For example, treatments for reducing graft rejection, promoting graft survival, and promoting prolonged graft function by administering to a subject in need thereof a therapeutically effective amount of a composition.

Graft Rejection and Graft Survival-Side-Effects and Conditions

One of the beneficial effects of use of the compositions and methods of the present invention include, for example, and not by way of limitation, reduced infiltration of graft with cells or serum factors (including but not limited to, complement, anti-graft antibody that generate inflammation and graft rejection), reduced cytokines, reduced nitric oxide, reduced apoptosis, and reduced specific immune response against the graft or any combination thereof.

Isolated Proteins

One aspect of the invention pertains to proteins, and portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

Recombinant unmodified and mutant variants of AAT produced by genetic engineering methods are also known (see U.S. Pat. No. 4,711,848). The nucleotide sequence of human AAT and other human AAT variants has been disclosed. This nucleotide sequence may be used as starting material to generate all of the AAT amino acid variants and amino acid fragments depicted herein, using recombinant DNA techniques and methods known to those of skill in the art.

An isolated and/or purified or partially purified protein or recombinant protein or biologically active cleavage product thereof may be used in any embodiment of the invention. A protein that is substantially free of cellular material includes preparations of protein having less than about 30%, 20%, 10%, or 5% (by dry weight) of heterologous protein. When the protein or biologically active portion thereof is recombinantly produced, it can also be substantially free of culture medium. When the protein is produced by chemical synthesis, it is preferably substantially free of chemical precursors or other chemicals. Accordingly, such preparations of the protein have less than about 30%, 20%, 10%, and 5% (by dry weight) of chemical precursors or compounds other than the polypeptide of interest.

The compounds of the present invention can be used as therapeutic agents in the treatment of a physiological (especially pathological) condition caused in whole or part, by excessive serine protease activity. In addition, a physiological (especially pathological) condition can be inhibited in whole or part. Peptides contemplated herein may be administered as free peptides or pharmaceutically acceptable salts thereof. The peptides should be administered to individuals as a pharmaceutical composition, which, in most cases, will include the peptide and/or pharmaceutical salts thereof with a pharmaceutically acceptable carrier.

Other Fusion Polypeptides

In other embodiments, compounds having serine protease inhibitor activity such as AAT and/or analog thereof may be part of a fusion polypeptide. In one example, a fusion polypeptide may include α1-antitrypsin (e.g. mammalian α1-antitrypsin) or an analog thereof and a different amino acid sequence that may be heterologous to the AAT or analog substance.

In yet other embodiments, the fusion polypeptide contemplated for use in the methods of the present invention can additionally include an amino acid sequence that is useful for identifying, tracking or purifying the fusion polypeptide, e.g., a FLAG or HIS tag sequence. The fusion polypeptide can include a proteolytic cleavage site that can remove the heterologous amino acid sequence from the compound capable of serine protease inhibition, such as mammalian AAT or analog thereof.

In one embodiment, fusion polypeptides of the invention are produced by recombinant DNA techniques. Alternative to recombinant expression, a fusion polypeptide of the invention can be synthesized chemically using standard peptide synthesis techniques. The present invention also provides compositions that comprise a fusion polypeptide of the invention and a pharmaceutically acceptable carrier, excipient or diluent.

In yet another embodiment, AAT, analog thereof, or inhibitor of serine protease activity polypeptide fusion protein comprises a GST fusion protein in which is fused to the C-terminus of GST sequences. Fusion expression vectors and purification and detection means are known in the art.

Expression vectors can routinely be designed for expression of a fusion polypeptide of the invention in prokaryotic (e.g., *E. coli*) or eukaryotic cells (e.g., insect cells (using baculovirus expression vectors), yeast cells or mammalian cells) by means known in the art.

Expression of proteins in prokaryotes may be carried out by means known in the art. Such fusion vectors typically serve three purposes: 1) to increase expression of recombinant protein; 2) to increase the solubility of the recombinant protein; and 3) to aid in the purification of the recombinant protein by acting as a ligand in affinity purification.

In yet another embodiment, a nucleic acid of the invention is expressed in mammalian cells using a mammalian expression vector as described in the art. In another embodiment, the recombinant mammalian expression vector is capable of directing expression of the nucleic acid preferentially in a particular cell type (e.g., tissue-specific regulatory elements are used to express the nucleic acid) such as pancreas-specific promoters, and mammary gland-specific promoters. A host cell can be any prokaryotic (e.g., *E. coli*) or eukaryotic cell (e.g., insect cells, yeast or mammalian cells). Vector DNA can be introduced into prokaryotic or eukaryotic cells via conventional transformation or transfection techniques.

Combination Therapies

In each of the aforementioned methods of the present invention, the use of a compound capable of inhibiting serine protease or α1-antitrypsin or analog thereof alone or in combination with standard immunosuppressive agents enables transplantation of grafts into immunosuppressed or immunocompromised recipients. This combination therapy will expand the eligible patient population able to receive this form of treatment.

In each of the aforementioned aspects and embodiments of the invention, combination therapies other than those already enumerated above are also specifically contemplated herein. In particular, the compositions of the present invention may be administered with one or more macrolide or non-macrolide antibiotics, anti-bacterial agents, anti-fungals, anti-viral agents, and anti-parasitic agents. Examples of macrolide antibiotics that may be used in combination with the composition of the present invention include but are not limited to synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents include, but are not limited to, caspofungin, terbinafine hydrochloride, nystatin, and selenium sulfide.

Anti-viral agents include, but are not limited to, gancyclovir, acyclovir, valacylocir, amantadine hydrochloride, rimantadin and edoxudine Examples of macrolide antibiotics that may be used in combination with the composition of the present invention include but are not limited to synthetic, semi-synthetic or naturally occurring macrolidic antibiotic compounds: methymycin, neomethymycin, YC-17, litorin, TMP-SSX, erythromycin A to F, and oleandomycin. Examples of preferred erythromycin and erythromycin-like compounds include: erythromycin, clarithromycin, azithromycin, and troleandomycin.

Anti-parasitic agents include, but are not limited to, pirethrins/piperonyl butoxide, permethrin, iodoquinol, metronidazole, co-trimoxazole (sulfamethoxazole/trimethoprim), and pentamidine isethionate.

In another aspect, in the method of the present invention, one may, for example, supplement the composition by administration of a therapeutically effective amount of one or more an anti-inflammatory or immunomodulatory drugs or agents. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, (e.g., betaseron); prostane derivatives, (e.g., compounds disclosed in PCT/DE93/0013, iloprost, cortisol, dexamethasone; immunsuppressives, (e.g., cyclosporine A, FK-506 (mycophenylate mofetil); lipoxygenase inhibitors, (e.g., zileutone, MK-886, WY-50295); leukotriene antagonists, (e.g., compounds disclosed in DE 40091171 German patent application P 42 42 390.2); and analogs; peptide derivatives, (e.g., ACTH and analogs); soluble TNF-receptors; TNF-antibodies; soluble receptors of interleukins, other cytokines, T-cell-proteins; antibodies against receptors of interleukins, other cytokines, and T-cell-proteins.

Kits

In still further embodiments, the present invention concerns kits for use with the methods described above. Small molecules, proteins or peptides may be employed for use in any of the disclosed methods. In addition, other agents such as anti-bacterial agents, immunosuppressive agents, anti-inflammatory agents may be provided in the kit. The kits will thus include, in suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In one exemplary method, a study of Type 1 diabetes (T1D) was conducted to evaluate safety, therapeutic efficacy, and effect of alpha$_1$-antitrypsin (AAT) on certain innate immune functions in newly diagnosed patients with T1D. Twelve subjects were enrolled in this study. During the study, the subjects were infused with AAT at a dose of 80 mg/Kg body weight once a week for 8 weeks (other doses can be used for this process from about 60 to about 200 mg/kg). No adverse effect to AAT was observed during and after the treatment. It was observed that administration of AAT to the study subjects resulted in similar or increased area under the curve (AUC) c-peptide levels compared with the baseline in 4 individuals. Stable or increased c-peptide levels can be an indicator of stable or increased insulin production.

Figure 1B:
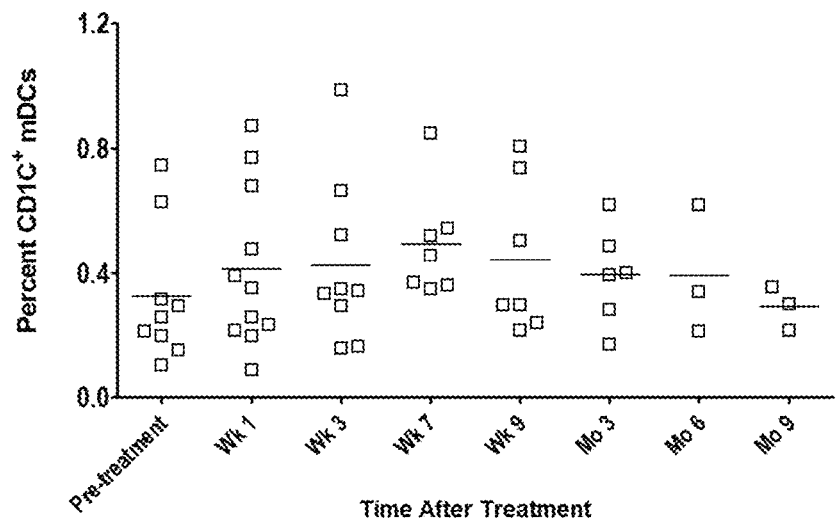
Figure 1C:
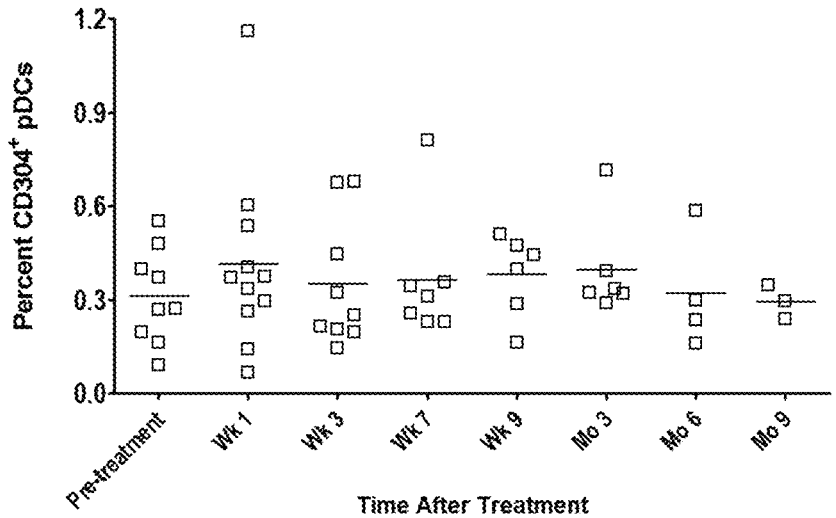

In certain exemplary methods, effects of AAT on beta cell function in a subject were assessed by analyzing proinflammatory cytokines pathways, and functions of innate immune cells including monocytes and dendritic cells (e.g. myeloid dendritic cells (mDCs) and plasmacytoid DCs (pDCs)). Blood samples were drawn prior to the subject undergoing AAT treatment (pre-treatment) and at weeks 1, 3, 7, 9 following AAT treatment. In addition, blood samples were drawn at months 3, 6, 9, 12, and 18 following AAT treatment of the subject. Effect of AAT therapy on monocytes and dendritic cell (DC) subset populations in peripheral blood from treated patients were analyzed. Peripheral blood mononuclear cells (PBMCs) were isolated from freshly drawn blood at different time points over the course and following AAT infusions in the subjects (n=3 to 11 per group). FIGS. 1A-1C represent exemplary graphs where monocytes, myeloid dendritic cells (mDCs) and plasmacytoid DCs (pDCs) were indicated and accounted for by staining of cell surface markers representative of the cells under analysis by identifying CD14$^+$ (FIG. 1A), CD1C$^+$ (FIG. 1B), and CD304$^+$ (FIG. 1C) markers on the cell surface, respectively. Similar frequencies of monocytes, mDCs, and pDCs were detected in blood from subjects prior to, during the course of AAT infusions and following the treatment. These observations support that AAT therapy does not alter the percentage of blood monocytes and dendritic cell subsets in the treated subjects prior and following the treatment.

Example 2

IL-1β Responses in Monocytes

Figure 2B:
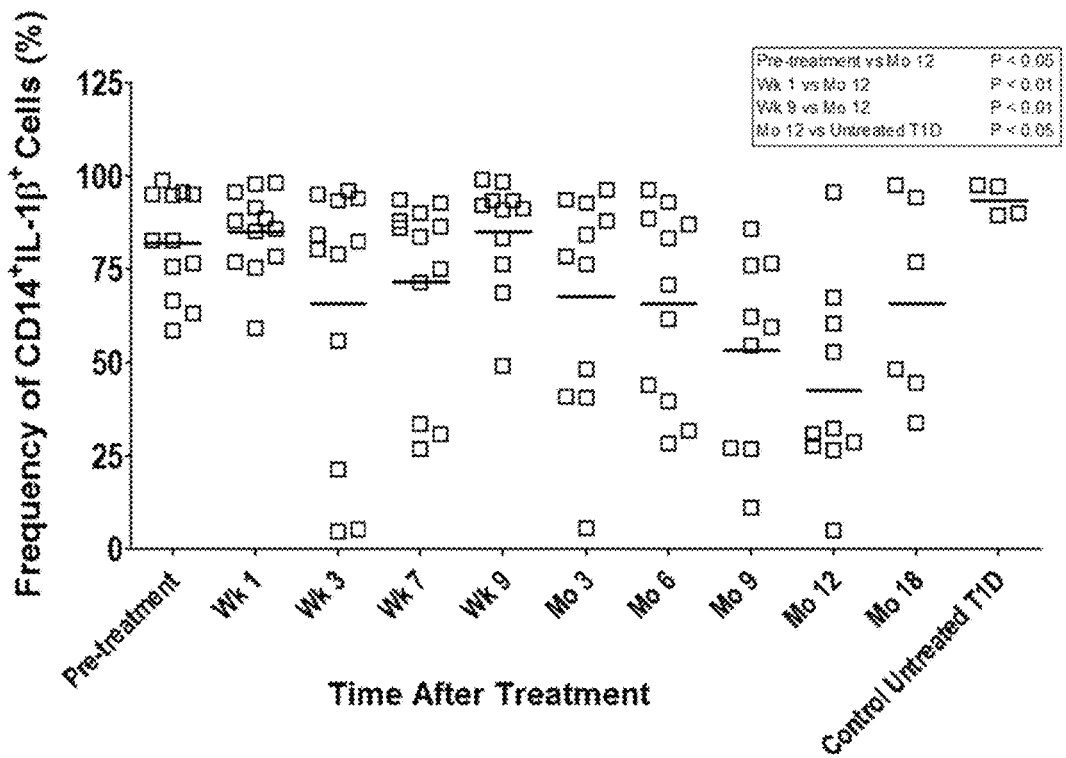
Figure 2C:
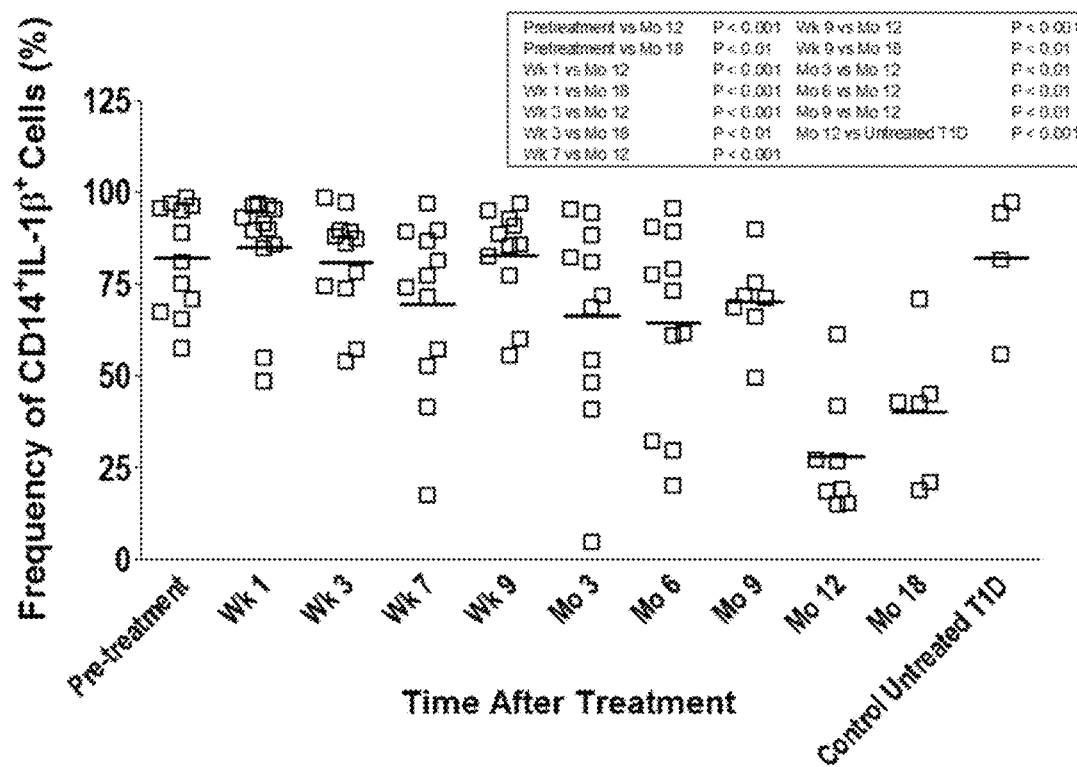

In another exemplary method, samples from subjects treated with AAT therapy were analyzed for effects of AAT on TLR-induced IL-1β responsiveness in peripheral monocytes. Primary PBMCs (Peripheral Blood Mononuclear Cells) from pretreated and AAT-administered subjects were obtained and cultured in vitro for 4 hours in the presence or absence of toll like receptor ligands (TLRs), (e.g. LPS (TLR4 ligand) or R848 (TLR7/8 ligand)). The harvested cells were analyzed by (FIG. 2A) flow cytometry to determine the proportion of IL-1β-producing monocytes and by frequency of CD14$^+$/IL-1β$^+$ cells (FIGS. 2B and 2C). FIGS. 2B-2C represent graphs illustrating frequencies of IL-1β expressing monocytes. Frequency of IL-1β expressing monocytes from untreated subjects cultured in the absence of TLR agonists was approximately 3% compared with 2.5-6.9% observed in the treated subjects (p>0.05, data not shown). Following LPS activation, an average of 82.0%±14.1 monocytes from the subjects expressed IL-1β (n=12) (see FIGS. 2A-2C). It was observed that IL-1β staining intensity was considerably lower in subjects 9 months following AAT treatment and the overall proportion of the IL-1β expressing monocytes in this population was significantly lower at 53.2%±26.0 (n=7) compared with subjects (p<0.05) prior to treatment, or subjects at 1 (n=12, p<0.01) and 9 weeks (n=11, p<0.01) following AAT therapy.

Therefore, it was proposed that subjects undergoing transplantation could be pretreated with AAT in order to reduce proinflammatory cytokine production greater than 9 weeks and to up to 18 months (or longer if determined by a health professional) prior to transplantation to prepare them for transplantation. LPS activation of PBMCs from a control, untreated subject group (n=4, with Type 1 diabetes), induced a similar frequency of IL-1β expressing monocytes compared with subject pre-treatment; and subjects at 12 month after treatment had reduced levels after LPS stimulation, (p<0.05 for both pretreated and 12 month treated individuals). The frequency of LPS-induced IL-1β expressing monocytes from subjects at 18 months following the treatment was increased reaching an intermediate level that was not significantly different from either AAT-treated or untreated subjects.

In another exemplary method, activation of PBMCs isolated from pretreated subjects, prior to AAT treatment, with TLR7/8 agonist R848 IL-1β in 82.3%±14.7 of the total monocytes was observed. (n=12). A two-fold reduction in the frequency of IL-1β expressing monocytes was observed in PBMCs from subjects at 12 and 18 months after treatment compared with the PBMCs from pretreated subjects prior to AAT treatment (see for example, FIG. 2C). Activation of PBMCs from control, untreated T1D subjects, with R848 induced IL-1β in 82.2%±19.0 of the total monocytes (p<0.001 compared with month 12 after treatment). This data indicated that AAT therapy can down-modulates or down-regulate TLR-induced IL-1β responses in peripheral monocytes.

AAT Down-Regulates TLR-Induced IL-1β Responses in mDCs

Figure 3A:
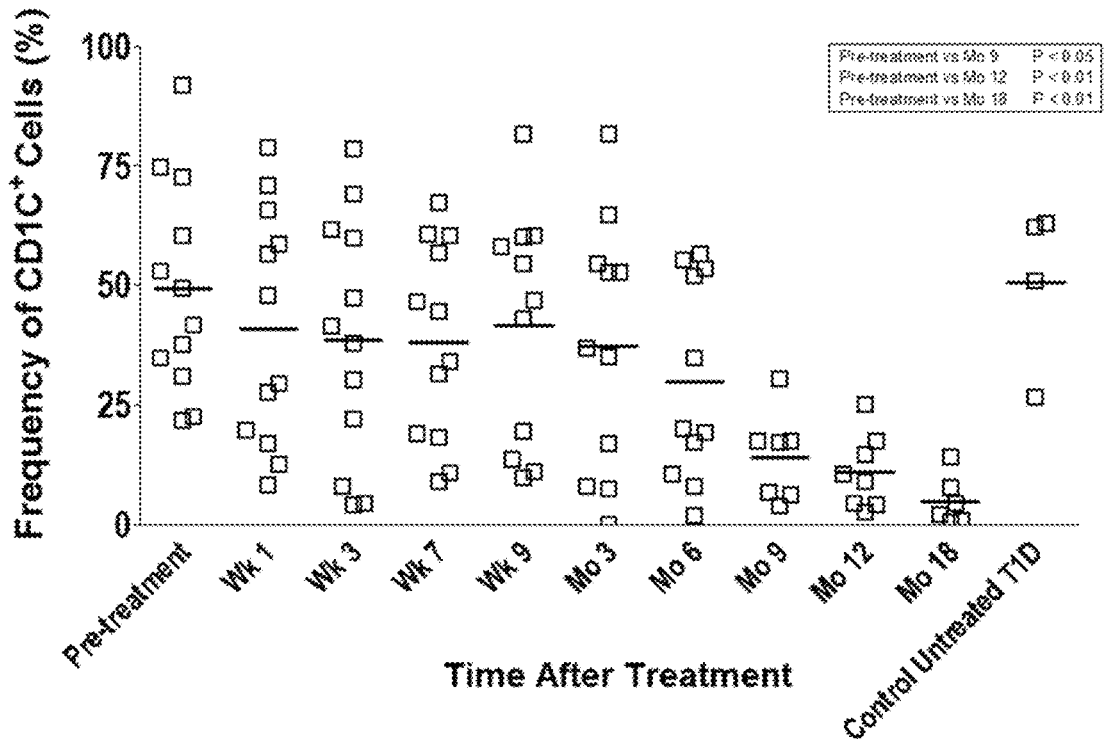
FIGS. 3A-3B illustrates frequencies of CD1C+ cells in subjects under various treatment regimens over pre-selected treatment periods.

Next, the effect of the AAT treatment on TLR-induced IL-1β expressing mDCs was analyzed. Primary PBMCs isolated from pre-treated subjects and AAT-infused subjects at different time points following the AAT treatment were cultured in the presence or absence of purified TLR agonists for 4 h and frequencies of IL-1β expressing mDCs were determined by flow cytometry. The proportion of non-activated resting mDCs expressing IL-1β in cultures from pretreated subjects was similar compared with individuals treated with AAT at any time point following AAT treatment (data not shown). For example, FIG. 3A illustrates that approximately 30-50% of mDCs isolated from pre-treated subjects and subjects treated with AAT at 1 week to 6 months following AAT treatment, expressed IL-1β following TLR4 ligation (n=11-12 per group). In contrast to this observation, the proportions of IL-1β expressing mDCs from AAT treated subjects at 9 months (n=8, p<0.05)), 12 (n=8, p<0.01) and 18 months (n=6, p<0.01) following AAT treatment was significantly reduced, to about 10-14% compared with the proportions of IL-1β expressing mDCs from subjects prior to AAT treatment. Activation of PBMCs from untreated T1D patients with LPS induced the expression of IL-1β in 50% of the total number of monocytes (n=4).

Figure 3B:
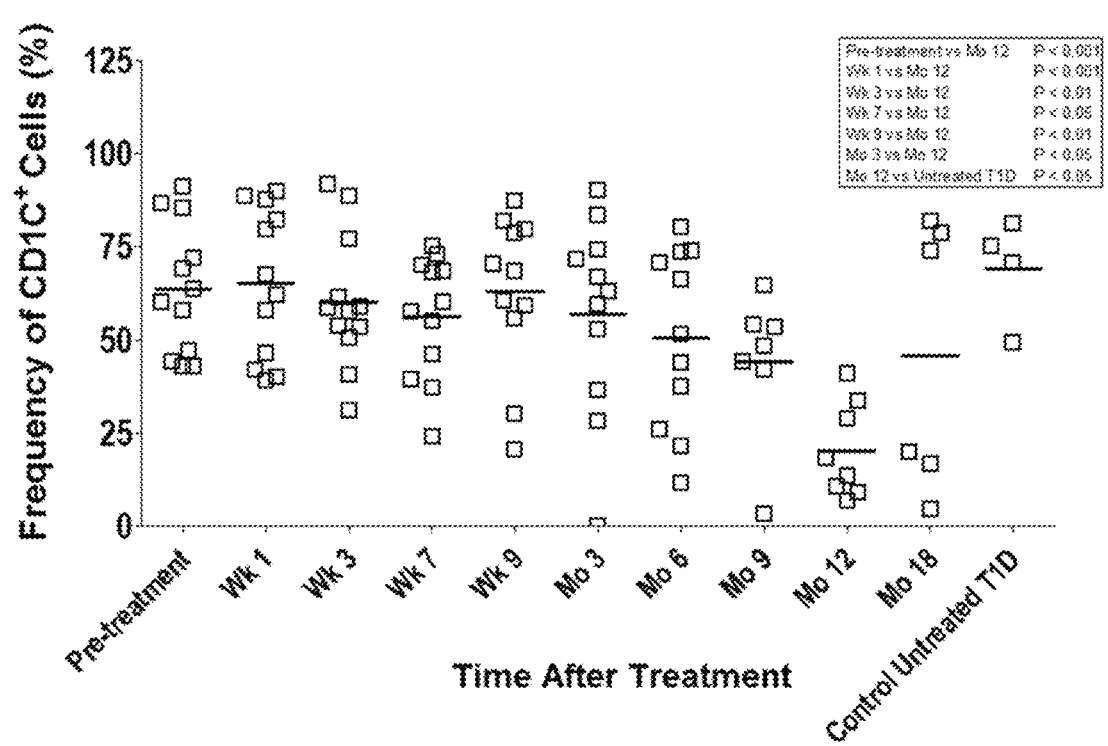

Activation of PBMCs with R848 led to IL-1β expression in 40-60% of the total mDCs in PBMCs from subjects prior to treatment, and from subjects treated with AAT at 1 week to 9 months following AAT administration. However, similar to LPS activation, a percentage of R848-induced IL-1β expressing mDCs from subjects at 12 months (n=8) following the AAT treatment was reduced to 20.2%±12.6, but this was significantly different when compared to pre-treated subjects (n=12), or when compared to 1 week to 9 months (n=7 to 12 per group) following AAT treatment (see FIG. 3B). Stimulation of primary PBMCs obtained from subjects 18 months after the treatment led to a slight increase in the frequency of IL-1β expressing mDCs compared with 12 months. Activation of PBMCs from control untreated T1D patients with R848 led to an increase in the expression of IL-1β expressing mDCs to 69.0%.±13.9% of the total monocytes (n=4, p<0.05 vs 12 months). These observations suggest that administration of AAT to a subject can down-regulate TLR-induced IL-1β responses in peripheral mDCs thus providing protection from adverse affects of pro-inflammatory cytokines.

Example 3

Correlation Between c-Peptide Levels and TLR-Induced IL-β Responses

Figure 4A:
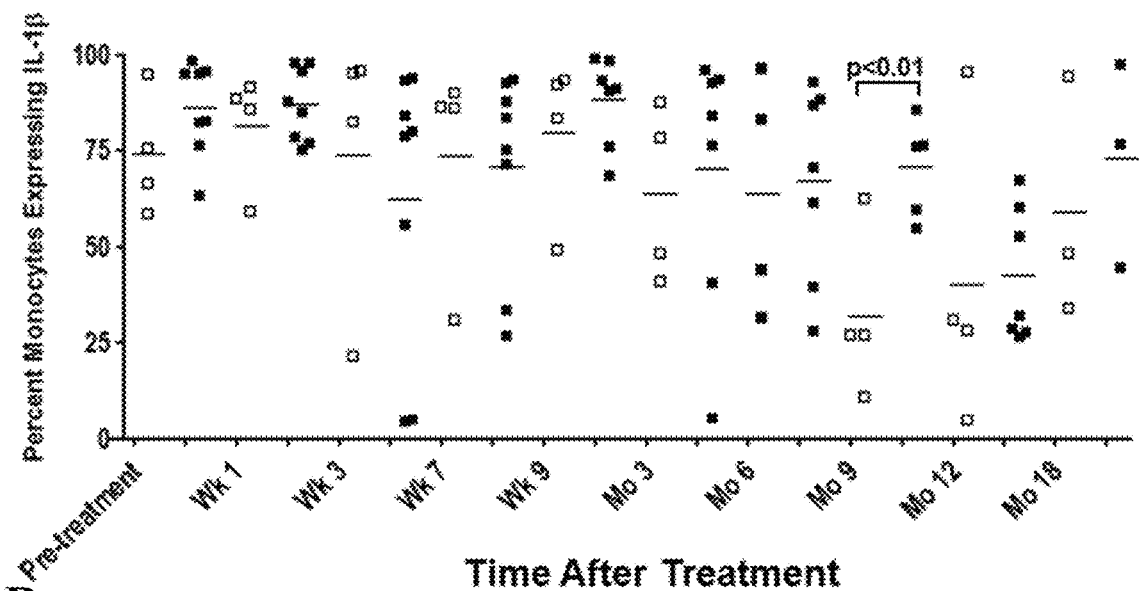
FIGS. 4A-4B illustrates frequencies of IL-1β-producing cells in subjects under various treatment regimens over pre-selected treatment periods.
Figure 4B:
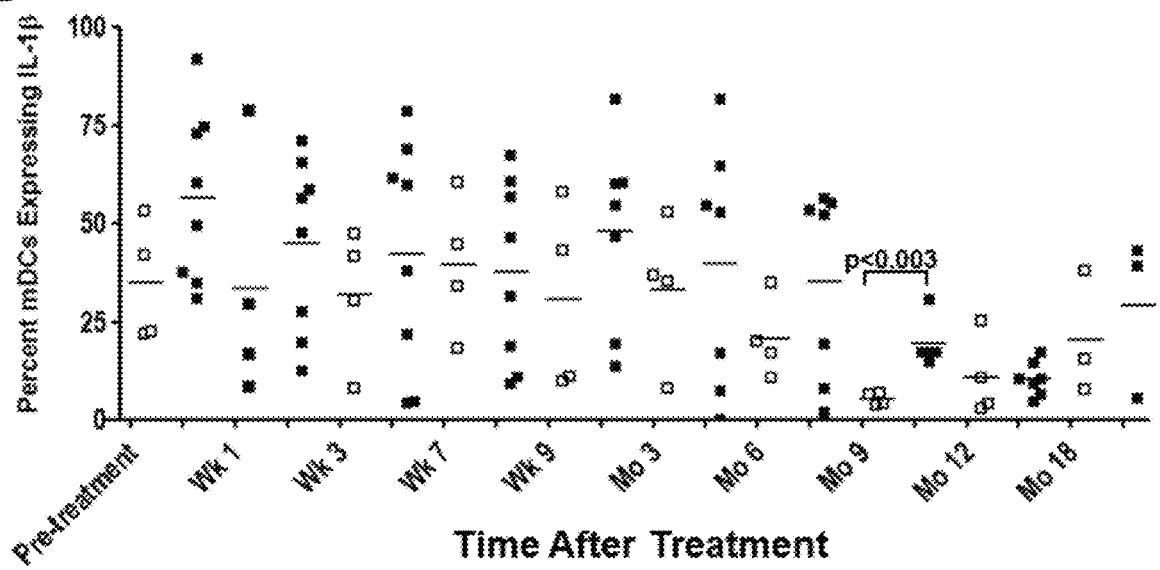

In another exemplary method, a study of whether c-peptide levels observed following the mixed meal tolerance test (MMT) correlate with the magnitude of the TLR-induced IL-1β response in monocytes and mDCs in the subjects. LPS-induced IL-1β responses from subjects were stratified into c-peptide responders (n=4) and non-responders (n=3 to 8 per group), and these groups were compared. See for example, FIGS. 4A-4B, which are graphic representations of this data where responders (open squares) are compared to non-responders (closed squares). AAT-treated subjects at 9 months following AAT treatment who demonstrated improved islet function had significantly lower levels of monocytes (FIG. 4A) and mDCs (FIG. 4B) expressing IL-1β compared to non-responders (p<0.01 for monocytes and p<0.003 for mDCs). A similar trend was observed regarding reduced frequencies of monocytes and mDCs expressing IL-1β following TLR7/8 ligation in subjects who had improved islet function compared with the non-responders (data not shown), though not statistically significant. These findings suggest that improved beta cell function following AAT therapy may be linked with a down-modulation in the TLR-induced IL-1 pathways in monocytes and mDCs.

Example 4

Serum Cytokine Levels

Figures 5A, 5B, 5C, 5D, 5E, 5F:
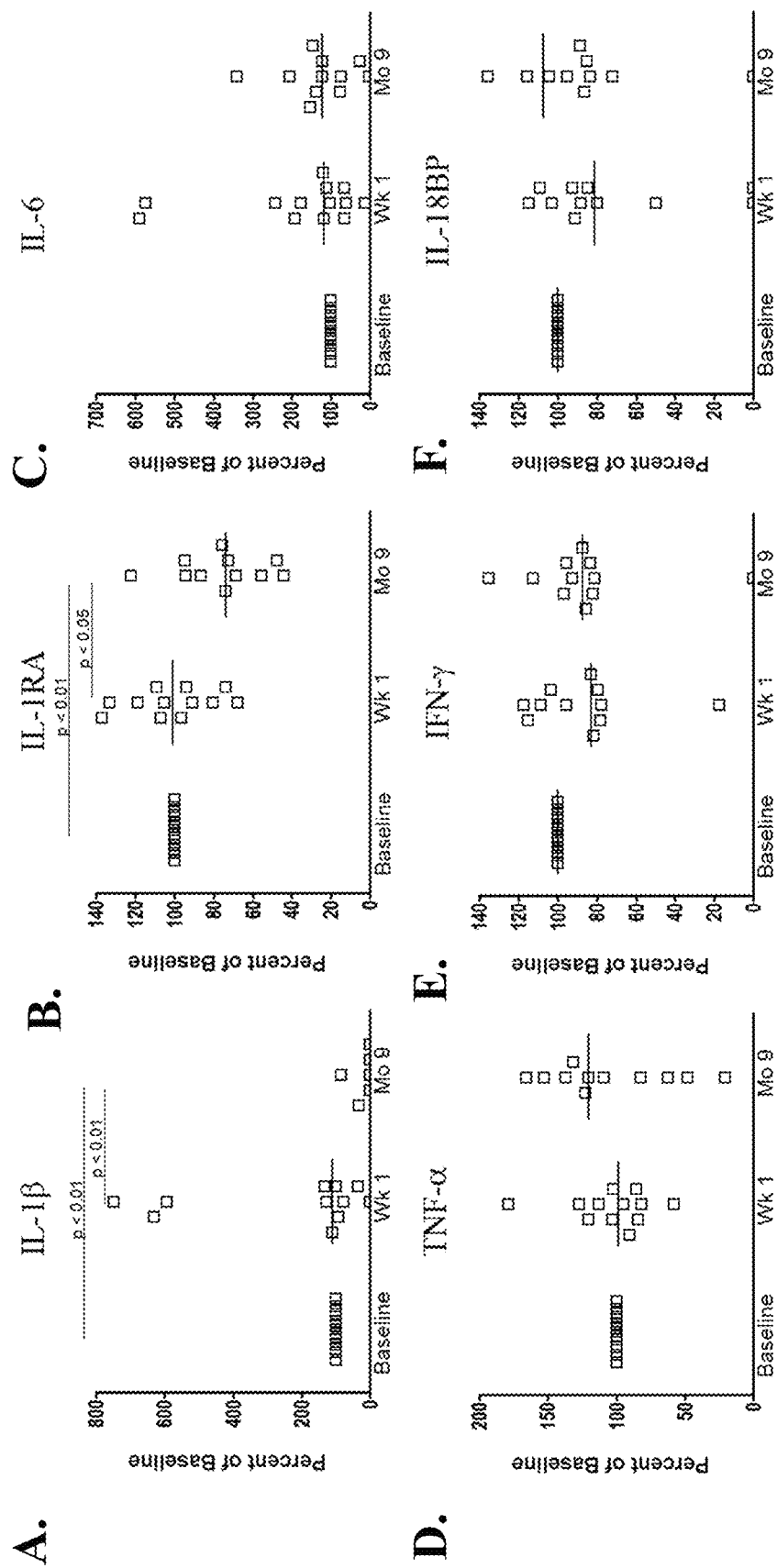
FIGS. 5A-5F illustrates the effect of AAT on various cytokine levels at various time points compared to baseline control levels of cytokine production.

In certain exemplary methods, levels of certain cytokines, for example, IL-1β, IL-1Rα, TNF-α, IL-6, IFN-γ, and IL-18BP in sera from subjects either pre-treatment or treated with AAT were analyzed. Due to the high degree of variability in an individual in the amount of cytokines in the blood, concentrations observed pretreatment for a subject was set for this study to be a baseline of 100% and cytokine levels observed in sera from treatment of the subjects were calculated as the percentage of this baseline as illustrated in the figures. In FIG. 5A, IL-1β data does not include any subject with IL-1β levels found to be below the detection limit. Data from this study represented in FIG. 5A illustrates that IL-1β levels in the serum from subjects 1 week after AAT treatment (n=12) was slightly increased compared with pretreatment baseline levels (n=12), but this difference may not be significant. However, it was observed that levels of IL-1β in the sera from treated subjects at 9 months following the treatment (n=5) were significantly reduced compared with the pretreated subjects (p<0.05) or subjects at 1 week following the AAT administration (p<0.01). Expression levels of IL-6 (FIG. 5C), TNF-α (FIG. 5D), IFN-γ (FIG. 5E), and IL-18BP (FIG. 5F) in sera from AAT treated subjects at 9 months were not found to be different compared with pretreated or 1 week treated individuals. Finally, little to no differences were observed in the amount of serum IL-1β and IL-1Rα in subjects with improved islet function. These observations support that AAT therapy can down-regulate IL-1β expression levels in the serum of subject pre-treated with AAT prior to embarking on a surgical procedure, plastic surgery or transplantation event.

Example 5

In one exemplary method, subjects are identified in need of a transplant. About 3 to up to 18 months prior to transplantation, a subject is treated for 2 to 12 weeks with a once a week to once daily administration of AAT (e.g. 60 to 150 mg/kg) or fusion polypeptide (0.1 to 10 mg/kg) composition thereof to reduce incidence of transplantation rejection.

Methods and Materials
Study Participants and AAT Study Protocol

Blood samples were drawn from subjects enrolled in the AAT study. Sera and PBMCs were isolated immediately after bloods had been drawn. The study was approved by an Institutional Review Board (IRB).

The subject cohort treated with AAT included 12 subjects with T1D (Table 1). The average age of the treated cohort was 24.6±10.5 years (range, 12-39 years; 4 females and 8 males) with an average BMI of 23.3±3.7 and average disease duration of 15.7±14.9 months (range, 3-44 months). Subjects were infused with 80 mg/Kg (doses up to 200 mg/kg can be used) body weight of AAT once a week for 8 weeks. Blood samples were drawn prior to the treatment and at weeks 1, 3, 7, 9, and months 3, 6, 9, 12, and 18 following the treatment. For flow cytometry analyses, a cohort of 4 patients with T1D was used at an average age of 18.8±3.6 years (range, 16-25 years, 3 males and 1 female) and BMI of 24.1±3.2 as a control untreated group with a similar disease duration to that of the treated cohort. The average disease duration in the positive control group was 17.3±4.3 months (range, 12-23 months).

PBMC Isolation

PBMCs were freshly isolated by Ficoll-Hypaque Plus density centrifugation (GE Health Care, Sweden) of freshly drawn heparinized blood from autoantibody positive and autoantibody negative subjects. PBMCs were washed twice with PBS (Invitrogen Life Technologies) and resuspended in endotoxin-free high glucose DMEM containing 2 mM L-glutamine, and 100 U/ml penicillin/streptomycin (both from Invitrogen Life Technologies), and 10% AB serum (PAA Laboratories, New Bedford, Mass.). For flow cytometry analyses, PBMCs were washed and resuspended in FACS buffer consisting of PBS (Invitrogen Life Technologies) plus 1% BSA and 0.05% Sodium azide (both from Sigma-Aldrich).

TABLE 1

Characteristics of Study Participants

| Gender | Age | BMI | T1D Duration (wk) | Basal HbA1c |
|---|---|---|---|---|
| Male | 39 | 24.3 | 7 | 5.2 |
| Female | 39 | 19.6 | 44 | 6.9 |
| Female | 33 | 23 | 4 | 6.8 |
| Male | 20 | 28.4 | 40 | 6.3 |
| Female | 22 | 20.2 | 21 | 5.9 |
| Male | 30 | 31.3 | 30 | 6.2 |
| Male | 38 | 25.4 | 9 | 6.1 |
| Male | 18 | 25.2 | 17 | 5.8 |
| Female | 15 | 20.7 | 3 | 6.3 |
| Male | 14 | 21.5 | 5 | 6.5 |
| Male | 15 | 20.1 | 5 | 6.1 |
| Male | 12 | 20.1 | 3 | 6.4 |

Analysis of DC and Monocyte Frequencies in the Peripheral Blood

For mDC enumeration, the following antibodies were used: APC-conjugated anti CD1C (mouse IgG2a, clone AD5-8E7, Miltenyi Biotech) plus APC-Alexa Fluor 750-conjugated anti-CD19 (mouse IgG1, clone HIB19, eBioscience, San Diego, Calif.). Staining with anti-CD19 was performed to exclude B cells expressing CD1C. For monocyte staining, pacific blue-conjugated anti-CD14 mAb (mouse IgG2a, clone M5E2, BioLegend, San Diego, Calif.) were used. For pDC subset staining, cells were surface stained with PE-conjugated mAb directed against $CD304^+$ (mouse IgG1, clone AD5-17F6, Miltenyi Biotech, Auburn, Calif.).

Activation of PBMCs with TLR Ligands and Intracellular Cytokine and Chemokine Staining Peripheral blood mononuclear cells were added to a 96-well round-bottom microtiter plates at a concentration of $1 \times 10^6$/well in a total volume of 100 μl. For intracellular cytokine analysis, PBMCs were incubated in the presence or absence of various purified TLR ligands and 1 μl/ml of Brefeldin A (BD Biosciences, San Diego, Calif.) for 4 h, followed by staining for surface markers and intracellular cytokines. For intracellular cytokine staining, PBMCs were cultured in the presence or absence of 100 ng/ml ultrapurified LPS (O111:B4, from Invivogen, San Diego, Calif.), and 10 ng/ml R848 (Axxora, San Diego, Calif.) for 4 hours followed by staining for DC and monocyte surface markers followed by staining for IL-1β and IL-6, previously published. TLR ligands were dissolved in Dulbecco's PBS and stored in aliquots at −20° C. until use.

Serum Cytokine Expression Levels

Approximately 50 μl of serum was used for measuring levels of IL-1β, IL-1 receptor antagonist (IL-IRA), TNF-α, IL-6, IFN-γ, and IL-18BP, using Mosaic™ ELISA Human Cytokine kits from R&D Systems (Minneapolis, Minn.). The detection sensitivity limits for these cytokines are as follows (in pg/ml): 0.11, 0.34, 0.76, 0.21, 0.77, and 0.26, respectively. The plates were read using the Quantus Imager, Logan, Utah.

Statistical Analyses

Statistical differences in frequencies of freshly drawn mDCs, pDCs and monocytes, frequencies of monocytes and mDCs expressing cytokines following TLR ligation, and serum cytokine expression levels were evaluated using ANOVA. Comparisons between two samples were performed using the unpaired t-test. P values <0.05 were considered to be statistically significant.

FIG. 6 illustrates certain subjects having Type 1 diabetes for less that one year observed in a clinical study. Subjects were administered AAT at 80 mg/kg i.v. weekly for 8 weeks. In certain embodiments, a subject can be treated by this regimen and then up to 6 months, up to one year or up to 18 months or more later, can receive an organ or non-organ implantation or transplantation.

Figure 7:
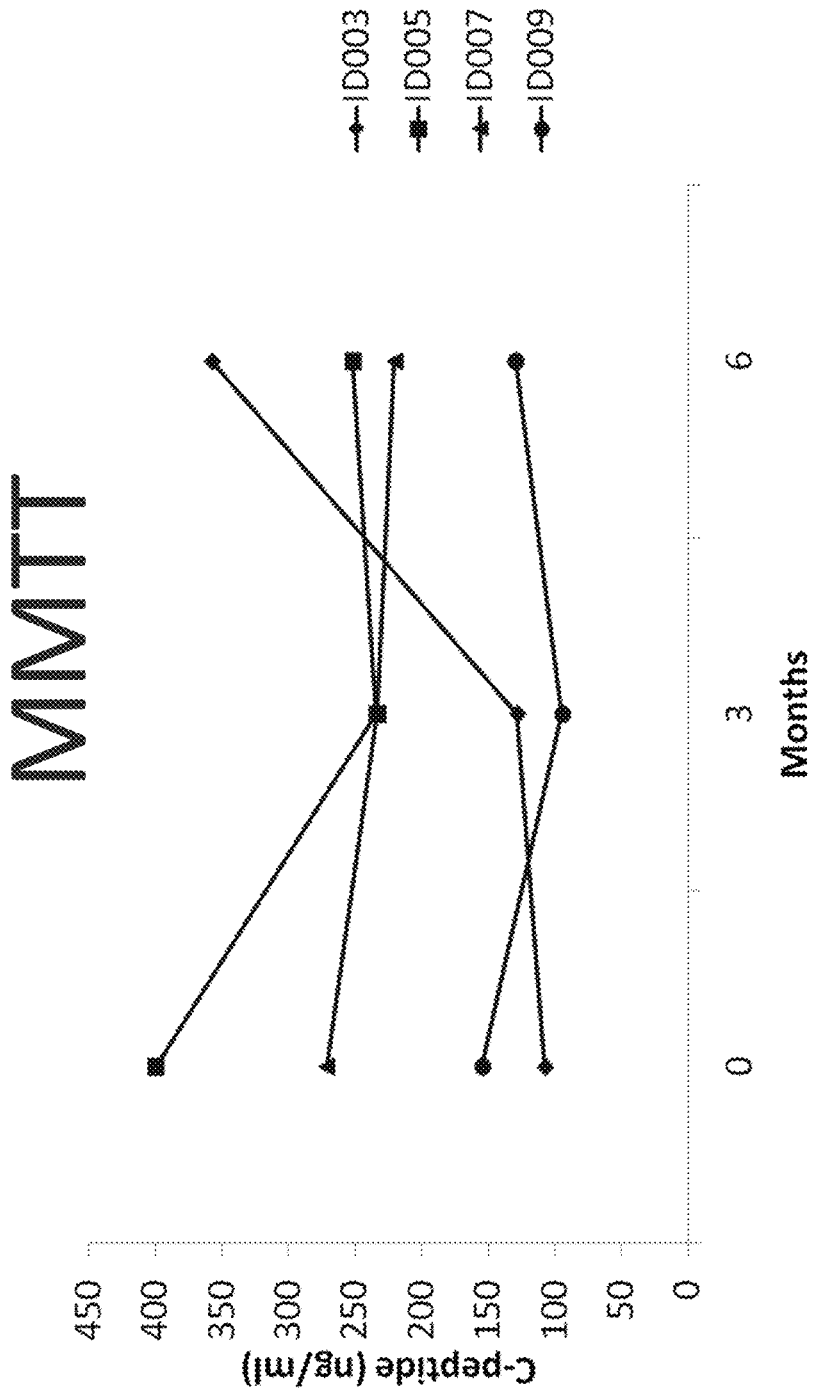
FIG. 7 represents a graph of C-peptide levels over time after a 2 hour mixed meal tolerance test (MMTT).

FIG. 7 represents a graph of C-peptide levels over time after a 2 hour mixed meal tolerance test (MMTT). This graph represents levels of C-peptide in subject examined herein. Type-1 diabetics typically have a reduced level of c-peptide.

Figure 8:
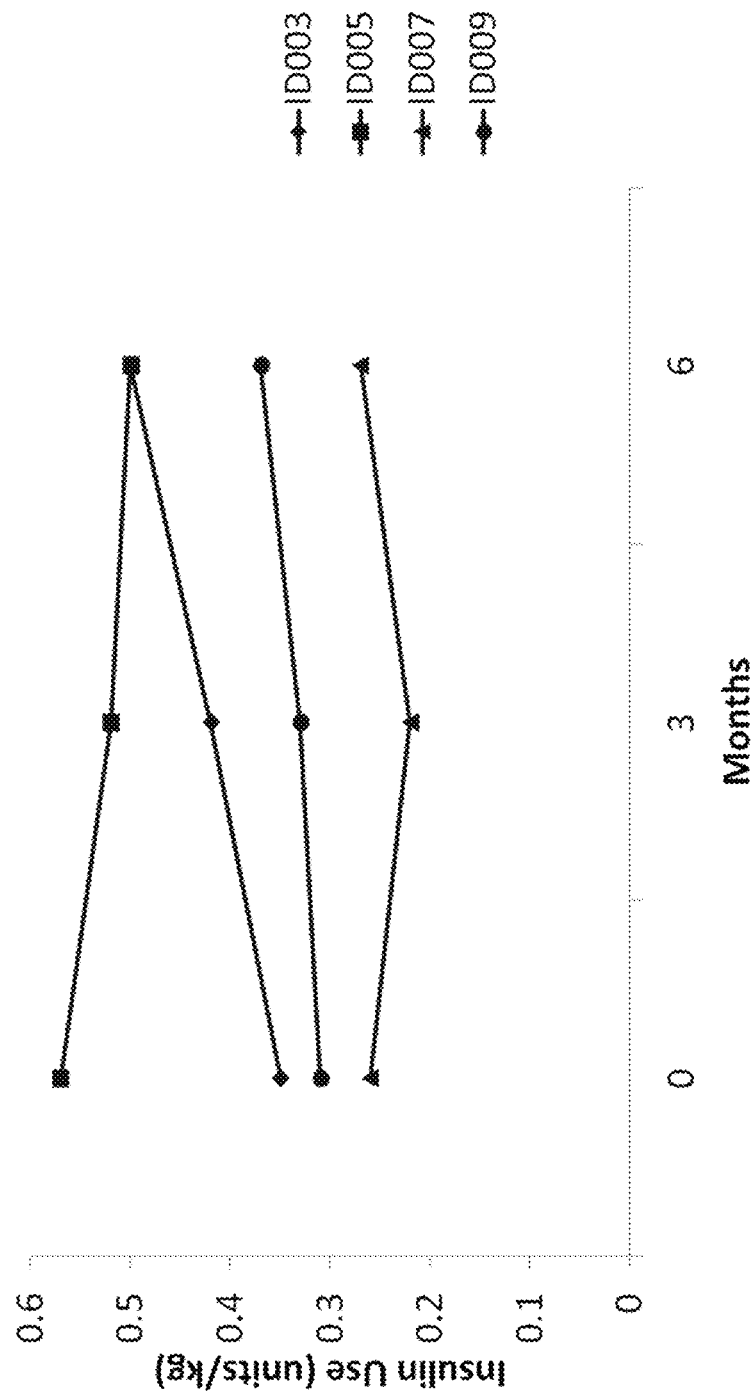
FIG. 8 represents a graph of insulin use over time in various T1D subjects monitored.

FIG. 8 represents a graph of insulin use over time in various T1D subjects monitored. The use of insulin in T1D subjects is typically for the rest of the subject's life.

Figure 9:
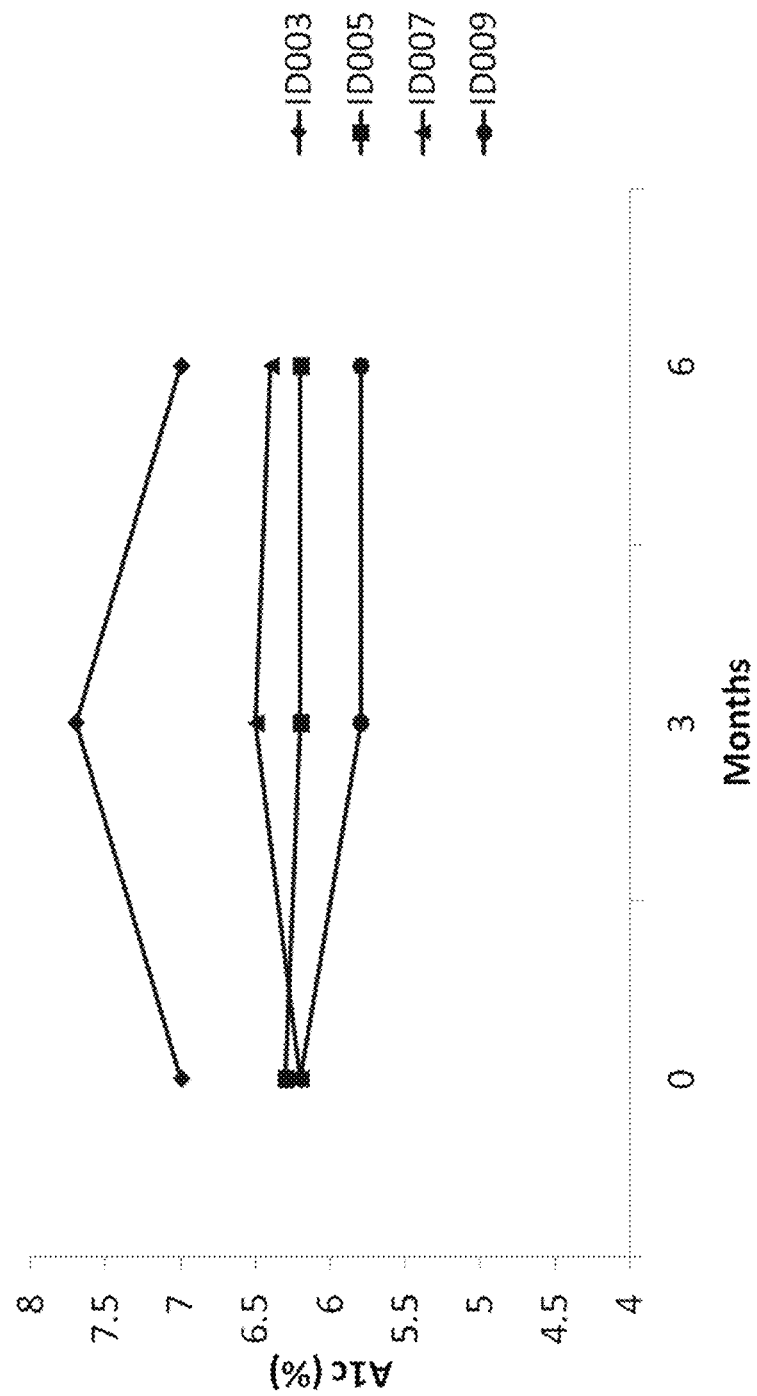
FIG. 9 represents a graph of glycemic control in various T1D subjects monitored.

FIG. 9 represents a graph of glycemic control in various T1D subjects monitored. This graph represents how the level of A1c is typically steady in these patients.

FIG. 10 illustrates a table of certain subjects having Type 1 diabetes for less that one year observed in a clinical study and how long they had T1D.

Figure 11:
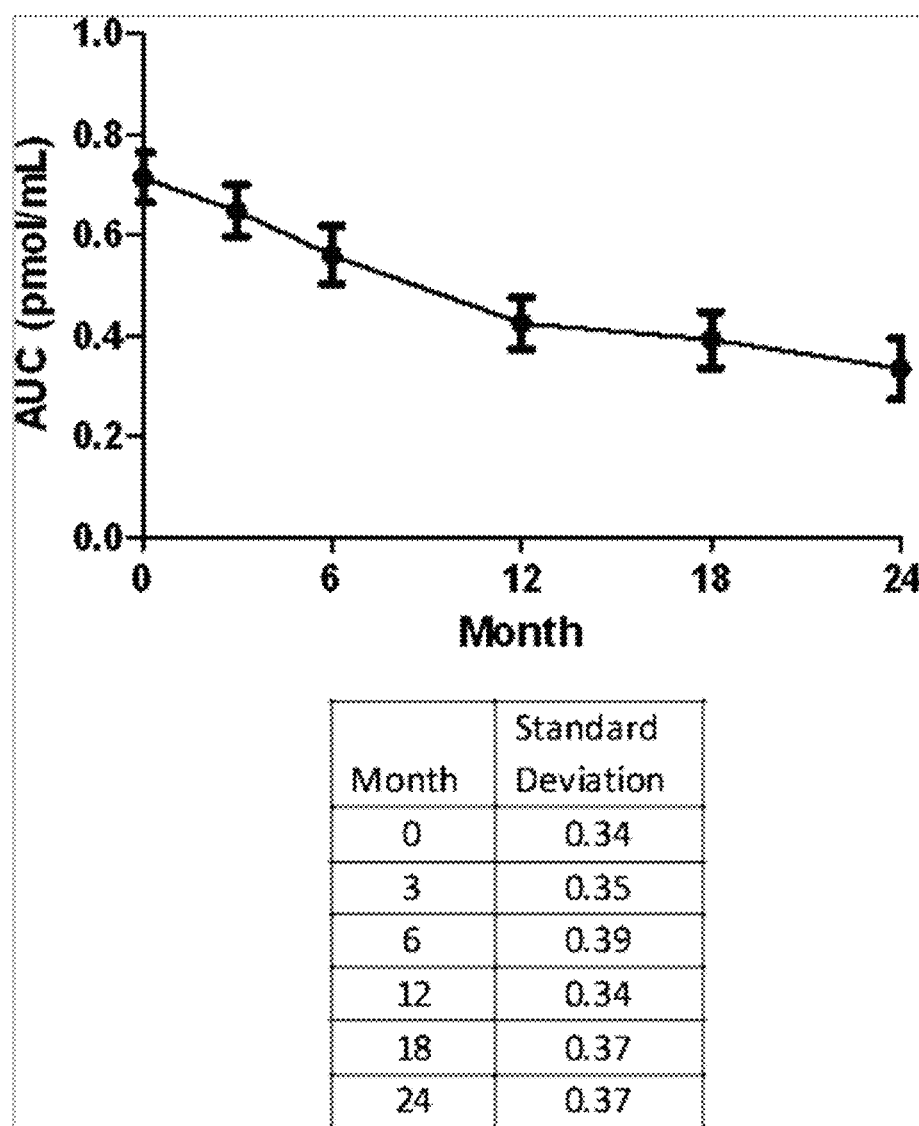
FIG. 11 illustrates c-peptide levels in control T1D subjects over time.

FIG. 11 illustrates a decline in c-peptide levels in control (untreated) T1D subjects over time.

Figure 12:
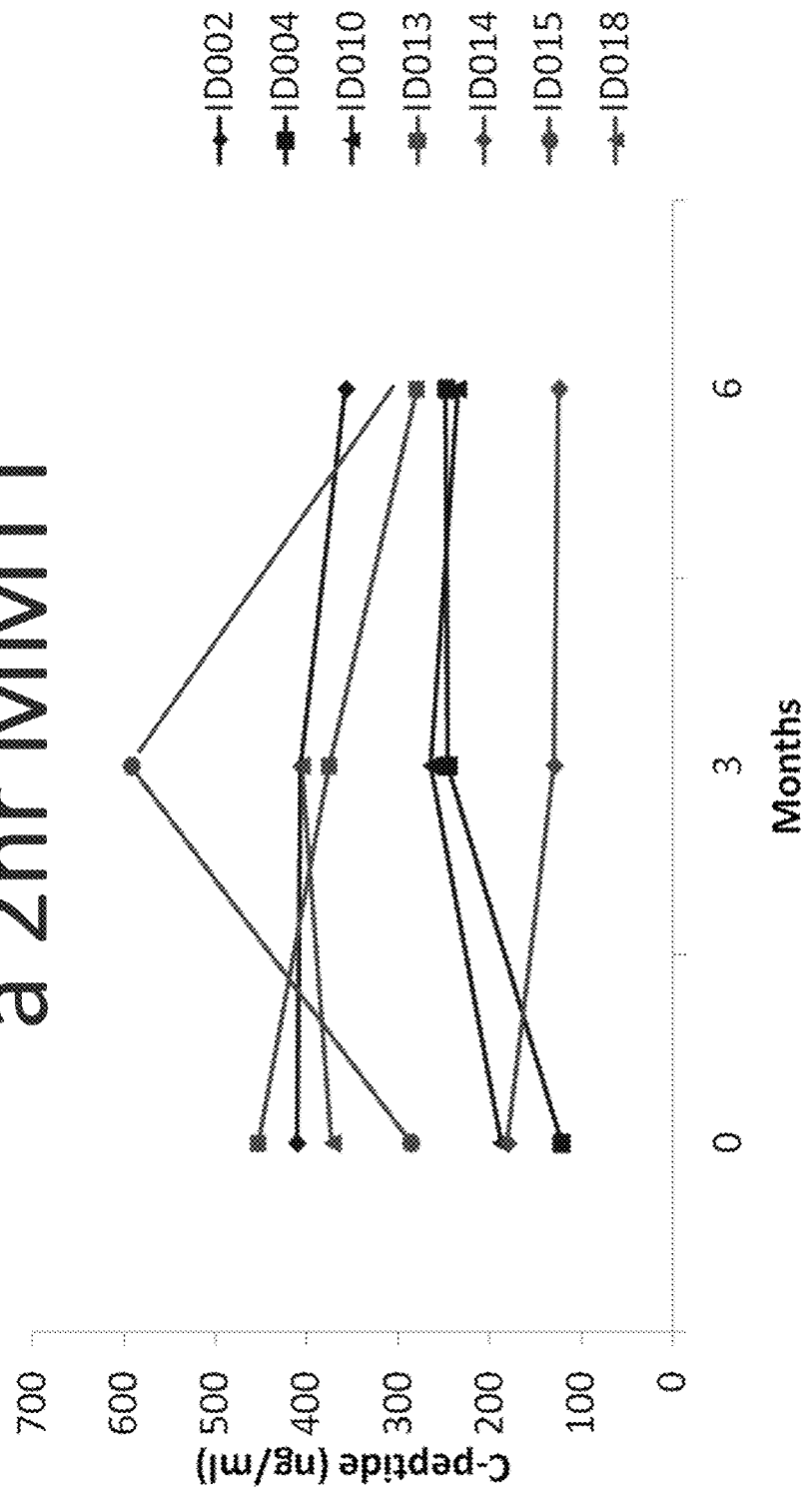
FIG. 12 represents a graph of C-peptide levels over time after a 2 hour mixed meal tolerance test (MMTT) in T1D subjects.

FIG. 12 represents a graph of C-peptide levels over time after a 2 hour mixed meal tolerance test (MMTT) in T1D subjects.

Figure 13:
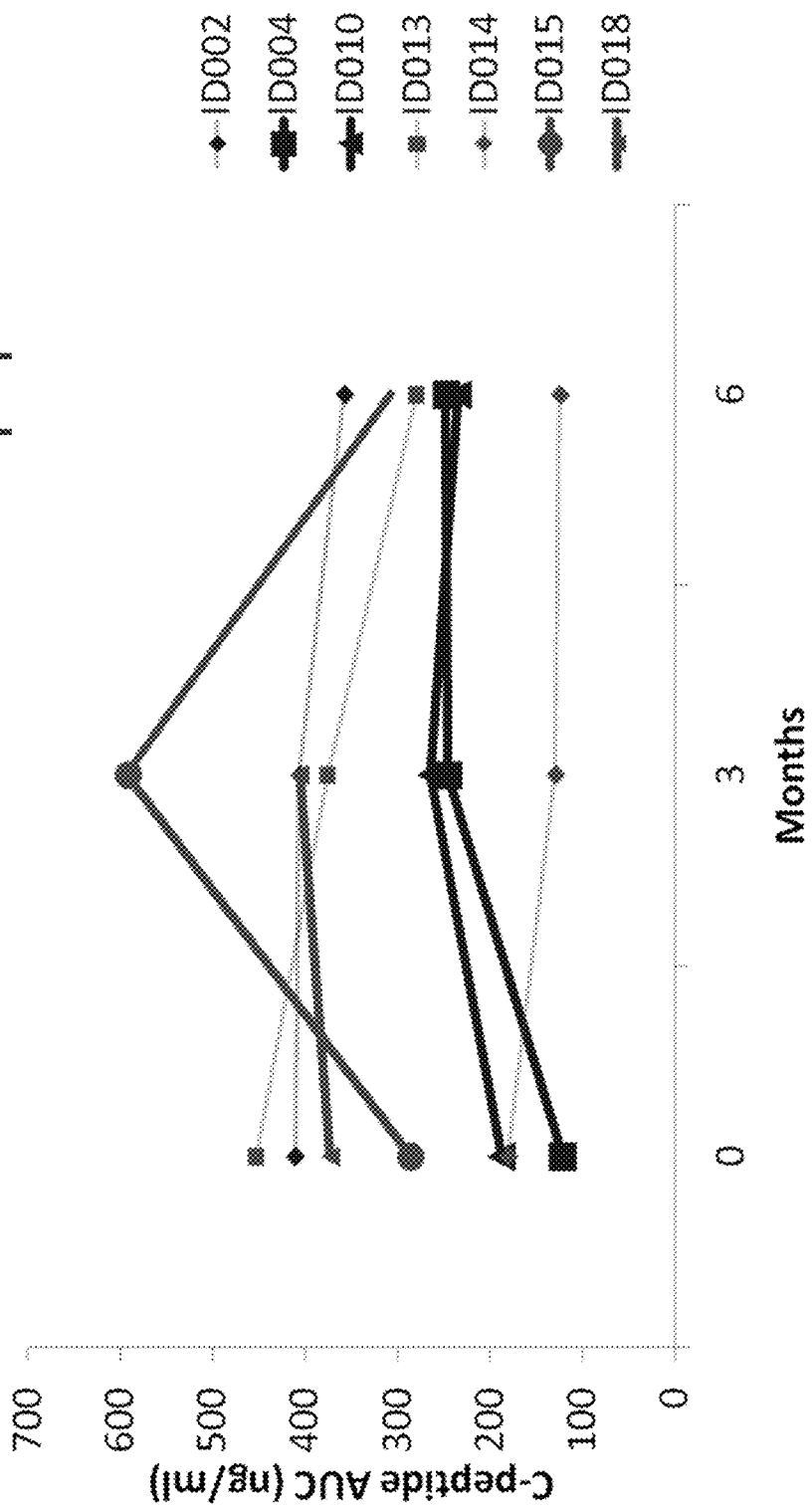
FIG. 13 represents a graph of C-peptide levels over time in T1D subjects.

FIG. 13 represents a graph of C-peptide levels over time in T1D subjects where the majority of subjects show an increase in C-peptide.

Figures 14A, 14B:
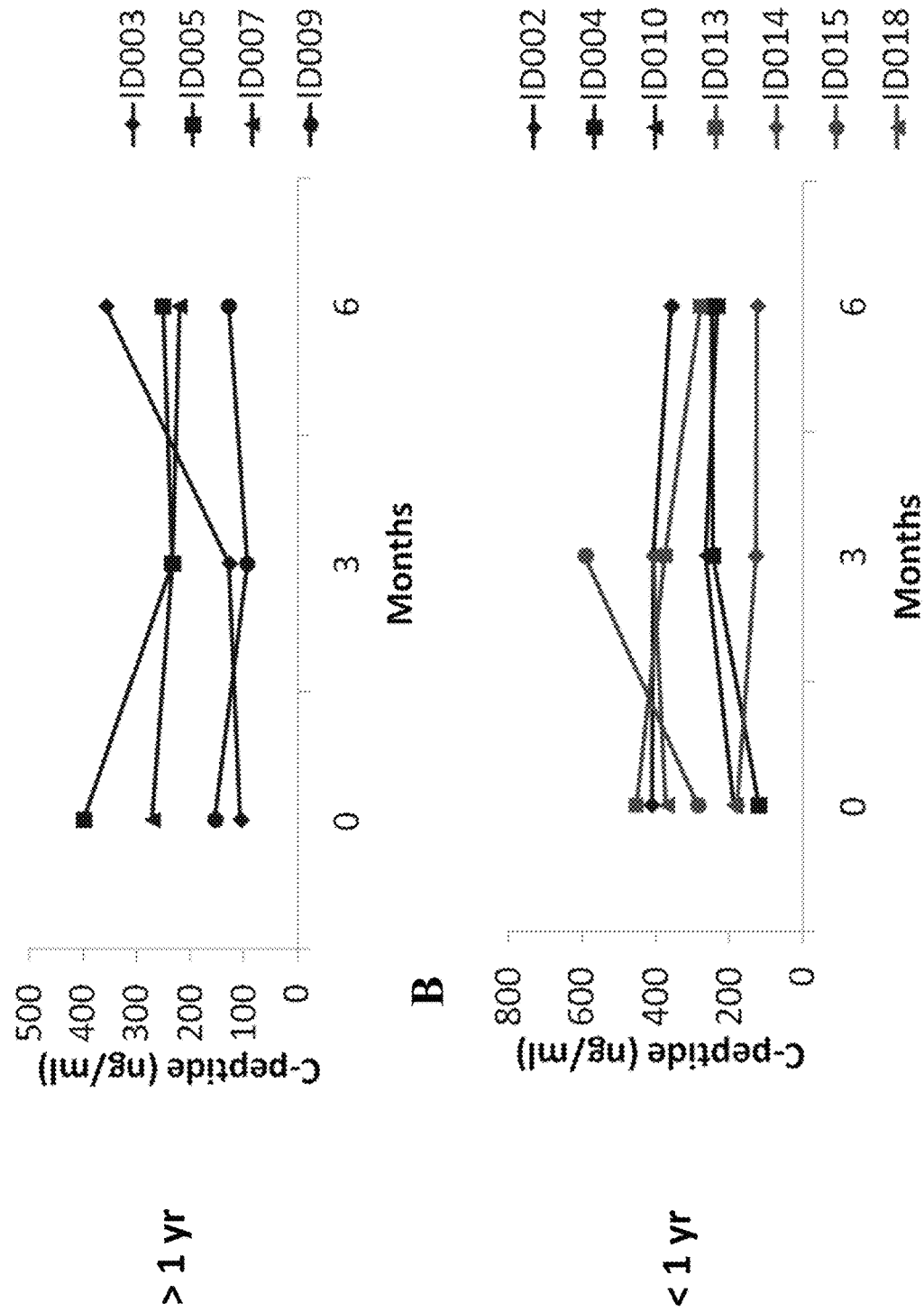
FIGS. 14A-14B represent graphs of C-peptide levels over time in T1D subjects.

FIGS. 14A-14B represent graphs of C-peptide levels over time in T1D subjects.

Figures 15A, 15B:
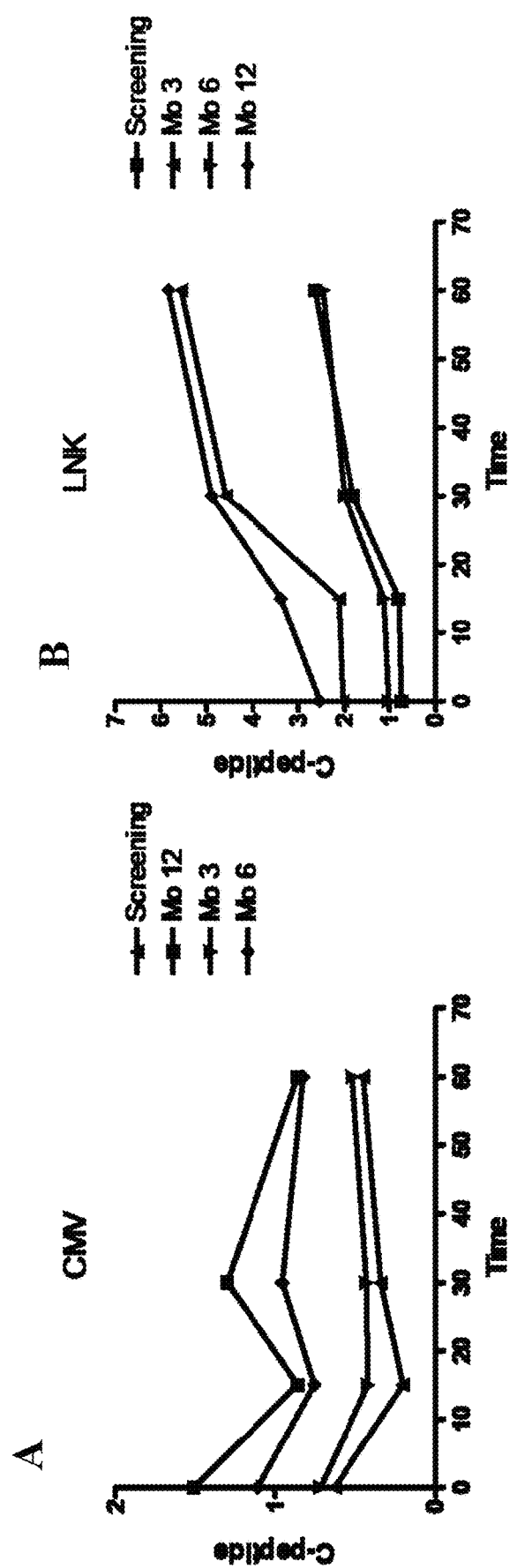
FIGS. 15A-15B represent graphs of C-peptide levels over time in T1D subjects after AAT treatment.

FIGS. 15A-15B represent graphs of C-peptide levels over time in T1D subjects after AAT treatment.

Figure 16:
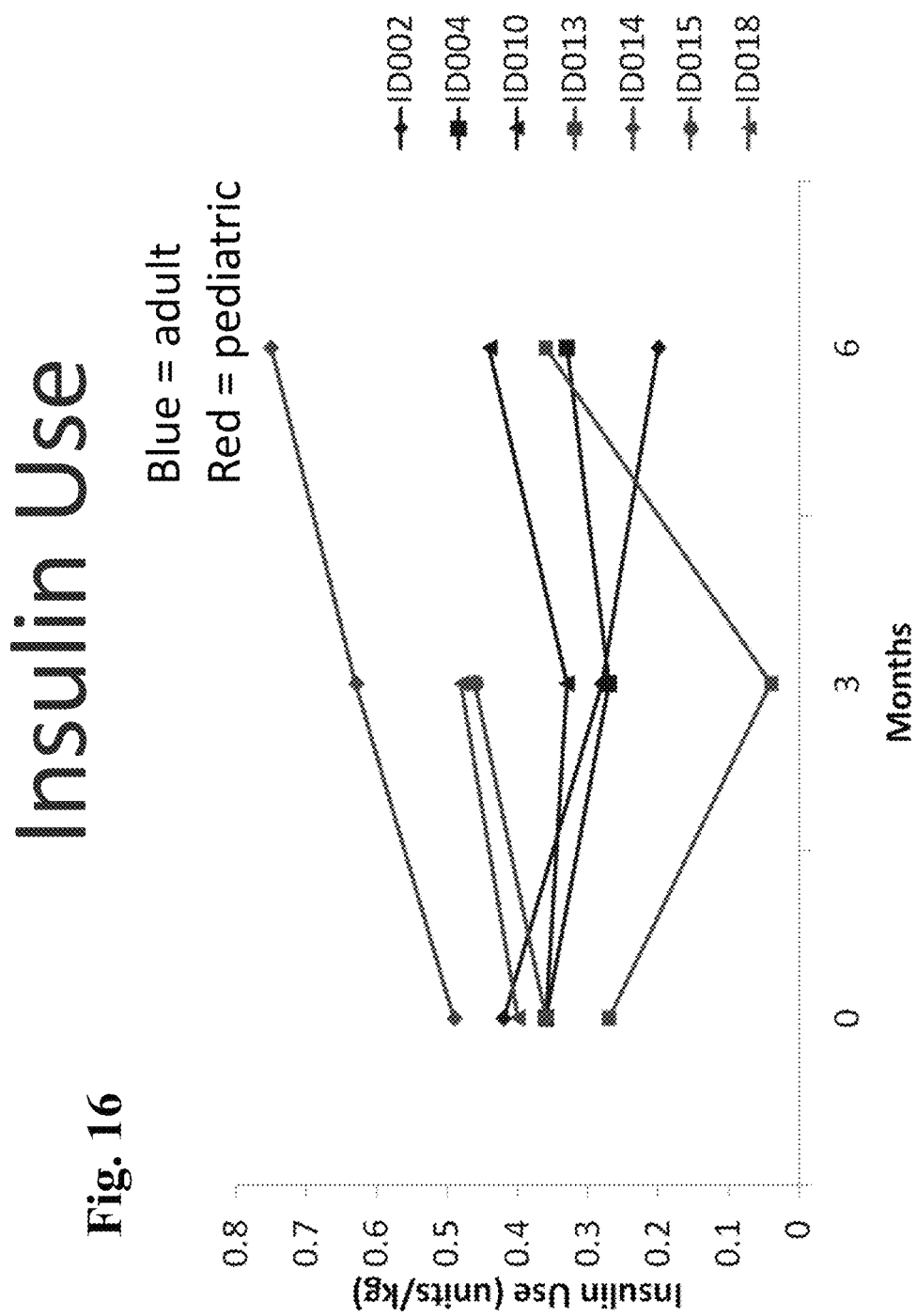
FIG. 16 represents a graph of insulin use over time in various T1D subjects monitored, adult and pediatric T1 D subjects.

FIG. 16 represents a graph of insulin use over time in various T1D subjects monitored, adult and pediatric T1D subjects.

Figure 17:
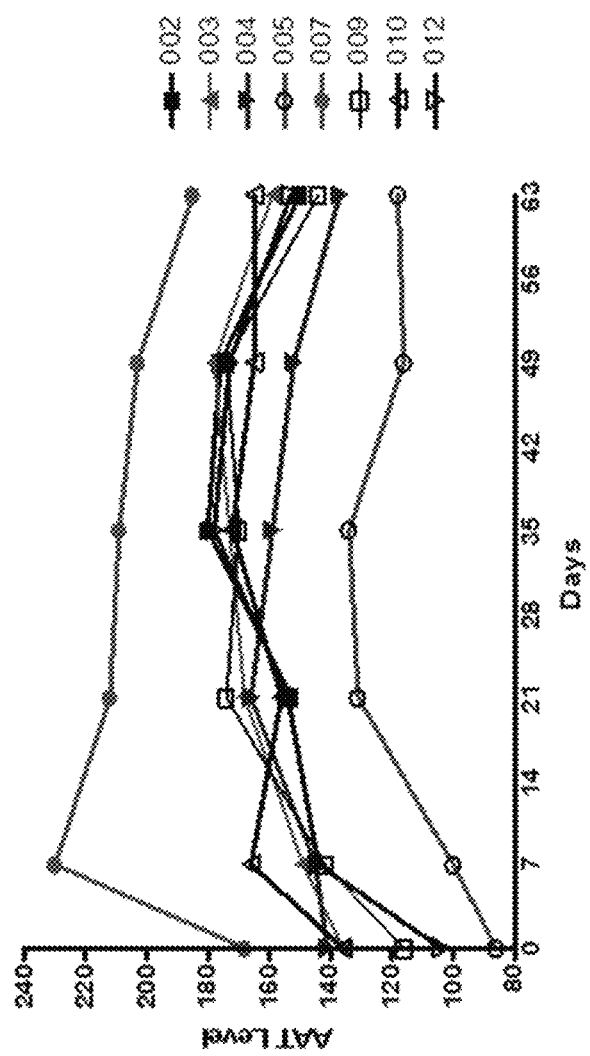
FIG. 17 represents a graph of AAT levels over time in various subjects monitored, adult and pediatric T1 D subjects.

FIG. 17 represents a graph of AAT levels over time in various subjects monitored, adult and pediatric T1D subjects.

Figure 18:
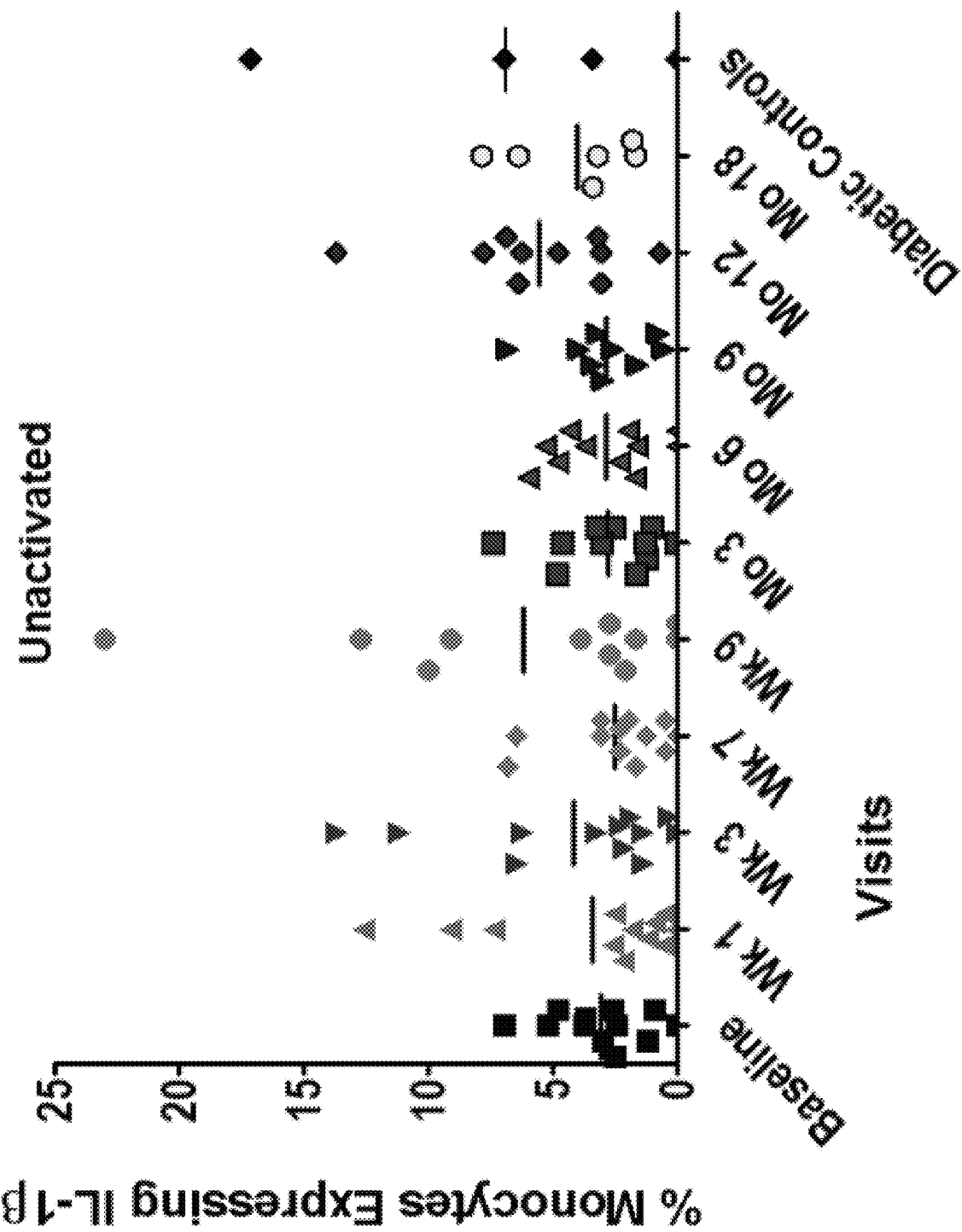
FIG. 18 represents a graph of percentage of monocytes in a subject expressing IL-1β in unactivated cells.

FIG. 18 represents a graph of percentage of monocytes in a subject expressing IL-1β in unactivated cells.

Figure 19:
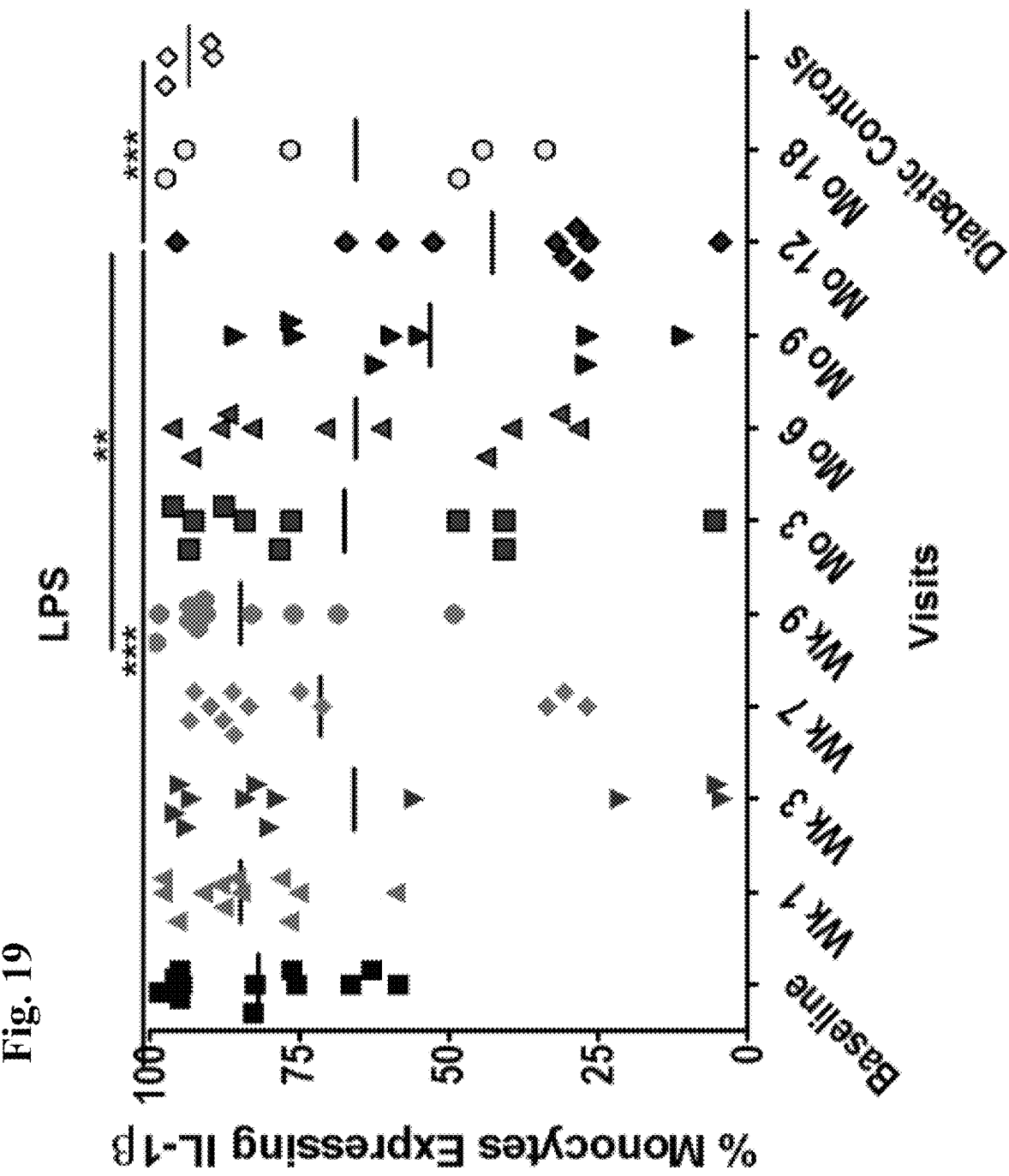
FIG. 19 represents a graph of percentage of monocytes in a subject expressing IL-1β in LPS-activated cells.

FIG. 19 represents a graph of percentage of monocytes in a subject expressing IL-1β in LPS-activated cells.

Figure 20:
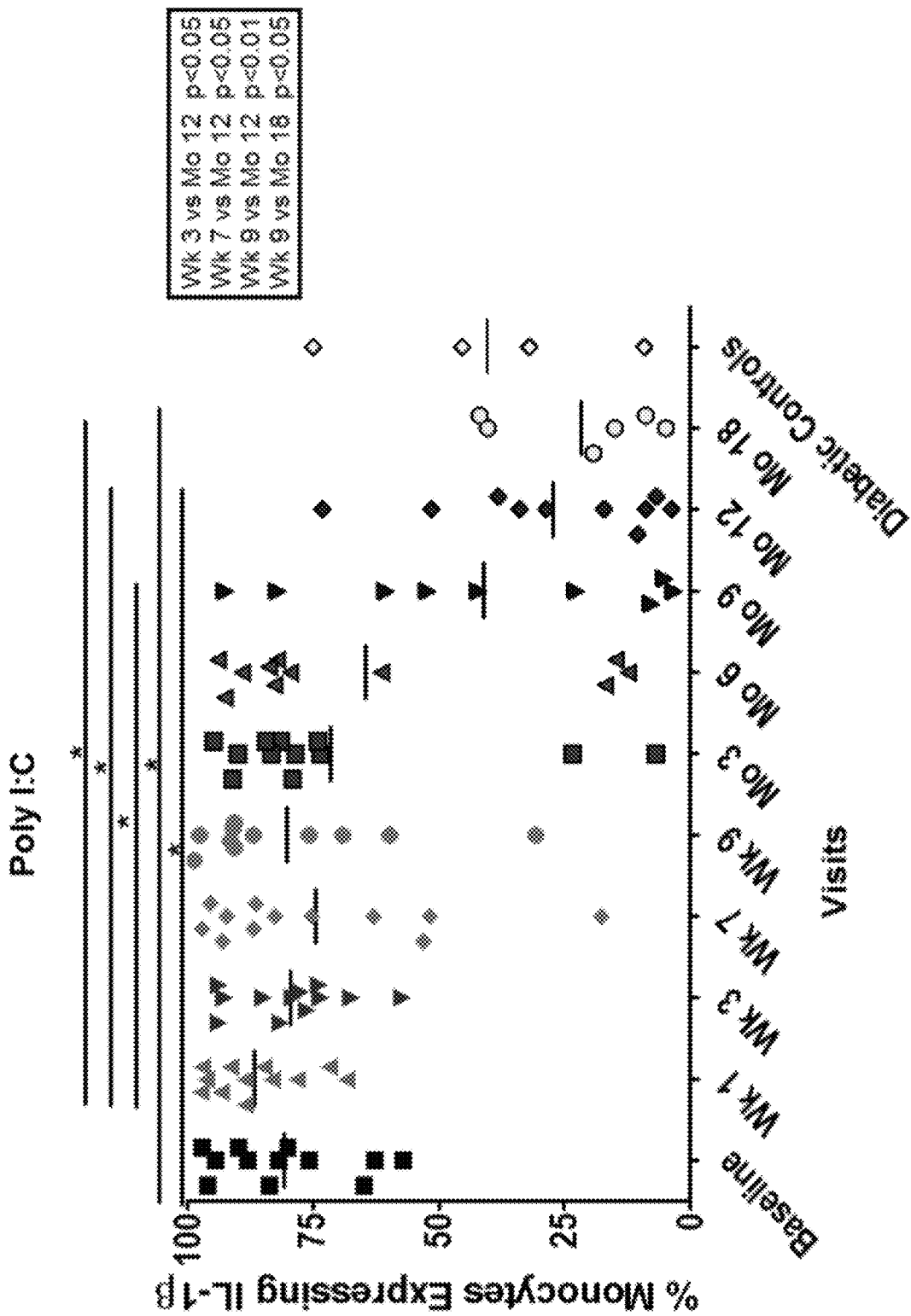
FIG. 20 represents a graph of percentage of monocytes in a subject expressing IL-1β in Poly I:C-activated cells.

FIG. 20 represents a graph of percentage of monocytes in a subject expressing IL-1β in Poly I:C-activated cells where the subject have been treated with AAT and levels are measured shortly after treatment and up to 18 months later. This graph illustrates that monocytes expressing IL-1β are reduced in treated subjects several months to greater than 18 months after treatment.

Figure 21:
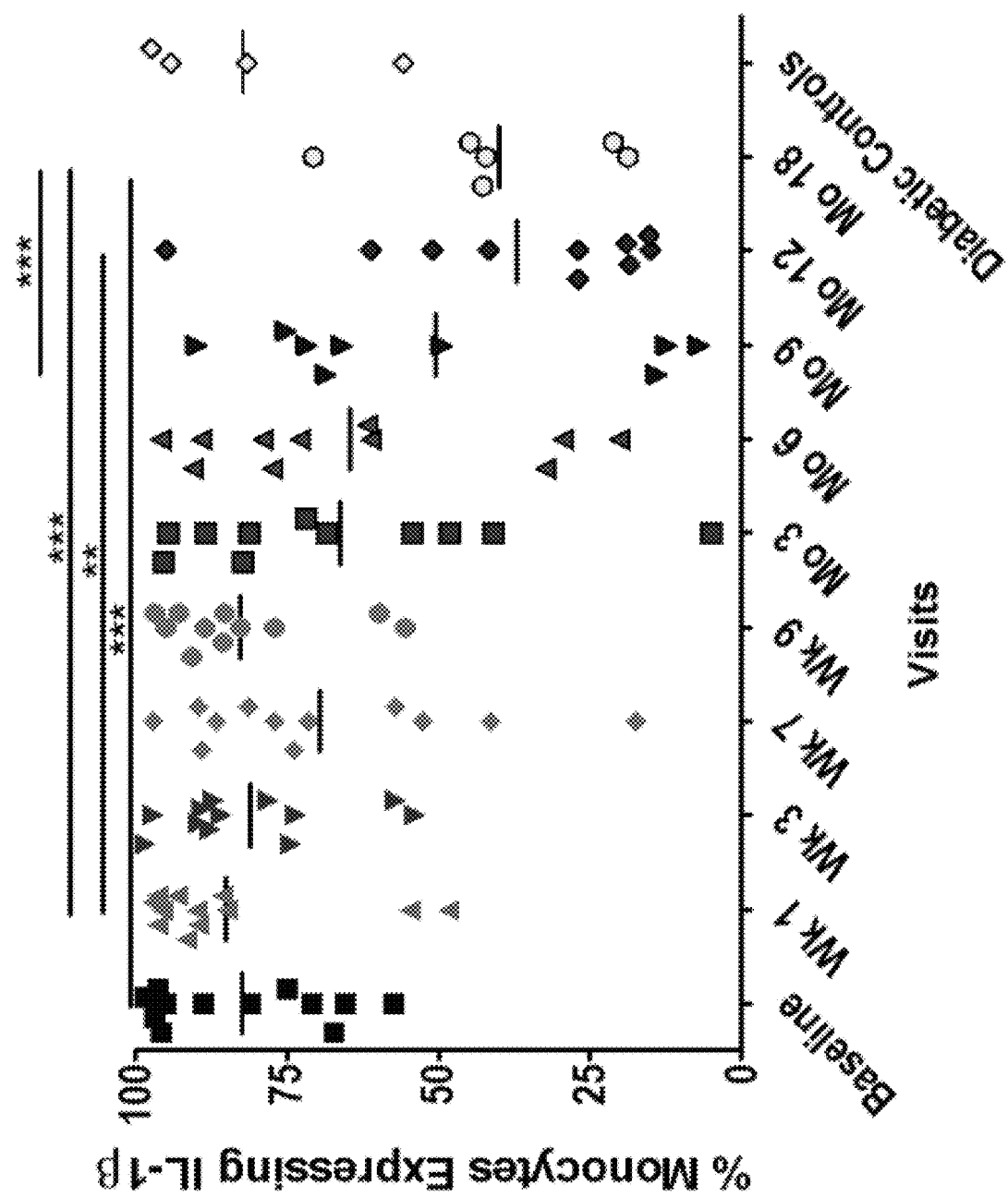
FIG. 21 represents a graph of percentage of monocytes in a subject expressing IL-1β in R848-activated cells.

FIG. 21 represents a graph of percentage of monocytes in a subject expressing IL-1β in R848-activated cells where the subject have been treated with AAT and levels are measured shortly after treatment and up to 18 months later. This graph illustrates that monocytes expressing IL-1β are reduced in AAT-treated subjects several months to greater than 18 months after treatment.

Figure 22:
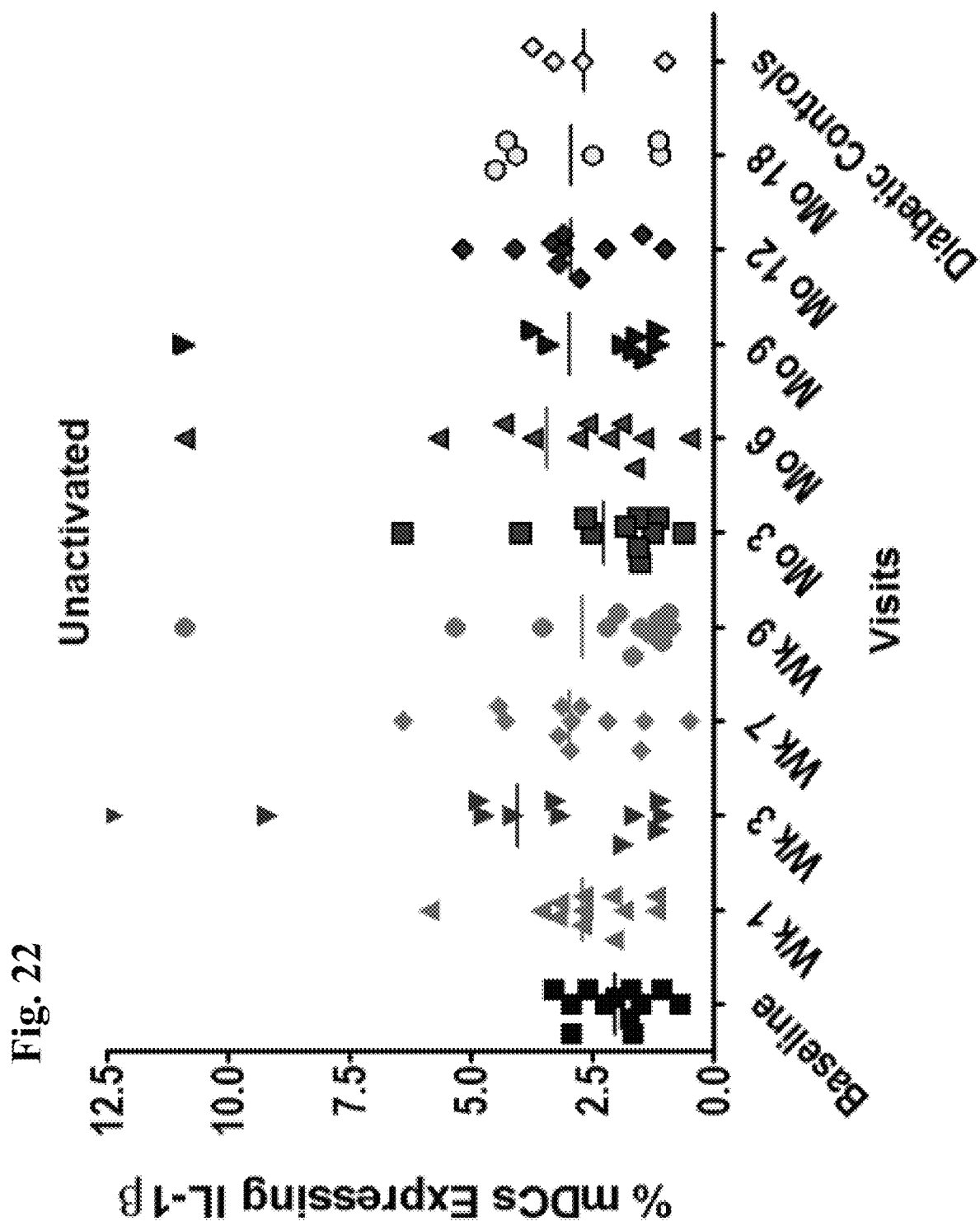
FIG. 22 represents a graph of percentage of DC (dendridic cells) in a subject expressing IL-1β in unactivated cells.

FIG. 22 represents a graph of percentage of DC (dendridic cells) in a subject expressing IL-1β in unactivated cells. This graph illustrates that dendridic cells expressing IL-1β are reduced in treated subjects several months to greater than 18 months after treatment.

Figure 23:
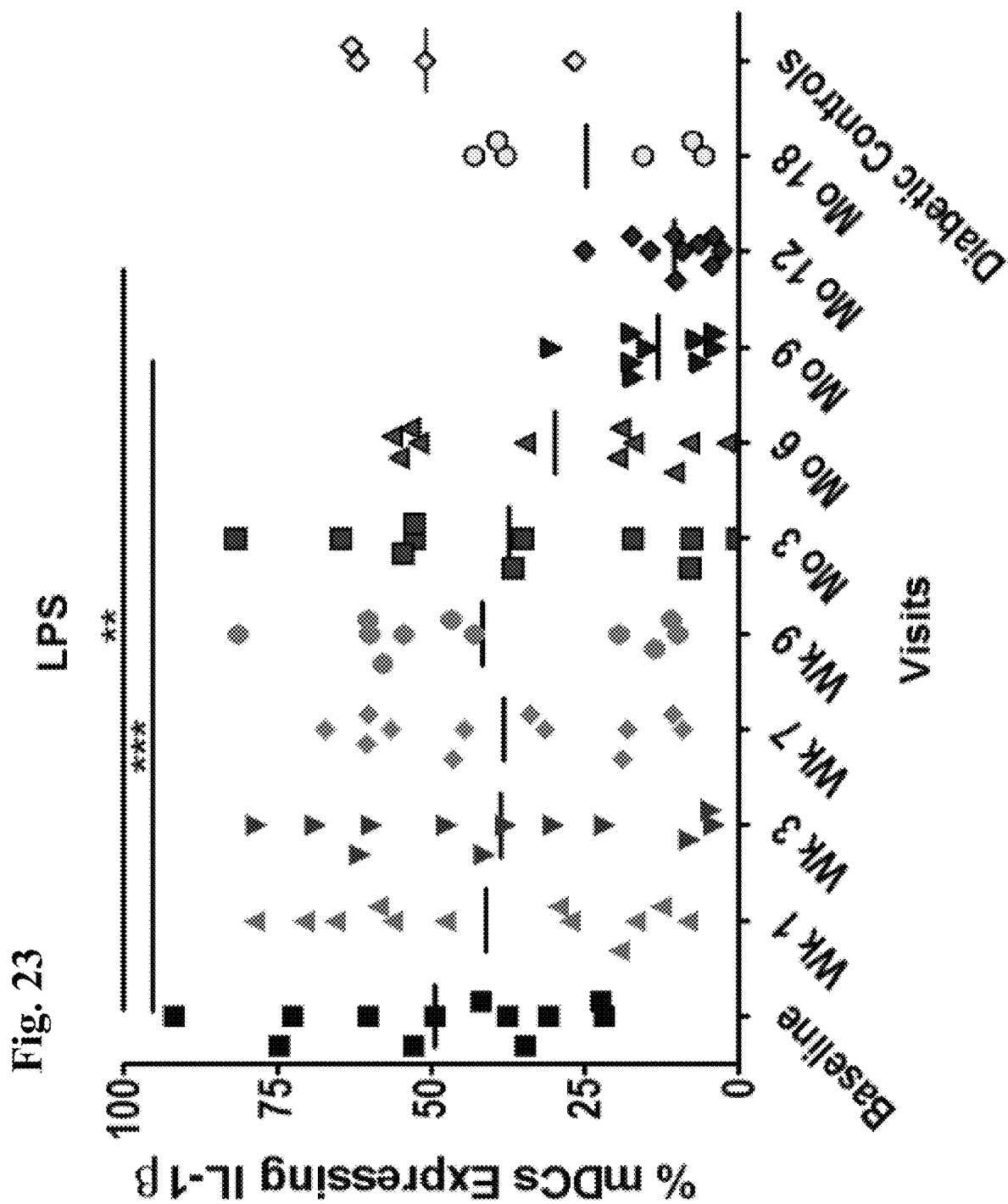
FIG. 23 represents a graph of percentage of DC (dendridic cells) in a subject expressing IL-1β in LPS-activated cells.

FIG. 23 represents a graph of percentage of DC (dendridic cells) in a subject expressing IL-1β in LPS-activated cells. This graph illustrates that dendridic cells stimulated with LPS have reduced IL-1β expression in AAT-treated subjects several months to greater than 18 months after treatment.

Figure 24:
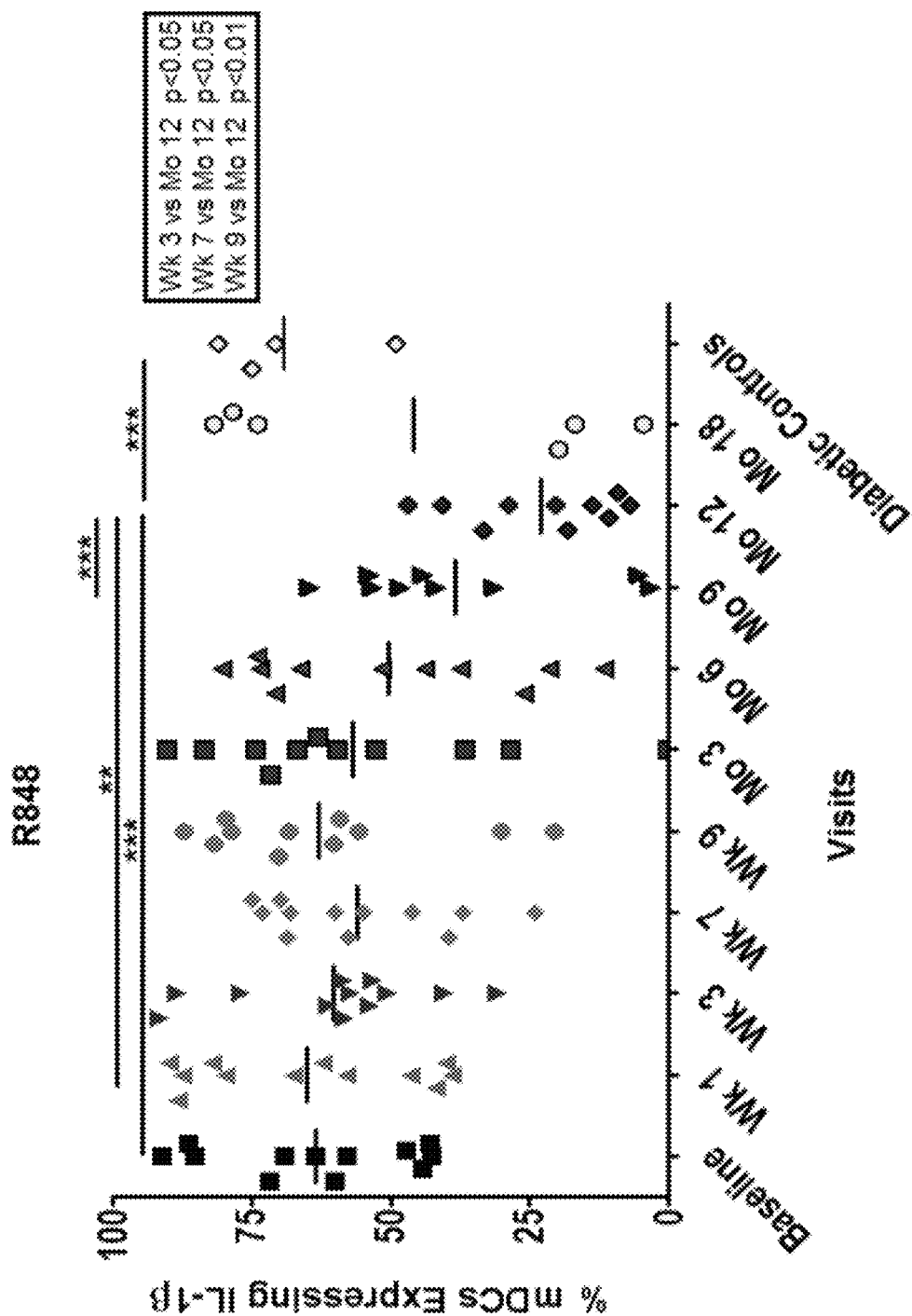
FIG. 24 represents a graph of percentage of DC (dendridic cells) in a subject expressing IL-1β in R848-activated cells.

FIG. 24 represents a graph of percentage of DC (dendridic cells) in a subject expressing IL-1β in R848-activated cells. This graph illustrates that dendridic cells stimulated with R848 have reduced IL-1β expression in AAT-treated subjects several months to greater than 18 months after treatment.

Figure 25:
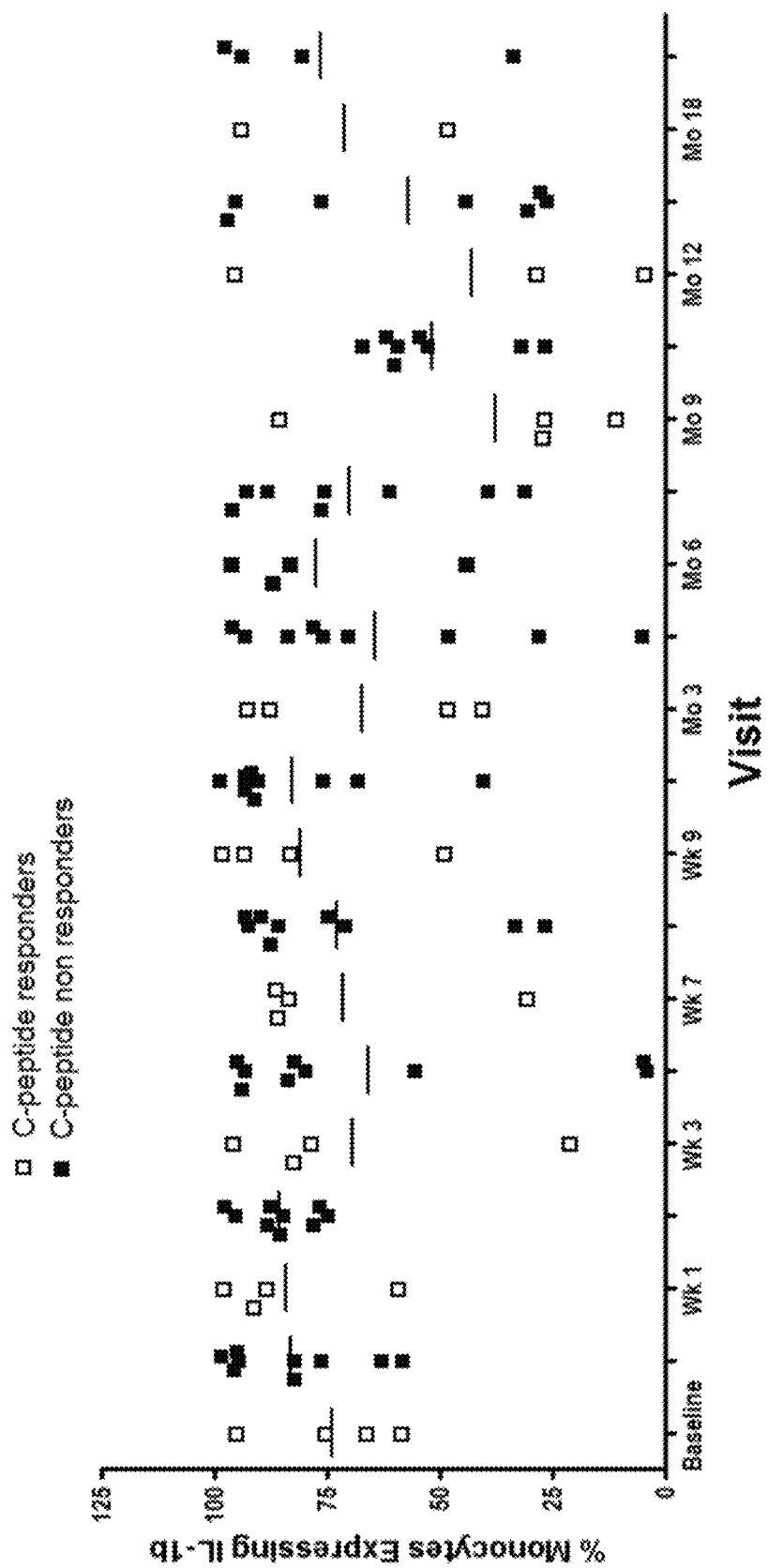
FIG. 25 represents a plot of percent of monocytes expressing IL-1β corrrelated with C-peptide levels.

FIG. 25 represents a plot of percent of monocytes expressing IL-1β corrrelated with C-peptide levels. This graph is a comparison for correlation of C-peptide response with IL-1β expression in monocytes.

Figure 26:
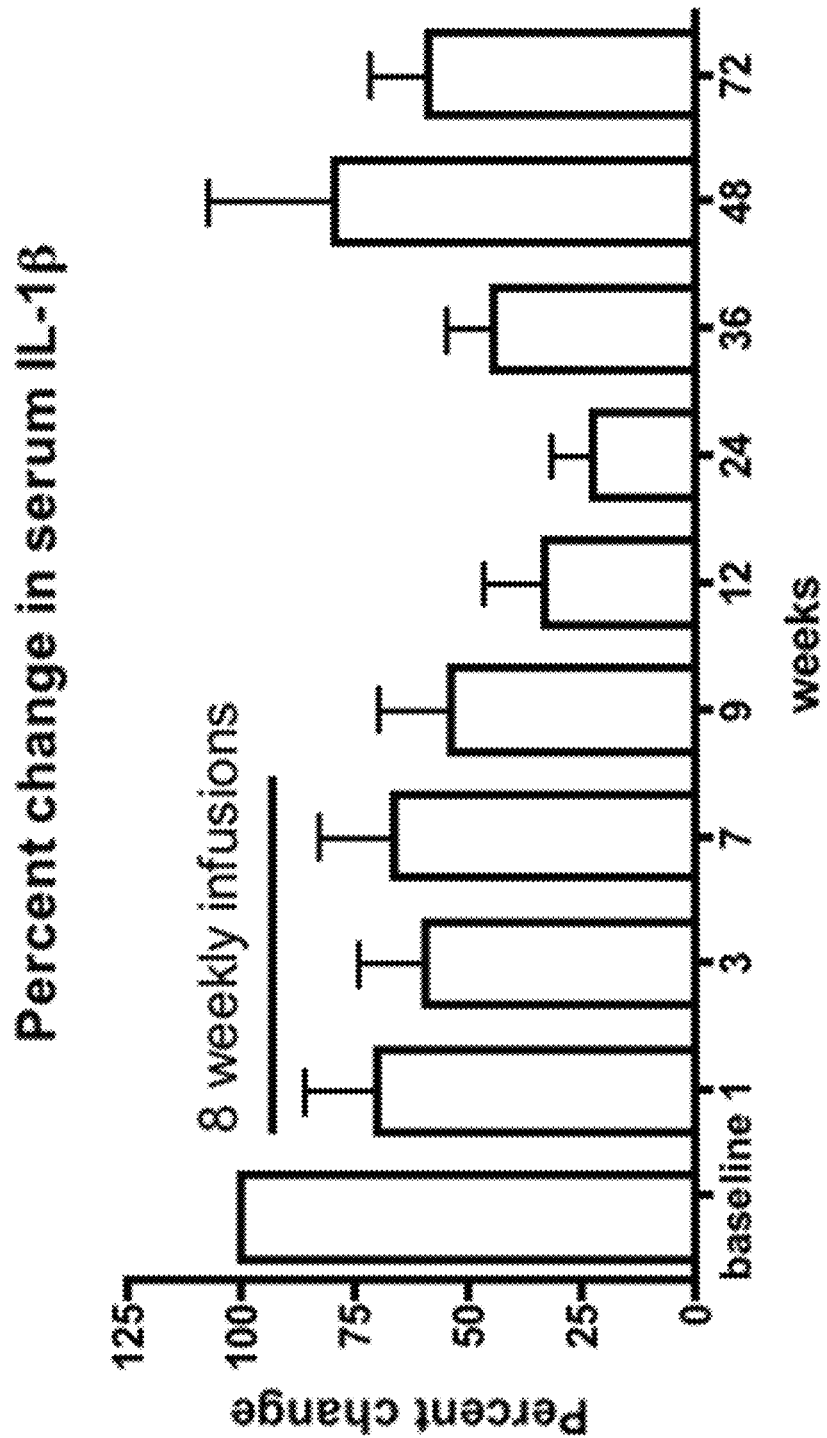
FIG. 26 represents a histogram plot of percent change in serum IL-1β in subjects over time.

FIG. 26 represents a histogram plot of percent change in serum IL-1β in subjects over time before and after AAT-administration to a subject. Therefore, a short treatment of AAT (e.g. 8 weeks) resulted in reduced levels of IL-1β in the subjects, weeks to months after administration.

Figure 27:
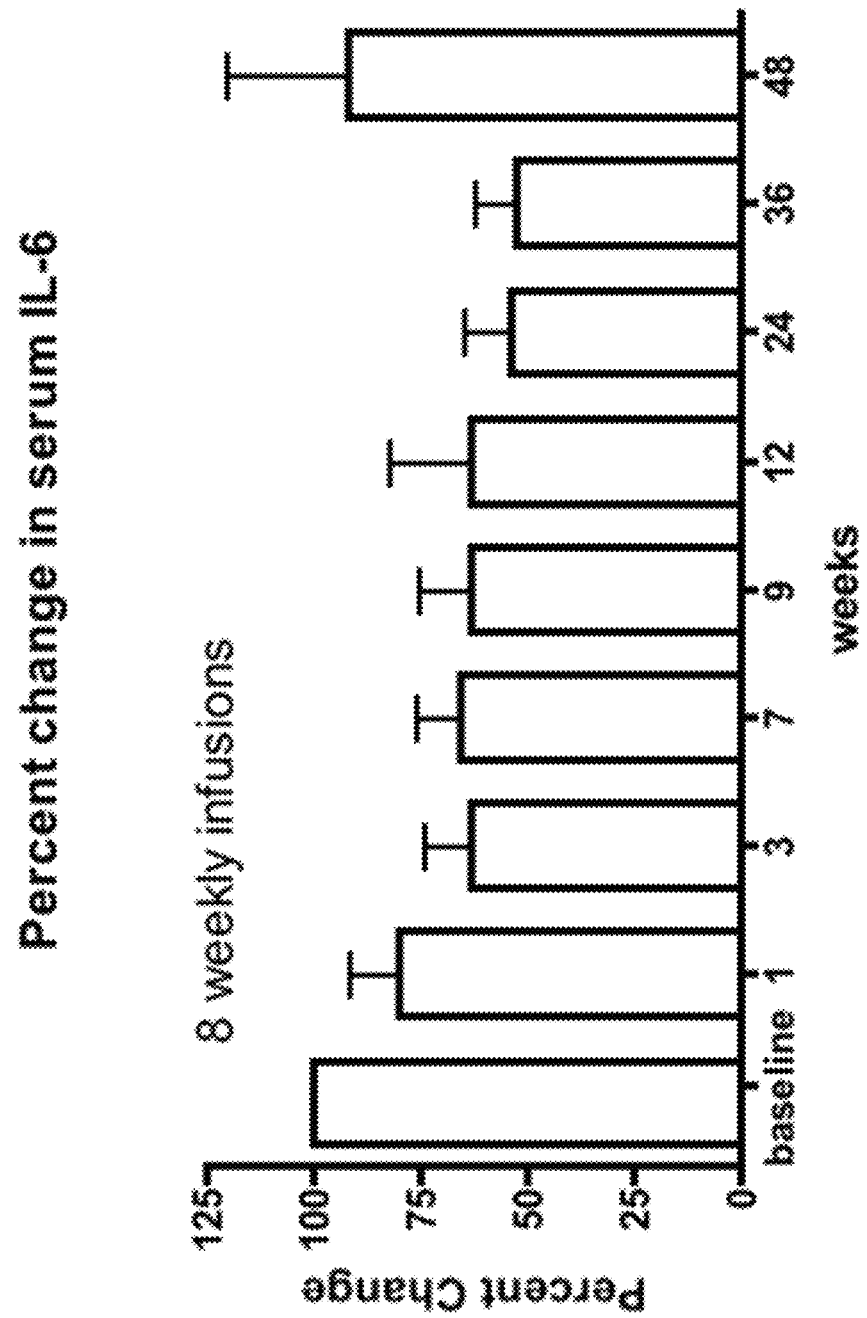
FIG. 27 represents a histogram plot of percent change in serum IL-6 in subjects over time.

FIG. 27 represents a histogram plot of percent change in serum IL-6 in subjects over time before and after AAT-administration to a subject. Therefore, a short treatment of AAT (e.g. 8 weeks) resulted in reduced levels of IL-6 in the subjects, weeks to months after administration.

Figure 28:
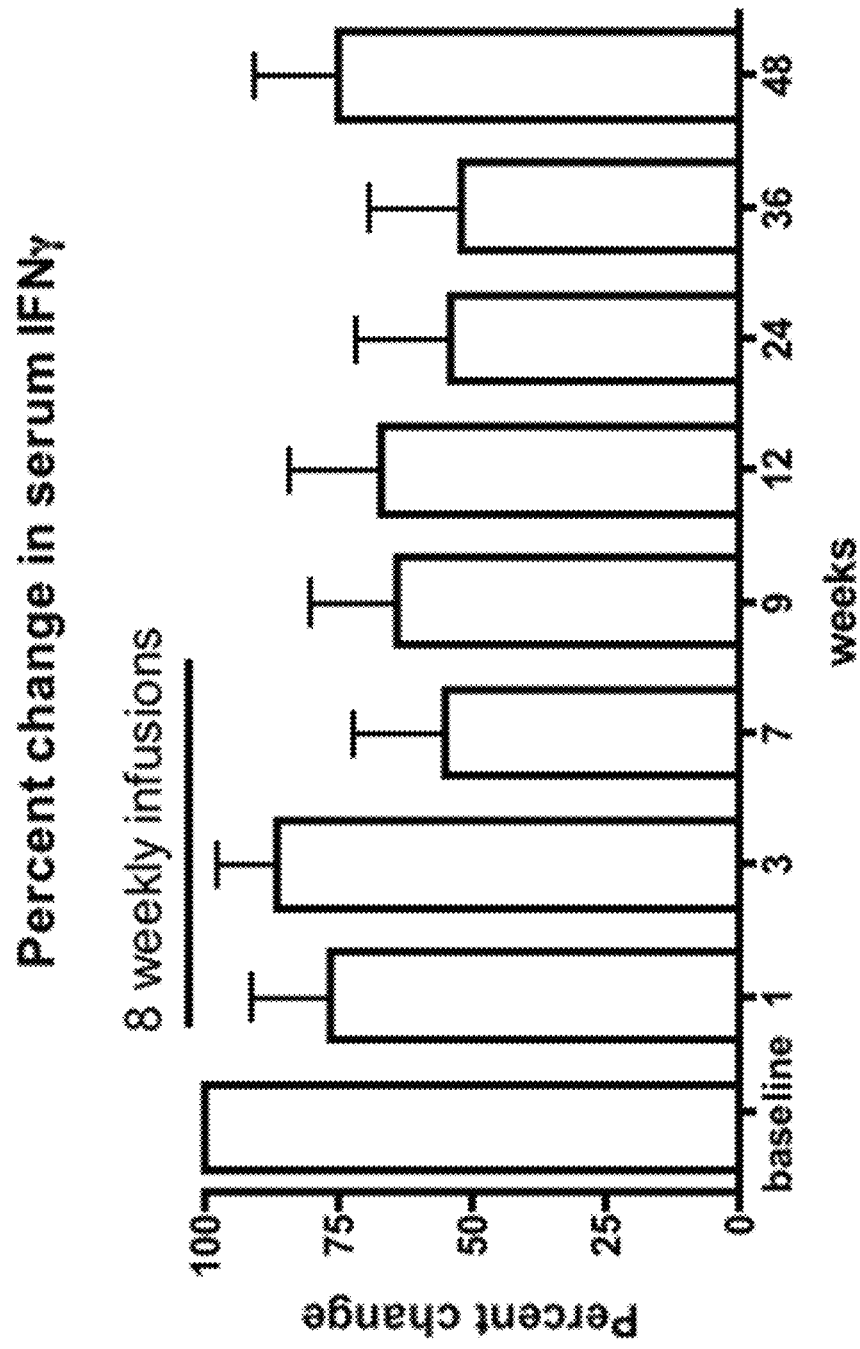
FIG. 28 represents a histogram plot of percent change in serum IFN-γ in subjects over time.

FIG. 28 represents a histogram plot of percent change in serum IFN-γ in subjects over time before and after AAT-administration to a subject. Therefore, a short weekly regimen of AAT (e.g. 8 weeks) resulted in reduced levels of IFN-γ in the subjects, weeks to months after administration.

Figure 29:
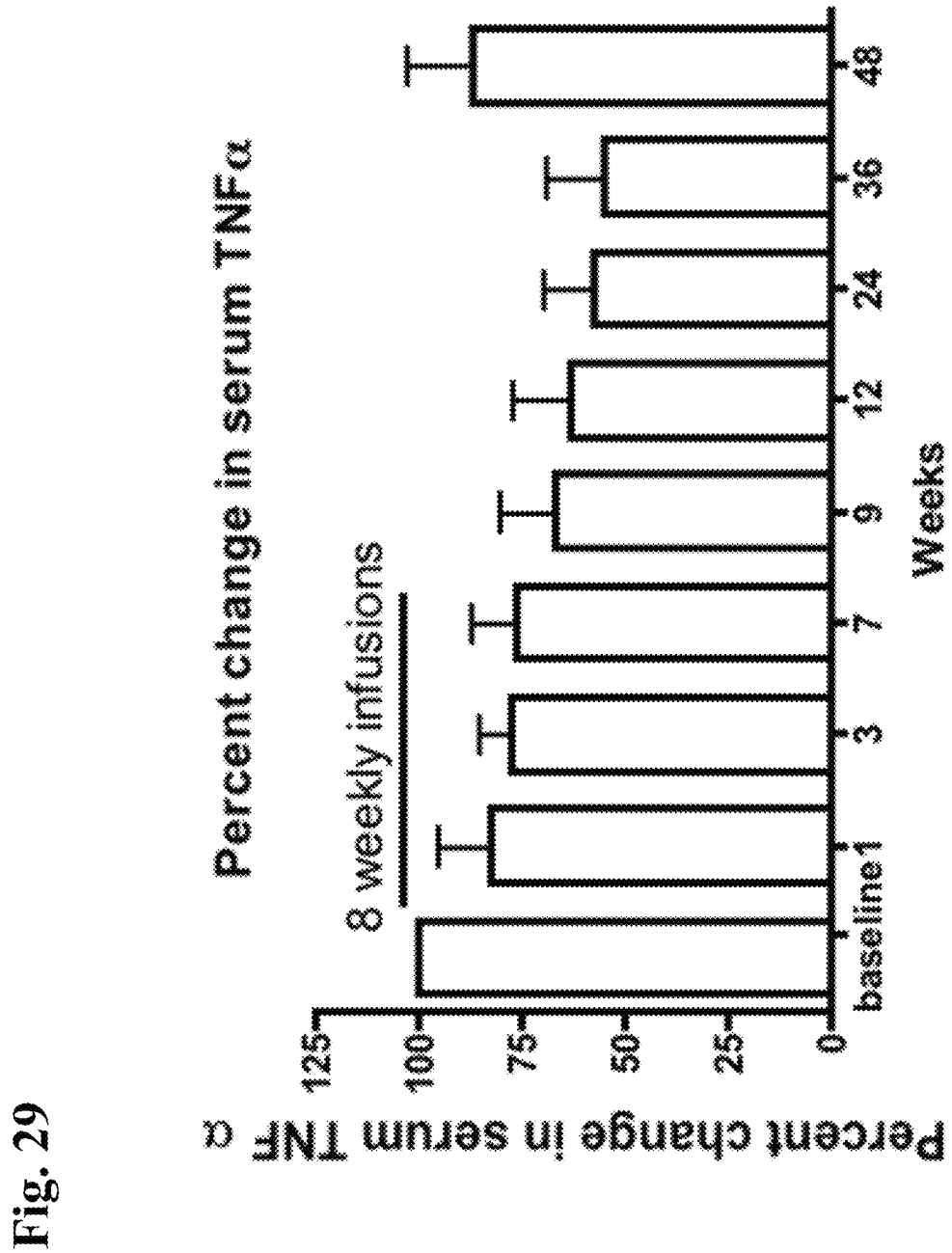
FIG. 29 represents a histogram plot of percent change in serum TNF-α in subjects over time.

FIG. 29 represents a histogram plot of percent change in serum TNF-α in subjects over time before and after AAT-administration to a subject. Therefore, a short weekly regimen of AAT (e.g. 8 weeks) resulted in reduced levels of TNF-α in the subjects, weeks to months after administration.

Figure 30:
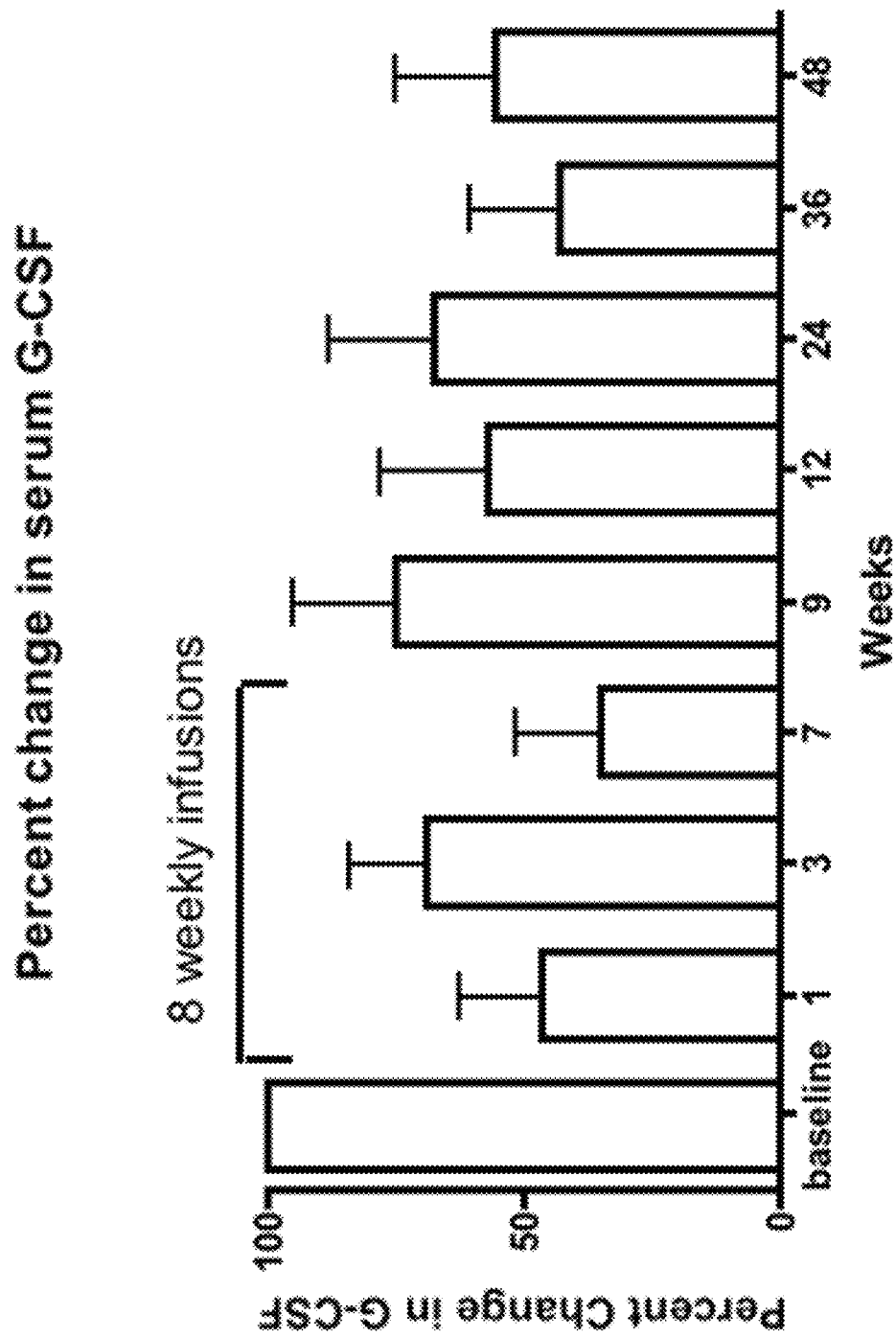
FIG. 30 represents a histogram plot of percent change in serum G-CSF in subjects over time.

FIG. 30 represents a histogram plot of percent change in serum G-CSF in subjects over time.

Figure 31:
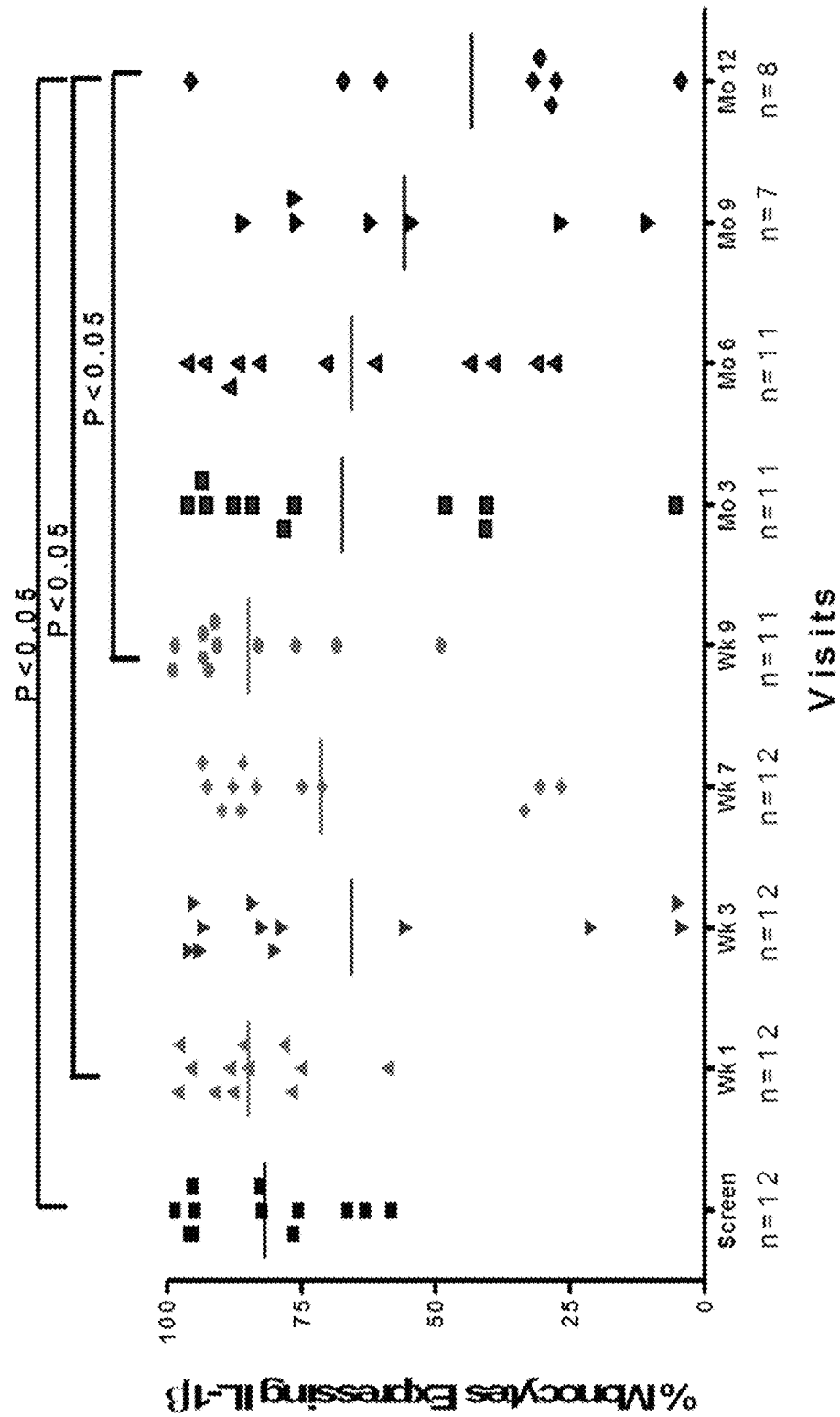
FIG. 31 represents a plot of percent change in monocyte LPS-induced IL-1β in subjects over time.
Figure 32:
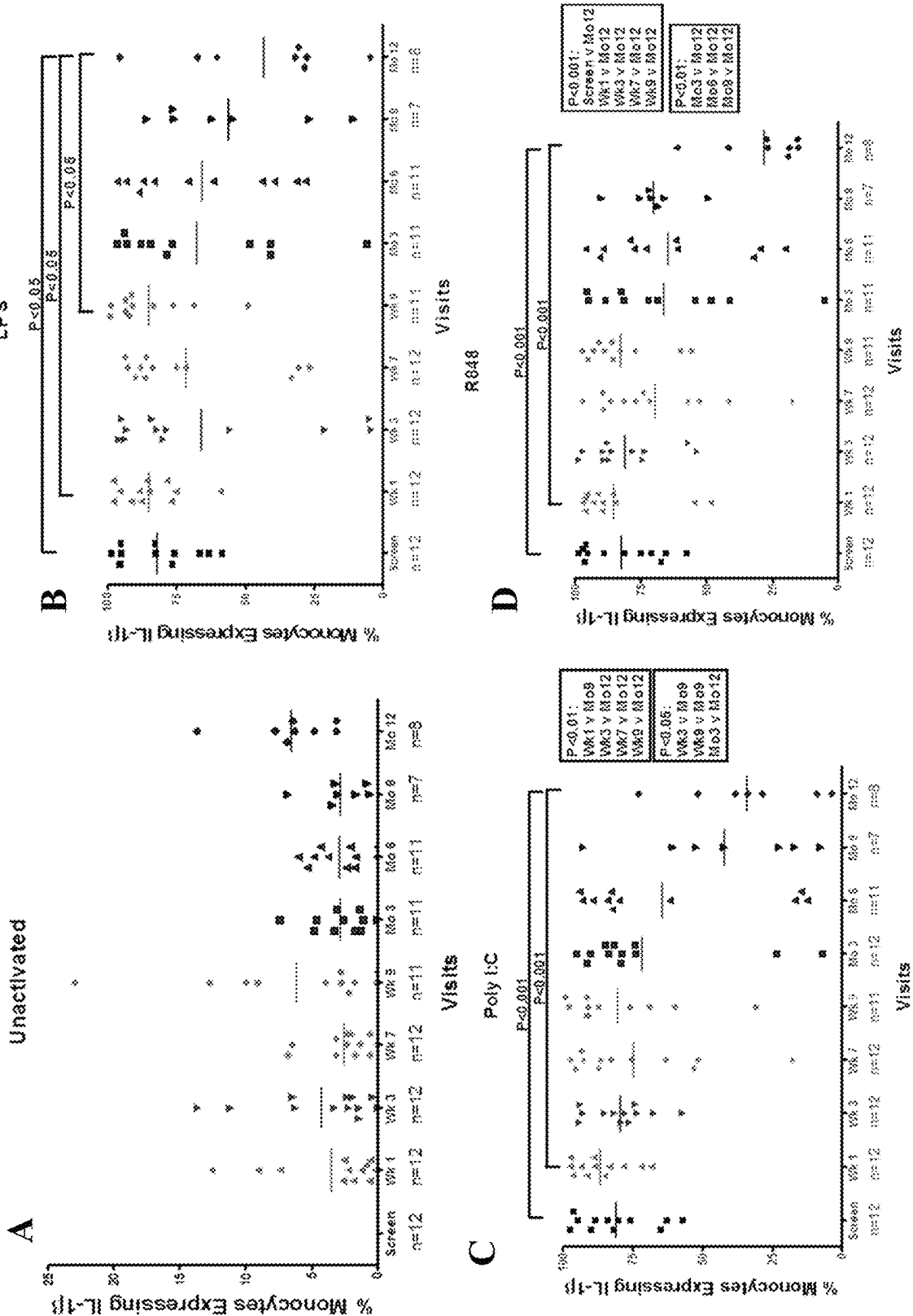
FIGS. 32A-32D illustrate percent of monocyte expressing IL-1β in T1D and control subjects over time.

FIG. 31 represents a plot of percent change in monocyte LPS-induced IL-1β in subjects over time.

FIGS. 32A-32D illustrate percent of monocyte expressing IL-1β in T1D and control subjects over time. These plots illustrate that AAT-treatment reduced IL-1β expression in stimulated monocyte populations long after the treatments were administered.

Figure 33:
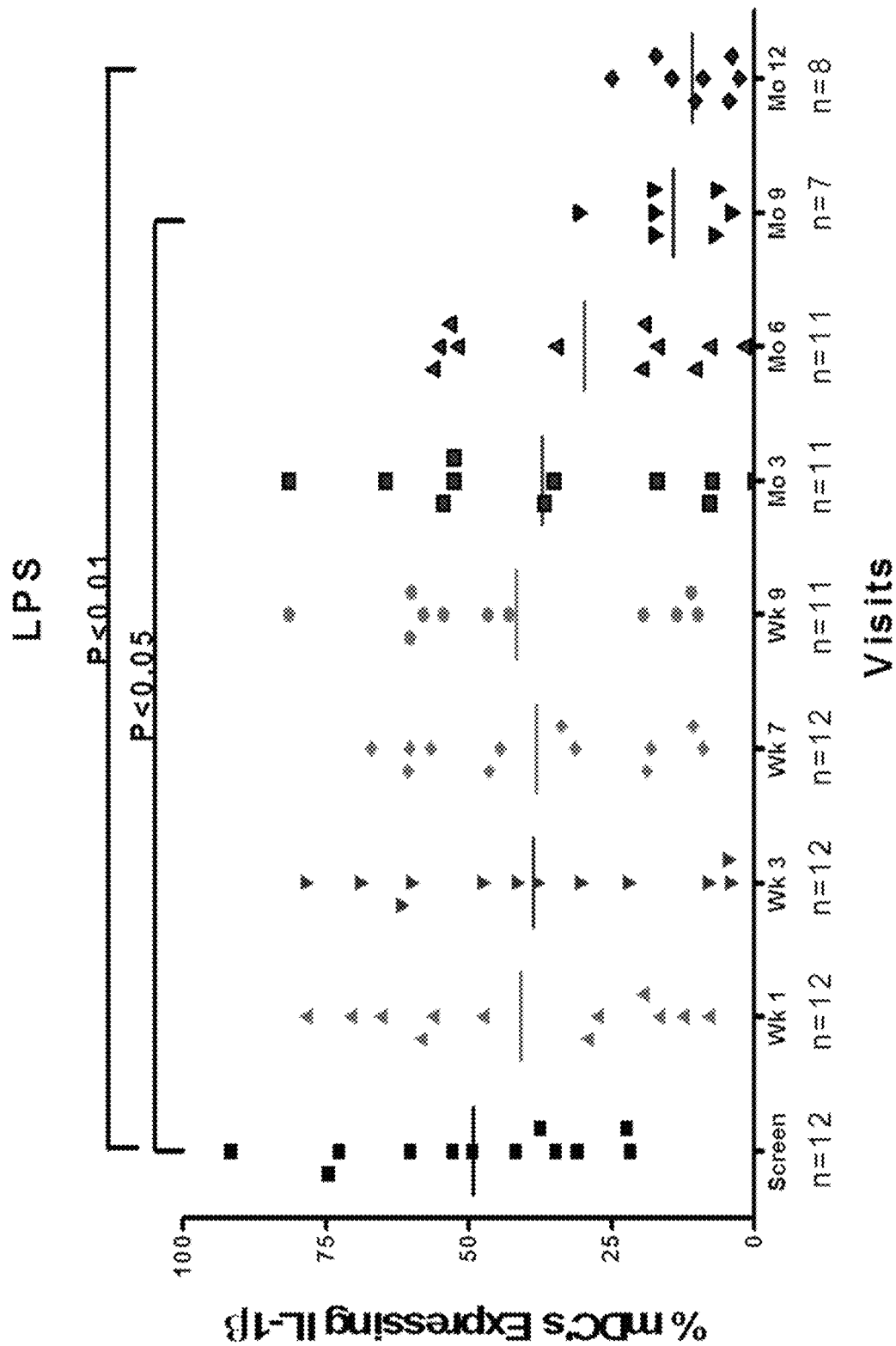
FIG. 33 represents a plot of percent change in DC cells expressing IL-1β in subjects over time.
Figures 34A, 34B, 34C, 34D:
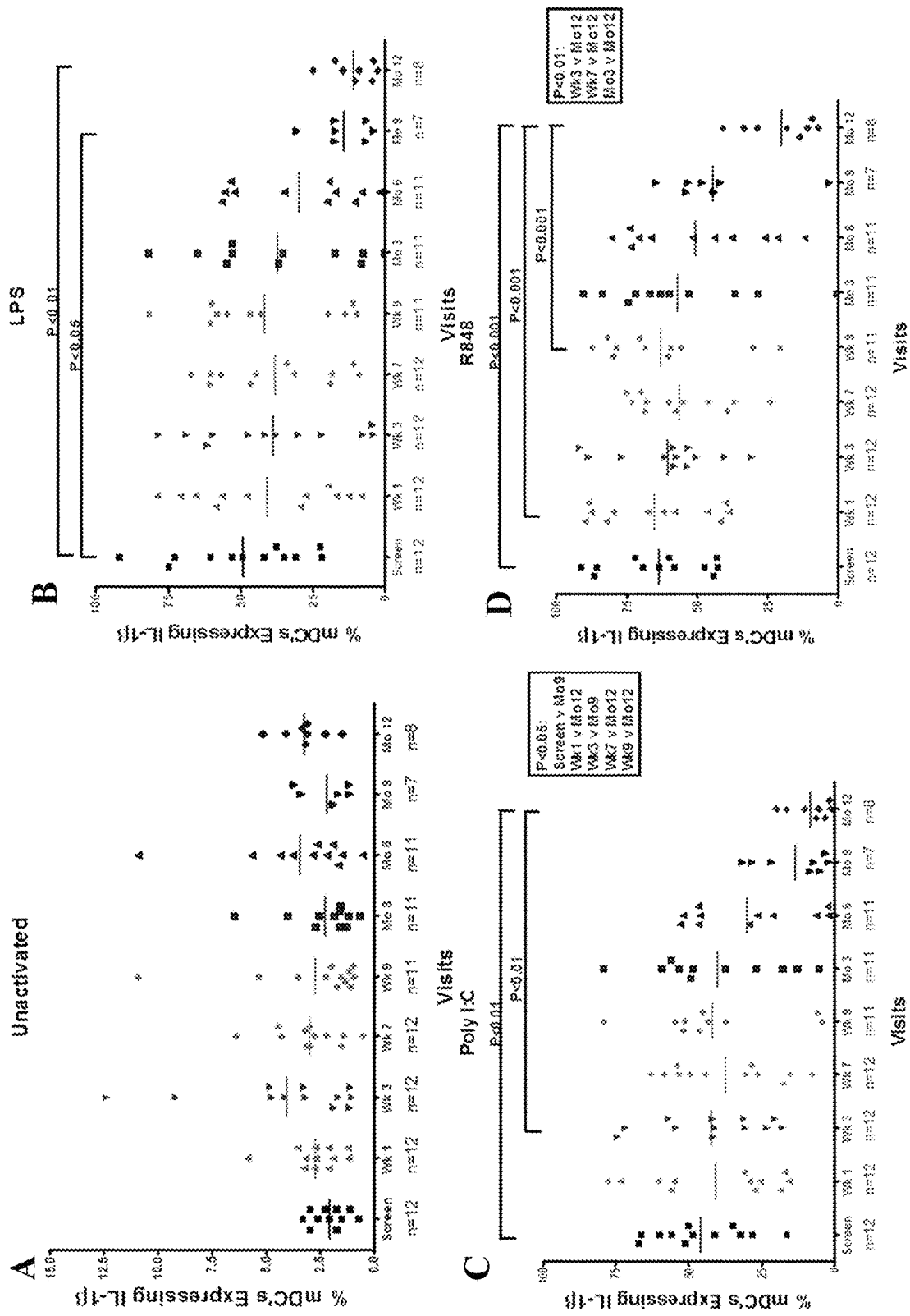
FIGS. 34A-34D illustrates percent of mDC's expressing IL-1β in T1D and control subjects over time.

FIG. 33 represents a plot of percent change in DC cells expressing IL-1β in subjects over time. This plot illustrates that AAT-treatment reduced IL-6 expression in monocytes under various stimulus conditions long after the treatments were administered.

FIGS. 34A-34D illustrates percent of mDC's expressing IL-1β in T1D and control subjects over time. These plots illustrate that AAT-treatment reduced IL-1β expression in stimulated DC populations long after the treatments were administered.

Figure 35:
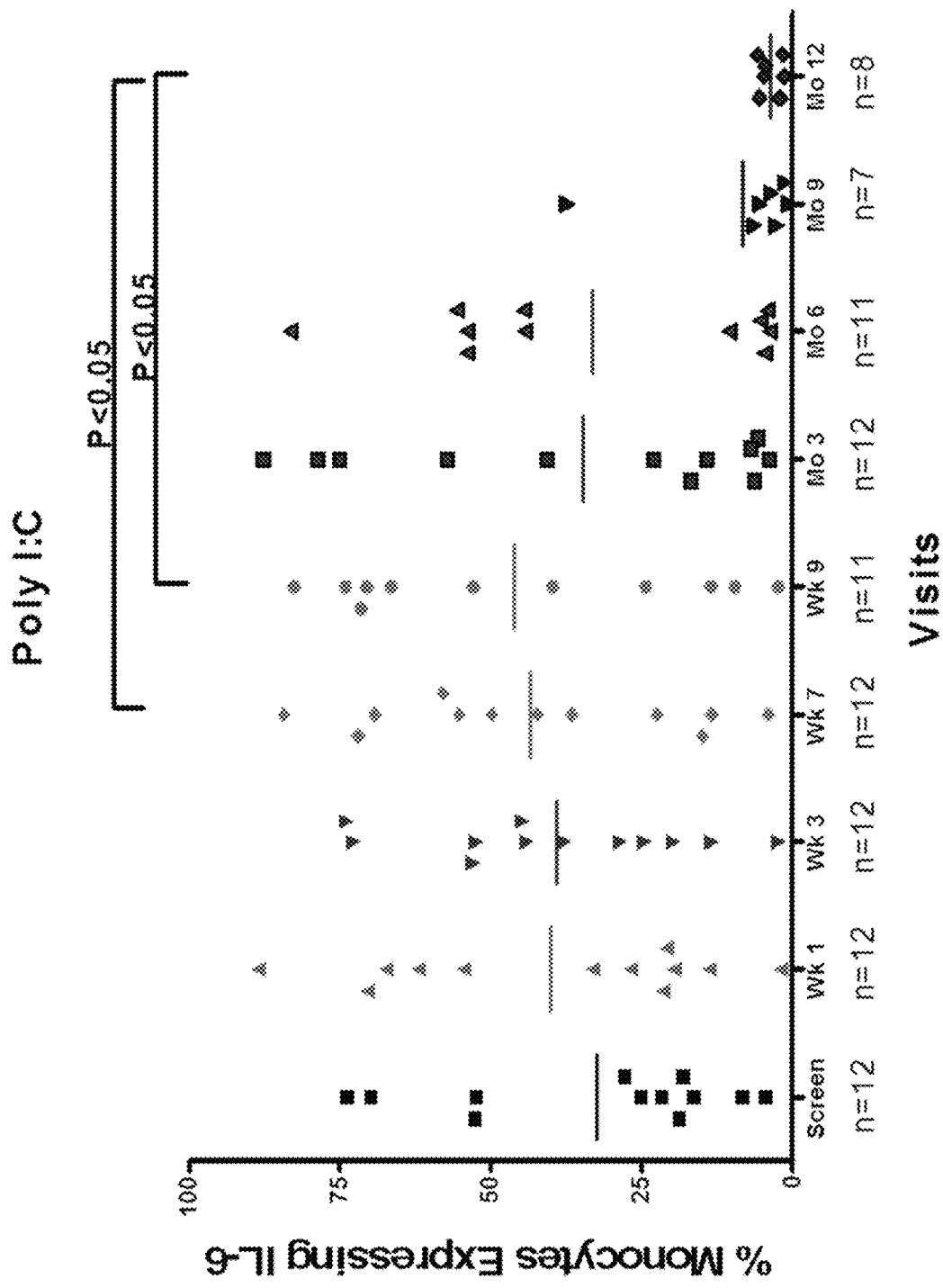
FIG. 35 represents a plot of percent change in Poly-IC induced monocyte cell IL-6 expression in subjects over time.
Figures 36A, 36B, 36C, 36D:
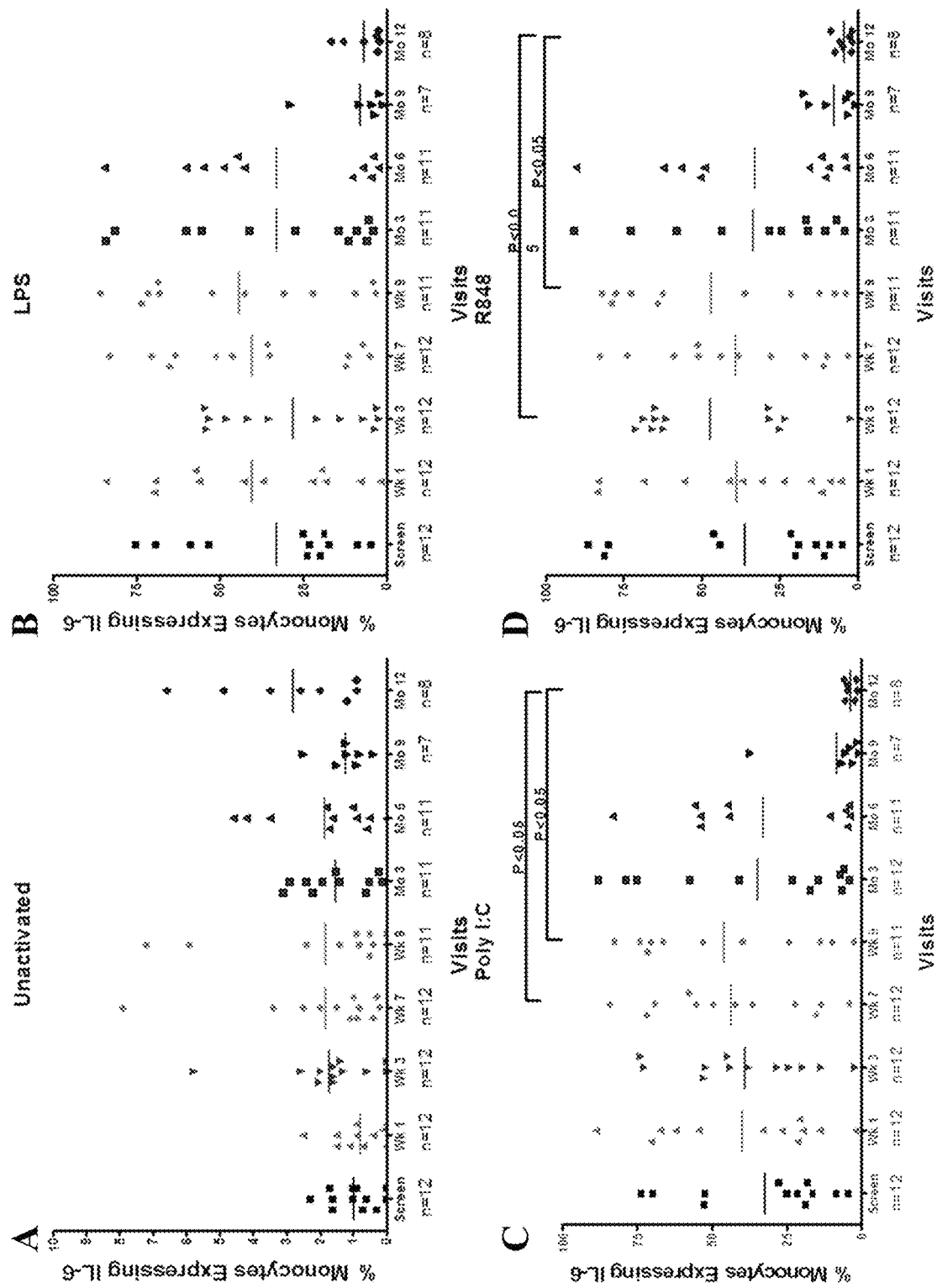
FIGS. 36A-36D illustrate percent of monocytes expressing IL-6 in T1D and control subjects over time.
Figures 37A, 37B, 37C, 37D:
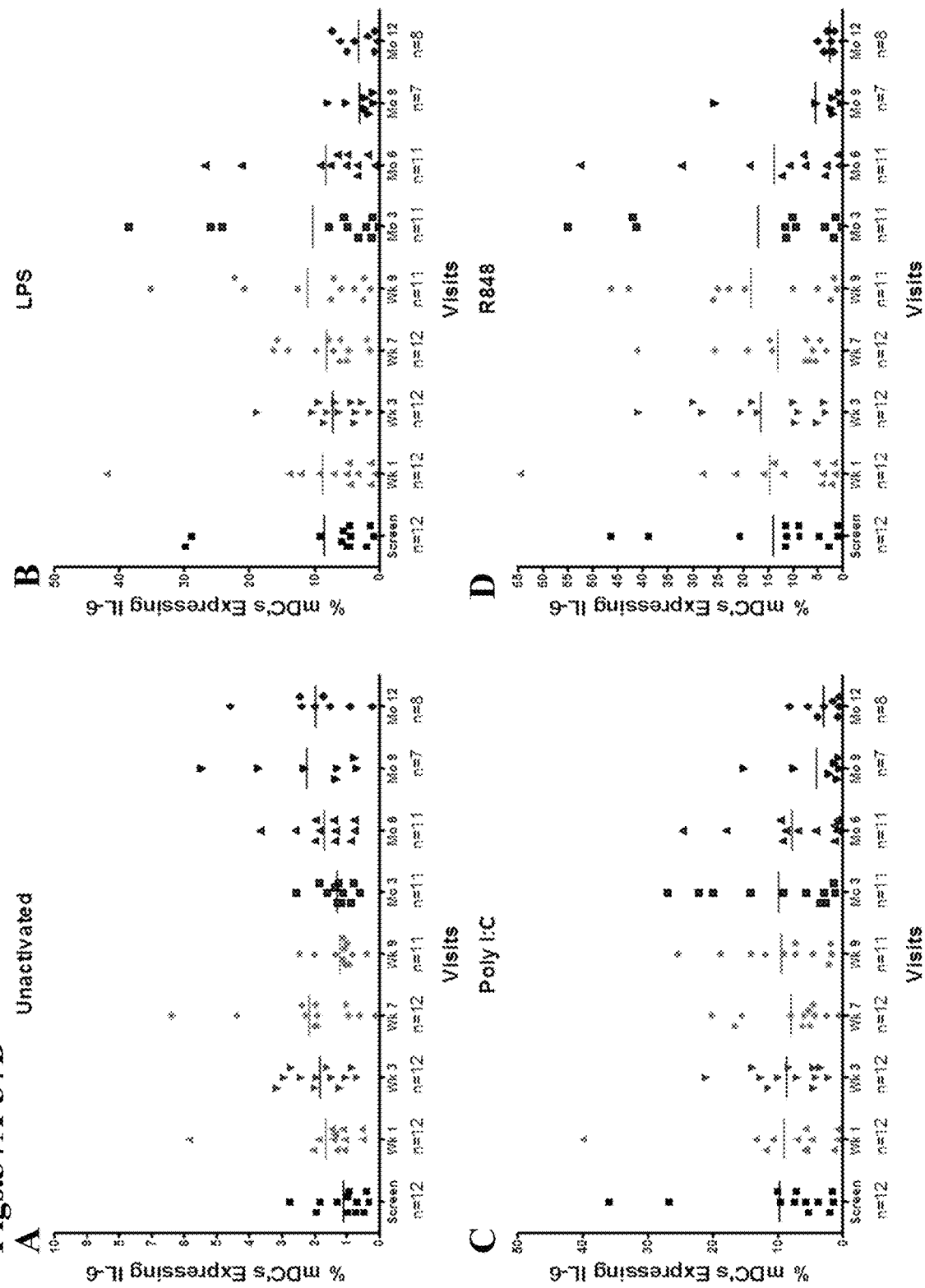
FIGS. 37A-37D illustrate percent of mDC's expressing IL-6 in T1D and control subjects over time.

FIG. 35 represents a plot of percent change in Poly-IC induced monocyte cell IL-6 expression in subjects over time. This plot illustrates that AAT-treatment reduced IL-6 expression in Poly I:C-stimulated monocytes long after the treatments were administered.

FIGS. 36A-36D illustrate percent of monocytes expressing IL-6 in T1D and control subjects over time. These plots illustrate that AAT-treatment reduced IL-6 expression in monocytes under various stimulus conditions long after the treatments were administered.

FIGS. 37A-37D illustrate percent of mDC's expressing IL-6 in T1D and control subjects over time. These plots illustrate that AAT-treatment reduced IL-6 expression in dendridic cells under various stimulus conditions long after the treatments were administered.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COMPOSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for reducing onset of an inflammatory disorder or adverse effects due to inflammation in a subject, the method comprising administering to the subject at risk of onset of an inflammatory disorder or adverse effects due to inflammation for 3 weeks or up to 18 months prior to onset of the disorder or adverse effects, a composition comprising human alpha 1-antitrypsin (AAT), a fusion AAT molecule thereof wherein the AAT fusion molecule comprises an AAT immunoglobulin Fc fusion polypeptide; and a therapeutically acceptable excipient; and reducing effects due to administering the composition to the subject.

2. The method of claim 1, wherein administering the composition to the subject comprises administering the composition for 8 weeks up to 18 months prior to an event.

3. The method of claim 1, wherein the AAT comprises naturally-occurring full-length AAT and is administered at about 60 to about 150 mg/kg per dose.

4. The method of claim 1, wherein the AAT comprises an AAT fusion molecule and is administered at about 0.01 to about 10 mg/kg.

5. The method of claim 1, wherein the composition is administered to the subject intranasally, intradermally, subcutaneously, by pump, intravenously or other method of administration.

6. The method of claim 1, wherein the subject is a human or other mammal.

7. The method of claim 1, wherein the subject has normal levels of AAT.

8. The method of claim 1, wherein the inflammatory disorder comprises macrophage, B cell or dendritic cell activation.

9. The method of claim 1, wherein the inflammatory disorder comprises an inflammatory lung disorder.

10. The method of claim 1, wherein the Fc comprises an Fc from IgG1, IgG2, IgG3, IgG4 or IgD.

11. The method of claim 10, wherein the Fc further comprises a hinge deletion or hinge truncation.

12. The method of claim 10, wherein the Fc comprises an Fc mutant.

13. The method of claim 1, wherein the subject is a healthy subject.

14. The method of claim 13, wherein the healthy subject is undergoing a procedure and the procedure is elective cosmetic surgery.

15. The method of claim 1, wherein the subject elects to have the cosmetic or reconstructive surgery.

16. The method of claim 1, wherein administering to the subject comprises administering to the subject for 9 weeks up to 18 months prior to an event.

17. A method for reducing bone marrow implantation rejection in a recipient subject, the method comprising administering to the recipient subject 3 weeks or up to 18 months prior to bone marrow implantation, a composition comprising human alpha 1-antitrypsin (AAT), a fusion AAT molecule thereof wherein the AAT fusion molecule comprises an AAT immunoglobulin Fc fusion polypeptide; and a therapeutically acceptable excipient; and reducing bone marrow implantation rejection in the recipient subject.

18. The method of claim 17, wherein the composition further comprises one or more anti-transplant rejection agent, anti-inflammatory agent, immunosuppressive agent, immunomodulatory agent, anti-microbial agent, anti-viral agent or a combination thereof.

19. The method of claim 18, wherein the immunomodulatory agent comprises one or more reducers of one or more cytokines.

20. The method of claim 19, wherein the one or more cytokines are selected from the group consisting of TNFα (tumor necrosis factor alpha), IL-6 (interleukin-6), IL-1 (interleukin-1), IL-1β, IL-12 (interleukin-12), IL-18 (interleukin-18), IFNγ (interferon gamma) and a combination thereof.

21. The method of claim 17, wherein the AAT comprises naturally-occurring full-length AAT and is administered from about 60 mg/kg to about 150 mg/kg per dose.

22. The method of claim 17, wherein the AAT comprises an AAT fusion molecule and is administered at about 0.01 to about 10 mg/kg.

23. The method of claim 17, wherein the composition is administered intranasally, intradermally, subcutaneously, by pump, intravenously or other method.

24. The method of claim 17, wherein the recipient subject is a human or other mammal.

25. The method of claim 17, wherein the recipient subject is a young adult or juvenile under the age of 25 years.

26. The method of claim 17, wherein the administering to the recipient subject comprises administering at least 8 weeks up to 18 months prior to bone marrow implantation.

27. The method of claim 26, wherein the subject is treated 3 weeks up to 9 months prior to the surgery.

28. The method of claim 17, wherein administering to the subject comprises administering to the subject for 9 weeks up to 18 months prior to bone marrow implantation.

29. A method for reducing side effects of cosmetic or reconstructive surgery in a subject, the method comprising administering to the subject for 3 weeks or up to 18 months prior to the cosmetic or reconstructive surgery, a composition comprising human alpha 1-antitrypsin (AAT), or a human alpha1-antitrypsin (AAT)-Fc fusion molecule; and a therapeutically acceptable excipient, and reducing side effects of the surgery.

30. The method of claim 29, wherein administering to the subject comprises administering to the subject for 8 weeks up to 18 months prior to the cosmetic or reconstructive surgery.

31. The method of claim 29, wherein administering to the subject comprises administering to the subject for 9 weeks up to 18 months prior to the cosmetic or reconstructive surgery.

\* \* \* \* \*